(12) United States Patent
Van Den Brink et al.

(10) Patent No.: US 11,564,973 B2
(45) Date of Patent: Jan. 31, 2023

(54) METHODS OF USE FOR IL-22 IN THE TREATMENT OF GASTROINTESTINAL GRAFT VS. HOST DISEASE

(71) Applicants: MEMORIAL SLOAN-KETTERING CANCER CENTER, New York, NY (US); EVIVE BIOTECHNOLOGY (SHANGHAI) LTD., Shanghai (CN)

(72) Inventors: Marcel Van Den Brink, New York, NY (US); Alan Hanash, New York, NY (US); Caroline Lindemans, Utrecht (NL); Tom Tang, Shanghai (CN)

(73) Assignees: MEMORIAL SLOAN-KETTERING CANCER CENTER, New York, NY (US); EVIVE BIOTECHNOLOGY (SHANGHAI) LTD, Shanghai (CN)

( * ) Notice: Subject to any disclaimer, the term of this patent is extended or adjusted under 35 U.S.C. 154(b) by 0 days.

(21) Appl. No.: 16/724,491

(22) Filed: Dec. 23, 2019

(65) Prior Publication Data
US 2021/0138038 A1 May 13, 2021

Related U.S. Application Data

(63) Continuation of application No. 15/035,055, filed as application No. PCT/US2014/064655 on Nov. 7, 2014, now abandoned.

(60) Provisional application No. 61/901,151, filed on Nov. 7, 2013.

(51) Int. Cl.
| | | |
|---|---|---|
| A61K 38/20 | (2006.01) | |
| C07K 14/54 | (2006.01) | |
| C07K 16/46 | (2006.01) | |
| C07K 16/42 | (2006.01) | |

(52) U.S. Cl.
CPC .............. *A61K 38/20* (2013.01); *C07K 14/54* (2013.01); *C07K 16/42* (2013.01)

(58) Field of Classification Search
None
See application file for complete search history.

(56) References Cited

U.S. PATENT DOCUMENTS

| | | |
|---|---|---|
| 2007/0172457 A1 | 7/2007 | Ebner |
| 2008/0293629 A1 | 11/2008 | Rosen |
| 2009/0221008 A1 | 9/2009 | Yu |
| 2011/0091417 A1 | 4/2011 | Gurney |
| 2011/0280828 A1 | 11/2011 | Abbas |
| 2013/0171100 A1 | 7/2013 | Yan |
| 2016/0287670 A1 | 10/2016 | Van Den Brink |

FOREIGN PATENT DOCUMENTS

| | | |
|---|---|---|
| WO | 2014145016 A1 | 9/2014 |

OTHER PUBLICATIONS

Couturier et al., "IL-22 deficiency in donor T cells attenuates murine acute graft-versus-host disease mortality while sparing the graft-versus-leukemia effect," LEUKEMIA, vol. 27, pp. 1527-1537, 2013.
International Search Report and Written Opinion of the International Searching Authority for PCT/US2014/64655, dated Mar. 27, 2015, 5 pages.
International Preliminary Report on Patentability and Written Opinion of the International Searching Authority for PCT/JS2014/64655, dated May 24, 2016, 11 pages.
Supplementary European Search Report for EP 14860998.5, dated Jul. 7, 2017, 9 pages.
Hanash et al. "Interleukin-22 protects intestinal stem cells from immune-mediated tissue damage and regulates sensitivity to graft versus host disease," Immunity, vol. 37(2), pp. 339-350, Aug. 24, 2012, Abstract Only.
Neto et al. "Interleukin-22 Forms Dimers that are Recognized by Two Interleukin-22R1 Receptor Chains," Biophysical Journal, vol. 94(5), pp. 1754-1765, Mar. 2008.
Dudakov et al. "Interleukin-22 drives endogenous thymic regeneration in mice," Science, vol. 336, No. 6077, pp. 91-95, Mar. 1, 2012.
Velardi et al. "Clinical strategies to enhance thymic recovery after allogeneic hematopoietic stem cell transplantation," Immunology Letters, vol. 155, No. 1-2, pp. 31-35, Sep. 1, 2013.
Dudakov et al. "Interleukin-22: immunobiology and pathology," Annual Review of Immunology, vol. 33, No. 1, pp. 747-785, Mar. 21, 2015.
Hanash et al. Host-derived I L-22 limits graft versus host disease and protects the intestinal stem cell niche. Blood. vol. 118, No. 21 Abstract No. 309 (Nov. 18, 2011). (Year: 2011).
Mertelsmann et al. 2013; IL-22 Administration Decreases Intestinal Gvhd Pathology, Increases Intestinal Stem Cell Recovery, and Enhances Immune Reconstitution Following Allogeneic Hematopoietic Transplantation, Blood 122(22): 2 (Dec. 5, 2013), Abstract Only.
Hanash et al. 2012, Effect of IL-22 on intestinal stem cells, GVHD-related tissue damage, and GVL., J. Clin Oncol., 30, No. 15 suppl (May 20, 2012) 6539-6539, Abstract Only.
Hanash, IL-22 in Epithelial Regeneration After Allogeneic Transplant, NIH Report portfolio online reporting tools, Description for Project No. 1K08HL115355-01, awarded 2012, Abstract Only.
Pickett et al 2009: STAT3 links IL-22 signaling in intestinal epithelial cells to mucosal wound healing, J Exp Med 206 (7): 1465-1472.

(Continued)

*Primary Examiner* — Elizabeth C. Kemmerer
*Assistant Examiner* — Regina M DeBerry
(74) *Attorney, Agent, or Firm* — Heslin Rothenberg Farley & Mesiti P.C.

(57) ABSTRACT

The present invention provides methods and compositions for the use of IL-22 for treating conditions of intestinal injury and inflammatory conditions such as graft vs. host disease. Specifically, IL-22 can be used to increase Intestinal Stem Cell (ISC) recovery and for enhancing immune reconstitution following allogeneic hematopoietic transplantation. In particularly preferred embodiments, the present invention provides methods of using therapeutic IL-22, including a dimeric form of IL-22, in therapeutic compositions for treating graft vs. host disease, including hepatic, thymic, gastrointestinal, or other graft vs. host disease in hematopoietic stem cell transplant patients and in patients with inflammatory intestinal conditions.

15 Claims, 59 Drawing Sheets

(56) References Cited

OTHER PUBLICATIONS

Figure 2A:
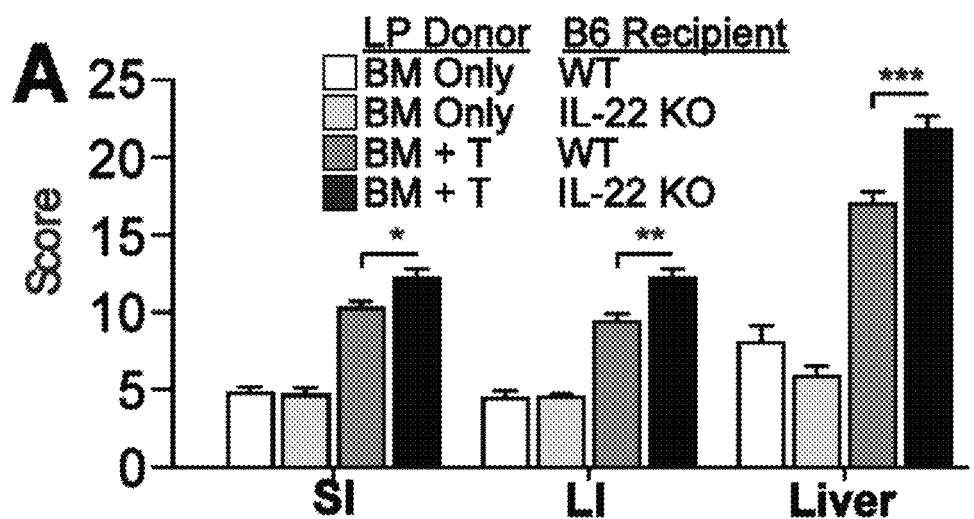

Sugimoto et al. 2008, IL-22 ameliorates intestinal inflammation in a mouse model of ulcerative colitis J Clin Invest: 118(2):534-544.
Sonnenberg et al 2011, Online Abstract, Border patrol: regulation of immunity, inflammation and tissue homeostasis at barrier surfaces by IL-22, Nat Immunol 12(5): 383-90.
Ponce et al., Jun. 2013, Graft-versus-host Disease After Double-Unit Cord Blood Transplantation Has Unique Features and an Association with Engrafting Unit-Recipient HLA-match Biol Blood Marrow Transplant 19(6): 904-911.
Diefenbach 2012, Interleukin-22, the Guardian of the Intestinal Stem Cell Niche?Immunity 37(2): 196-198.
Takatsuka et al 2003, Intestinal Graft-Versus-Host Disease, Drugs 63(1): 1-15.
Asplund and Gramlich 1998, Chronic Mucosal Changes of the Colon in Graft-versus Host Disease, Mod Pathol 11(6): 513-515.
Muhl et al 2013, IL-22 in tissue-protective therapy Br. J. Pharmacol. 169(4): 761-771.
Ferrara et al 2009, Graft-Versus-Host Disease, Lancet 373(9674): 1550-1561.
Zhang et al. 2010, Solid Organ Transplant-Associated Acute Graft-Versus-Host DiseaseArch Pathol Lab Med. 134: 1220-1224.
Kuroiwa et al 2001, Hepatocyte growth factor ameliorates acute graft-versus-host disease and promotes hematopoietic function, J. Clin. Invest 107: 1365-1373.
Krijanovski et al. 1999, Keratinocyte Growth Factor Separates Graft-Versus-Leukemia Effects From Graft-Versus-Host Disease, Blood 94(2): 825-831.
Li and Jasper 2016, Gastrointestinal stem cells in health and disease: from flies to humans, Dis Model Mech 9: 487-499.
Sabat et al., Therapeutic opportunities of the IL-22-IL-22R1 system, Nature 13: 21-38 (2014)—published online Dec. 2013.
Ramaswamy and Langford, Antinociceptive and immunosuppressive effect of opioids in an acute postoperative setting: an evidence-based review, BJA Education, 17(3): 105-110 (2017).
Lindeman et al 2014, IL-22 Protects Intestinal Stem Cells from GVHD, Biol Blood Marrow Transplant, 20(2): Supp. Suppl. 1, pp. S53-S54. Abstract No. 49. (Feb. 2014).
Hanash et al. 2012, Host-Derived IL-22 Biol Blood Marrow Transplant, 18(2): Supp. Suppl. 2, pp. S361-S362. Abstract No. 426. (Feb. 2012).
Zhao et al., 2013, The identification and characteristics of IL-22-producing T cells in acutegraft-versus-host disease following allogeneic bone marrow transplantation, Immunobiology 218 (2013) 1505-1513.
Ma et al., IL-22 is required for Th17 cell-mediated pathology in a mouse model of psoriasis-like skin inflammation, J. Clin. Invest. 118:597-607 (2008).
Ferrara, 1993, Cytokine dysregulation as a mechanism of graft versus host disease, Current Opinion in Immunology, 5:794-799.
Varona, 2006, CCR6 regulates CD4+ T-cell-mediated acute graft-versus-host disease responses, Blood, Jul. 1, 2005 vol. 10, 18-26.
Rutz et al, 2013, IL-22, not simply a Th17 cytokine, Immunological Reviews, vol. 252: 116-132.
Hale and Cianciolo, 2008, Treatment of experimental colitis in mice with LMP-420, an inhibitor of TNF transcription, Journal of Inflammation 2008, 5:4.
Kim et al., 2006, Involvement of lymphocytes in dextran sulfate sodium induced experimental colitis, World J Gastroenterol Jan. 14, 2006; 12(2):302-305.
Lamarthée at al. (2016), Interleukin-22 in Graft-Versus-Host Disease after Allogeneic Stem Cell Transplantation, Front. Immunol. 7:148.
Talbot et al., "Graft-Versus-Host-Disease" in: Talbot et al., Biopsy Pathology in Colorectal Disease, 2Ed, FL, CRC Press, 2006, pp. 192-194.
Zhao et al., 2014, Interleukin-22 Aggravates Murine Acute Graft-Versus-Host Disease by Expanding Effector T Cell and Reducing Regulatory T Cell, Journal of Interferon & Cytokine Research vol. 34, No. 9, pp. 707-715.
Carlson et al., 2009, In vitro-differentiated TH17 cells mediate lethal acute graft-versus-host disease with severe cutaneous and pulmonary pathologic manifestations, BLOOD, Feb. 5, 2009 vol. 113, No. 6, pp. 1365-1374.
RePORTER Frequently Asked Questions (FAQS) [online] retrieved on Sep. 30, 2021], Retrieved from https://report.nih.gov/faqs.
Examination report No. 1, dated May 20, 2019, issued by IP Australia in connection with Australian patent application No. 2014346554, which is a National Stage Entry of PCT/US2014/064655, to which PCT application the present application claims priority.
Examination report No. 2, dated Apr. 29, 2020, issued by IP Australia in connection with Australian patent application No. 2014346554, which is a National Stage Entry of PCT/US2014/064655, to which PCT application the present application claims priority.
Notice of First Office Action, dated Aug. 28, 2018, issued by China National Intellectual Property Administration in connection with Chinese patent application No. 201480072525.4 which is a National Stage Entry of PCT/US2014/064655, to which PCT application the present application claims priority.
Notice of Second Office Action, dated Aug. 14, 2019, issued by China National Intellectual Property Administration in connection with Chinese patent application No. 201480072525.4 which is a National Stage Entry of PCT/US2014/064655, to which PCT application the present application claims priority.
Decision of Rejection, dated Jun. 3, 2020, issued by China National Intellectual Property Administration in connection with Chinese patent application No. 201480072525.4 which is a National Stage Entry of PCT/US2014/064655, to which PCT application the present application claims priority.
Revocation Request, filed in the European Patent Office in connection with European Patent No. 3065777, which issued from European Patent Application No. 14860998.5, which application was a Regional Stage Entry of PCT/US2014/064655, to which PCT application the present application claims priority.
Hanash et al. "Interleukin-22 protects intestinal stem cells from immune-mediated tissue damage and regulates sensitivity to graft versus host disease," Immunity, vol. 37(2), pp. 339-350, Aug. 24, 2012.
Ponce et al., 2020, "A Phase 2 Study of F-652, a Novel Tissue-Targeted Recombinant Human Interleukin-22 (IL-22) Dimer, for Treatment of Newly Diagnosed Acute Gvhd of the Lower GI Tract," Biology of Blood and Marrow Transplantation: Transplantation and Cellular Therapy, Mar. 2020, vol. 26 3S, Abstract 68, at pp. S51-S52.
Study Results, "Study of IL-22 IgG2-Fc (F-652) for Subjects With Grade II-IV Lower GI aGVHD," ClinicalTrials.gov Identifier: NCT02406651 [online, retrieved on Jun. 27, 2022], Retrieved from https://www.clinicaltrials.gov/ct2/show/results/NCT02406651?term=NCT02406651&draw=2&rank=1&view=results.

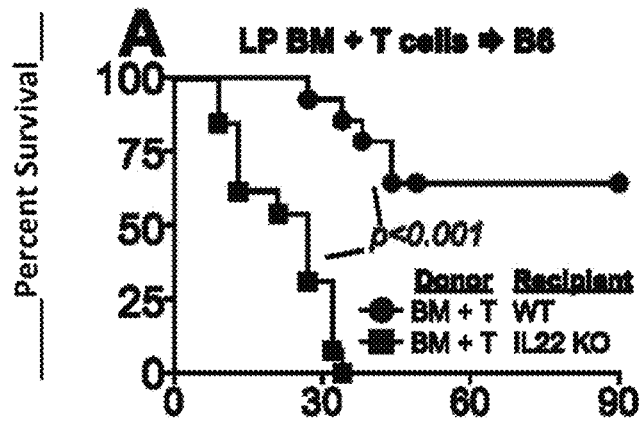
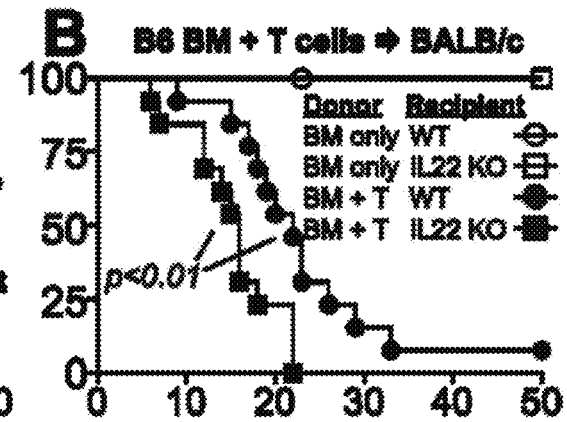
FIG. 1A
FIG. 1B
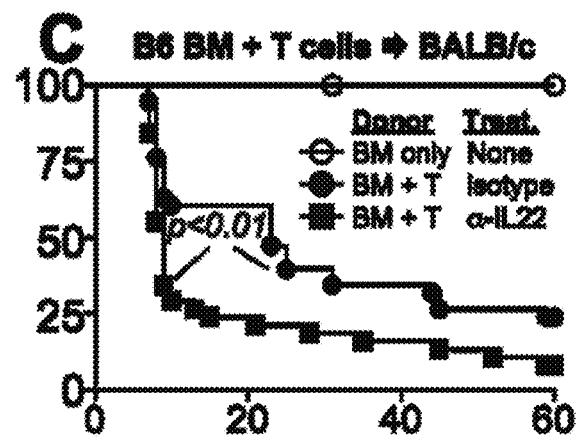
FIG. 1C

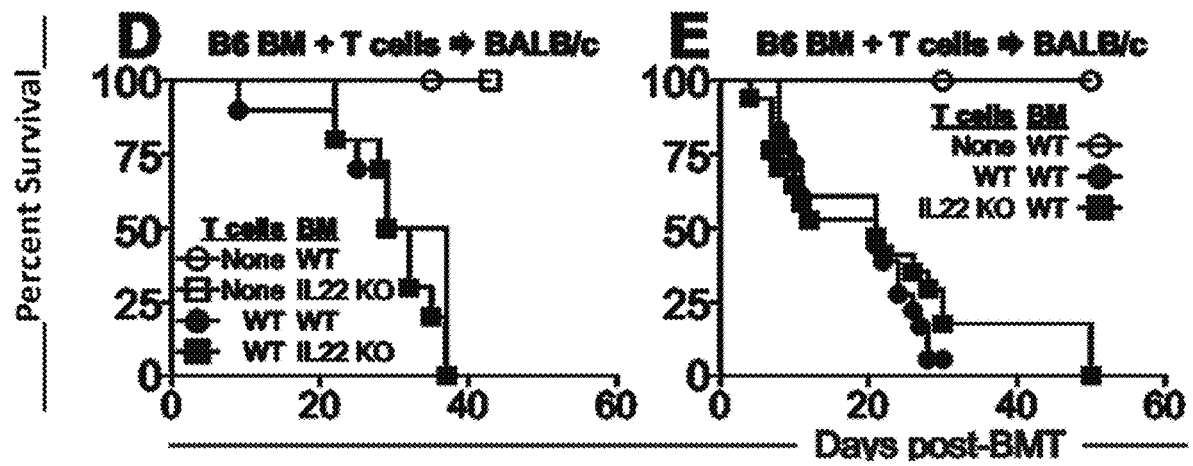
FIG. 1D
FIG. 1E
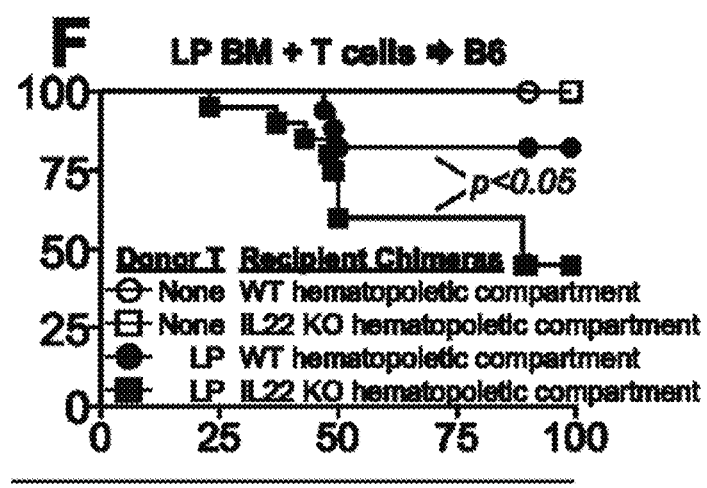
FIG. 1F

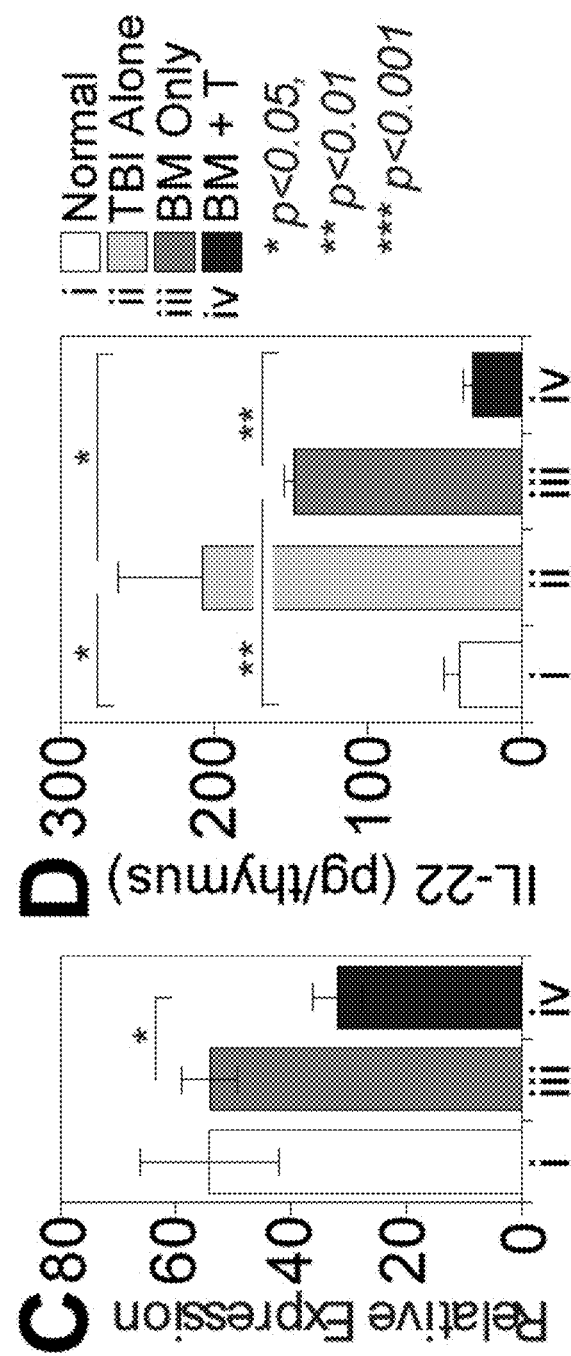

Perimeter

METHODS OF USE FOR IL-22 IN THE TREATMENT OF GASTROINTESTINAL GRAFT VS. HOST DISEASE

CROSS-REFERENCE TO RELATED APPLICATIONS

This application claims priority to U.S. Provisional Application No. 61/901,151, filed Nov. 7, 2013, the entire contents of which are incorporated herein in their entirety.

GOVERNMENT RIGHTS STATEMENT

This invention was made with U.S. Government support under Grant Number K08 KHL115355A and P01 CA023766, awarded by National Institutes of Health. The United States Government has certain rights in the invention.

FIELD OF THE INVENTION

The present invention provides methods and compositions for the use of IL-22 for treating conditions of intestinal injury and inflammatory conditions such as graft vs. host disease. Specifically, IL-22 can be used to increase Intestinal Stem Cell (ISC) recovery and for enhancing immune reconstitution following allogeneic hematopoietic transplantation. In particularly preferred embodiments, the present invention provides methods of using therapeutic IL-22, including a dimeric form of IL-22, in therapeutic compositions for treating graft vs. host disease, including hepatic, thymic, gastrointestinal, or other graft vs. host disease in hematopoietic stem cell transplant patients and in patients with inflammatory intestinal conditions.

BACKGROUND OF THE INVENTION

Mechanisms regulating host tissue recovery from immune-mediated damage in gastrointestinal graft vs. host disease (GI-GVHD) remain incompletely understood. Current strategies to reduce clinical GVHD have the undesired effect of limiting both post-transplant immune function and therapeutic (beneficial) graft vs. leukemia/lymphoma (GVL) responses. Of particular concern is the maintenance and regeneration of intestinal epithelial tissues during graft vs. host disease (GVHD) because GVHD causes intestinal cell pathology which interferes with intestinal functions.

GI GVHD is the predominant contributor to acute GVHD-related mortality after allogeneic hematopoietic stem/progenitor cell transplantation.

Thus, there remains a need for post-transplant strategies for selectively promoting intestinal epithelial regeneration after allogeneic hematopoietic stem/progenitor cell transplantation (allo-HCT) to reduce GVHD without limiting therapeutic graft vs. leukemia/lymphoma (GVL) responses.

SUMMARY OF THE INVENTION

The present invention is based on the observation that administration of IL-22 in vivo following allogeneic bone marrow transplantation (BMT) enhanced recovery of intestinal stem cells (ISC), reduced intestinal pathology from graft vs. host disease (GVHD) and improved post-transplant overall survival without augmentation of stem cell niche function or alteration of alloreactive immunity. IL-22 increases recovery of ISCs from immune-mediated pathology by accelerating regeneration of the ISC pool. IL-22 directly augmented proliferation of Lgr5+ISCs in vivo and ex vivo. This resulted in augmented recovery of mature epithelium without augmenting growth factor production by the stem cell niche.

In one aspect, therefore, the present invention relates to a method for enhancing the growth/proliferation of intestinal stem cells (ISC), the method comprising contacting ISC with exogenous or recombinant interleukin-22 (IL-2), or a dimer, fusion protein or conjugate thereof under conditions to promote growth of ISC in vivo or in vitro. In some embodiments, the ISC are Lgr5+ cells.

In a related aspect, the present invention relates to a method for promoting the recovery/regeneration of gastrointestinal epithelial cells in a subject following damage to the epithelial lining of the gastrointestinal (GI) tract, the method comprising contacting intestinal stem cells of the subject with IL-22 or a dimer, fusion protein (for example an Fc fusion protein) or conjugate thereof. Damage to the GI tract may be the result of inflammatory intestinal disease, (for example, inflammatory bowel disease, ulcerative colitis, Crohn's disease) radiation, intestinal autoimmune disease or transplant (GVHD).

In yet another aspect, the invention relates to a method for treating GVHD in a subject following a transplant, the method comprising administering to the subject a therapeutically effective amount of IL-22 or a dimer, fusion protein or conjugate thereof. The method does not require immunosupression to achieve its therapeutic effect.

In one aspect, the invention relates to a method in which administration of IL-22 is begun once onset of symptoms associated with intestinal injury is observed by a skilled artisan. In one embodiment, IL-22 is administered to the subject beginning from 1 day to 6 months following transplant; in one embodiment, IL-22 is administered to the subject beginning from 1 week to 4 months following transplant.

In another aspect, the invention relates to an IL-22 or dimer, fusion protein, or conjugate thereof for use in the recovery/regeneration of intestinal epithelial cells or in the treatment of or prevention/inhibition of GVHD.

Definitions

To facilitate an understanding of the present invention, a number of terms and phrases are defined below:

As used herein, the term "IL-22 polypeptide" or "IL-22" or "IL22" or "IL-22 protein" refers to a biologically active polypeptide capable of producing the biological activity as described herein. IL-22 of the present invention includes but not limited to human IL-22, recombinant human IL-22, murine IL-22 and/or recombinant murine IL-22. Specific polypeptide sequences are described in U.S. Patent Appln. No. US2003/0100076, U.S. Pat. Nos. 7,226,591 and 6,359,117, herein incorporated by reference in their entirety. "IL-22" also includes modified IL-22, such as pegylated IL-22 and covalently modified IL-22 proteins. The IL-22 polypeptides used herein may be isolated from a variety of sources, such as from human tissue types or from another source, or prepared by recombinant or synthetic methods. For example, descriptions of the preparation of, purification of, derivation of, formation of antibodies to or against, administration of, compositions containing, treatment of a disease with, etc., pertain to each polypeptide of the invention individually. Additionally, the IL-22 for use in the present inventions may be a product of a recombinant method wherein the IL-22 encoding DNA is administered to a subject, for example, such as lactobacilli expressing IL-22.

The term "IL-22 polypeptide" also includes variants of the IL-22 polypeptides. The IL-22 of the present invention may also be modified in a way to form a chimeric molecule comprising IL-22 fused to another, heterologous polypeptide or amino acid sequence. The term IL-22 as used herein, includes both a monomer and a dimer form of IL-22. However unless otherwise specified herein rIL-22 was used in these methods. IL-22 is also known as interleukin-10 related T cell-derived inducible factor (IL-TIF).

As used herein, the term "IL-22 monomer" refers to one unit of an IL-22 protein.

As used herein, the term "IL-22 dimer" refers to a protein having more than one unit of an IL-22 molecule, for one example, an IL-22 dimer may have two IL-22 molecules linked together using linkers such as a short polypeptide, a chemical bond, and a covalent bond. In some embodiments, an IL-22 dimer contains two duplicate IL-22 molecules, in other embodiments, an IL-22 dimer is made up of different IL-22 proteins. Further examples of IL-22 dimers that may find use in the present inventions are described in United States Patent Application 20130171100, herein incorporated by reference in its entirety. One suitable IL-22 dimer is a recombinant IL-22 dimerized protein containing human interleukin 22 (IL-22) and produced in transformed Chinese Hamster Ovary (CHO) cells in serum-free culture produced by Evive Biotechnology (Shanghai) Ltd. IL-22 dimers are described, for example, in United States Patent Application 20130171100, including sequence information, herein incorporated by reference in its entirety. IL-22 dimer forming polypeptides used herein may be isolated from a variety of sources, such as from human tissue types or from another source, or prepared by recombinant or synthetic methods. In some embodiments, an IL-22 dimer comprises a carrier protein, including but not limited to an Fc fragment of human IgG (1, 2, 3, 4), or human albumin. IL-22 can be localized at the C-terminal or N-terminal of the carrier protein.

In some embodiments, the IL-22 dimer used in any one of the methods described herein comprises two monomeric units, wherein each monomeric unit comprises an IL-22 domain and a dimerization domain. In some embodiments, each monomeric unit of the IL-22 dimer comprises an IL-22 domain linked to a dimerization domain via an optional linker sequence, such as a linker sequence that is about 5 to about 50 amino acids. In some embodiments, the dimerization domain comprises at least two cysteines capable of forming intermolecular disulfide bonds. In some embodiments, the dimerization domain comprises at least a portion of the Fc fragment. In some embodiments, the Fc fragment comprises CH2 and CH3 domains. In some embodiments, the IL-22 dimers comprise two monomeric units as described in United States Patent Application 20130171100, incorporated specifically herein by reference. In some embodiments, the IL-22 dimer is administered intravenously.

As used herein, the term "graft-versus-host" or "GVH" refers to an immune response of graft (donor) cells against host cells and tissues.

As used herein, the term "graft vs. host disease" or "GVHD" refers to a condition, including acute and chronic, resulting from transplanted (graft) cell effects on host cells and tissues resulting from GVH. In other words, donor immune cells infused within the graft or donor immune cells that develop from the stem cells, may see the patient's (host) cells as foreign and turn against them with an immune response. As examples, patients who have had a blood or marrow transplant from someone else are at risk of having acute GVHD. Even donors who are HLA-matched with the recipient can cause GVHD because the donor cells can potentially also make an immune response against minor antigen differences in the recipient. Acute graft-versus-host disease (GVHD) is specifically a disorder caused by donor immune cells in patients who have had an allogeneic marrow or blood cell transplantation. The most commonly affected tissues are skin intestine and liver. In severe cases, GVHD can cause blistering in the skin or excessive diarrhea and wasting. Also, inflammation caused by donor immune cells in the liver can cause obstruction that causes jaundice. Other tissues such as lung and thymus may also become affected. The diagnosis is usually confirmed by looking at a small piece of skin, liver, stomach or intestine with a microscope for observation of specific inflammatory characteristics. In severe cases, the liver does not function properly to eliminate waste products from the body. Acute GVHD usually begins during the first 3 months after the transplant. In some cases, it can persist, come back or begin more than 3 months after the transplant. Prednisone and/or other immunosuppressive medications are used to treat acute graft-versus-host disease. Other immunosuppressive medications are used if treatment with prednisone is not successful, even though a large proportion of patients is refractory to immunosuppressive medication and die.

Patients who have had acute GVHD and survive have a greater risk of developing chronic GVHD. Older patients, patients who received a peripheral blood (instead of bone marrow) transplant, and patients who had a mismatched or unrelated donor have a greater risk of chronic GVHD. Chronic GVHD usually begins later after transplant and lasts longer than acute GVHD. Patients with Chronic GVHD may present with a wide variety of symptoms. Skin rash and/or mouth sores are among the most common initial signs of the disease. Unlike acute GVHD, chronic GVHD can cause damage in the glands that produce tears in the eyes and saliva in the mouth resulting in dry eyes or a dry mouth. Patients may have mouth ulcers causing pain while eating, skin rashes, or liver inflammation. Chronic GVHD can also cause many other problems. One such problem is formation of scar tissue in the skin (cutaneous sclerosis) and joints. Another such problem is chronic damage to air passages in the lungs (bronchiolitis obliterans syndrome). Prednisone or other similar anti-inflammatory or immunosuppressive medications are used to treat chronic graft-versus-host disease. Other immunosuppressive medications can be used if treatment with prednisone is not successful. Just as in acute GVHD a large proportion of patients is not cured from chronic GVHD.

As used herein, the term "graft-versus-leukemia" or "GVL" or "Graft-versus-tumor effect" or "GVT" refers to a beneficial therapeutic immune reaction of the grafted donor T lymphocytes against the diseased bone marrow and residual tumor cells of the recipient.

As used herein, the term "gastrointestinal graft vs. host disease" and "GI-GVHD" refers to damage caused by donor immune cells to host tissue of the stomach and intestine which can cause loss of appetite, nausea, vomiting, or diarrhea as part of GVHD, either acute or chronic. In severe cases, GI-GVHD can cause pain in the abdomen and bleeding in the stomach or intestines.

As used herein, the term "allogeneic transplant" refers to donor blood infusions or marrow stem cell transplants from a donor to a host patient. In other words, the patient receives bone marrow or blood stem cells from a tissue-matched or a close matched donor, i.e. matched at major HLA loci, who may or may not be a relative. Identical twin allogeneic transplants are called syngeneic transplants.

As used herein, the term "hematopoietic stem cell transplantation" or "HSCT" or "hematopoietic cell transplantation" or "HCT" refers to a transplantation of multipotent hematopoietic cells, including stem cells, usually derived from bone marrow, peripheral blood, or umbilical cord blood.

As used herein, the term "allogeneic HSCT" refers to transplantation of multipotent hematopoietic stem cells from one individual to another. Such allogeneic HSCT is done in patients having certain cancers of the blood or bone marrow, such as multiple myeloma or leukemia, congenital immunodeficiencies and bone marrow failures or other hematologic disease. In these cases, the recipient's immune system is usually destroyed with radiation or chemotherapy before the transplantation. Infection and graft-versus-host disease is a major complication of HSCT.

As used herein, the term "intestinal stem cell" and "ISC" refers to a multipotent stem cell, such as a Lgr5+ cell.

As used herein, the term "progenitor cell" in reference to an intestinal cell refers to multipotent cells that may give rise to differentiated cells of the small or large intestine, such as a columnar cell and a goblet cell.

As used herein, the term "crypt base" in reference to a cell refers to a multipotent stem cell found in the crypt area of the intestine.

As used herein, the term "Paneth cell" or "Davidoff's Cell" refers to a specialized type of epithelial cell found in the small intestine and the appendix. A Paneth's cell or Paneth cell is derived from an intestinal stem cell.

As used herein, the term "organoid" in reference to an intestinal organoid comprising a central lumen lined by a villus-like epithelium that result from culturing of epithelial stem cells or isolated crypts in a culture medium. Crypts refer to intestinal stem/progenitor cell niche at the base of the epithelium As used herein, "cells" refer to the structural unit of an organism consisting of a nucleus and organelles surrounded by a semipermeable cell membrane. It is not intended to be limited to live or functioning cells.

As used herein, the term "contacting" or "treating" or "administering" a compound to a cell or tissue, such as an IL-22 protein, or IL-22 protein composition, or cytokine, or cytokine composition and the like, refers to placing the compound in a location that will allow it to touch the cell in order to produce "contacted" or "treated" cells. The contacting may be accomplished using any suitable method. For example, in one embodiment, contacting is by adding the compound to a tube of cells. Contacting may also be accomplished by adding the compound to cells in a microtiter plate. Contacting may also be accomplished by adding the compound to a culture of the cells or to an organoid culture. It is not meant to limit how the compound contacts the cells. In one embodiment, contacting may be accomplished by administration of the compound, such as an IL-22 molecule composition to an animal in vivo.

As used herein, the terms "culture media," and "cell culture media," refers to media that are suitable to support the growth of cells in vitro (i.e., cell cultures). It is not intended that the term be limited to any particular cell culture medium. For example, it is intended that the definition encompass outgrowth as well as maintenance media. Indeed, it is intended that the term encompass any culture medium suitable for the growth of the cell cultures of interest.

The term "sample" such as a "test sample" is used in its broadest sense. In one sense it can refer to an animal cell or tissue including a human cell or tissue. In another sense, it is meant to include a specimen or culture obtained from any source, in particular as a biological sample. Biological samples may be obtained from animals (including humans) and encompass fluids, solids, gases, tissues, cells, blood bone marrow and bones.

As used herein, the term "primary isolation" refers to the process of obtaining cells directly from a sample. Thus, primary isolation of cells, such as cells isolated directly from mice or humans used for flow cytometry analysis, involves such processes as removing tissue from a subject, such as a bone marrow sample, or intestinal sample, etc. followed by digestion in an enzyme, for example, dispase. Primary isolation may be accomplished using solid or semi-solid agar media, or in liquid.

As used herein, the term "portion" when used in reference to a population of cells (as in "a portion of intestinal cells" or "a portion of bone marrow cells") refers to at least one cell of that population up to 99% of those cells. For example, where contacting results in at least a "portion" of said cell population, it should be clear that portion is with reference to a population.

As used herein, "polypeptide" or "protein" refers to an amino acid, amino acid sequence, oligopeptide, peptide, or protein or portions thereof whether naturally occurring or synthetic.

As used herein, the term "portion" when used in reference to a protein (as in "a portion of a given protein") refers to fragments of that protein. The fragments may range in size from four amino acid residues to the entire amino sequence minus one amino acid.

As used herein, the term "TBI" refers to "total body irradiation" as described herein.

As used herein, "lymphoid" in reference to a cell refers to those of the lymphoid lineage such as T cells, B cells and NKT (natural killer T) cells.

As used herein, "myeloid" in reference to a cell refers to those cells of a myeloid lineage such as macrophages (and monocytes), granulocytes (including neutrophils, eosinophils and basophils).

As used herein, the term "altered function" refers to a change in function, either increasing a function or decreasing a function, for example, a change in cell numbers, such as total thymocytes, a change in cell type, such as a change in the number of pre B cells, a change in the number of CD8+ cells, a change in function, such as epithelial cells capable of secreting a specific cytokine or inducing survival or maturation of a specific cell type, and the like.

For the purposes of the present invention, "increasing" or "increased" or "upregulated" or "enhanced" or "display increased function" or "increased function" or "enhancing" in relation to function, refers to a higher level of an action or a cell type, such as an increased number of a specific cell type, i.e. mature functional intestinal cells, mature functional T cells, or an amount of a compound compared to a control or wild-type. Increased function may increase a cell type, such as when "Paneth cell production is increased" or when "lymphoid cell production is increased", etc., for example, treating intestinal cells with IL-22 as described herein increased production of basal crypt cells, Paneth cells, and the like, and when treating bone marrow cells, in vivo, increased cell function of bone marrow cells increased lymphoid cells, for example, increased immature B cells, a pre-B cell, etc., a myeloid cell type, such as granulocytes, macrophages, etc. Thus, examples of increased mature functional lymphoid cells from bone marrow are increased (enhanced) numbers of at least one lymphoid cell type, such as immature B cells, a pre-B cell, etc. during GVL. Further, examples of contemplated enhanced or enhancing immune function may also refer to enhancing immunocompetence, such as methods wherein immunocompromised patients having reduced immune function, such as reduced T-cell antigen receptor repertoires, reduced cytokine secretion, reduced proliferative responses to antigen, and the like, are treated with compositions comprising IL-22 resulting in increased immune function. Increased immune function may be measured as an increase in any one of T-cell antigen receptor repertoires, cytokine secretion, proliferative responses to antigen, ability to respond to infections, and the like.

For the purposes of the present invention, "decreasing" or "decreased" or "reduced" or "reduced function" or "down-regulated" or "having reduced function" refers to a lower level of production compared to a control or wild-type, such that "cells have reduced function" such as a reduced cell division, reduced numbers of progeny cells differentiating into differentiated cell types, such as reduced numbers of Paneth cells generated from intestinal stem cells and intestinal progenitor cells, etc. Another example of reduced function may be a lowered production of a cytokine, i.e. IL-22 in knock-out (KO) mice compared to IL-22+/+ or wild-type mice. As other examples, a reduced function is thymic epithelial cells producing a lower number of mature functional thymocytes, a decreased function is bone marrow cells producing a reduced number of mature functional lymphoid cells, bone marrow derived stem cells have decreased numbers of lymphoid cells. In other words, a reduced function may also be an altered function, for one example, altered bone marrow immune cell generation may show that bone marrow derived stem cells have (or produce) decreased lymphoid cells. Having a reduced function is not meant to be a static result. In some embodiments, contacting or administering an IL-22 composition of the present inventions may alter a function, such as when IL-22 induces cells having reduced function to display increased function, see Examples.

As used herein, the term "in vitro assay" refers to any in vitro assay used to measure the increase or decrease of function or number of cells or cell subtypes. Readouts for in vitro assays of organoid cultures could include for examples, flow cytometry measurements of intestinal stem cell progeny, such as basal crypt cells. Readouts for in vitro assays of immune function could include for examples, T cell functional assays, including cytokine production, T cell subtypes, granulocytes, stromal cells, proliferation, extent of apoptosis, etc., see assays used in the Examples.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein, particularly in reference to a "human subject." For the purposes of the present inventions, a subject may be immunocompromised, i.e. not able to fight off infections or control abnormal cell growth. Examples of immunocompromised subjects include subjects that have any of the following conditions, chemotherapy, exposure to radiation, deliberate irradiation, human immunodeficiency virus infections, transplantation, etc.

The terms "treatment", "treating" and the like are used herein to generally mean obtaining a desired pharmacological and/or physiological effect. In relation to a therapeutic treatment of subject the effect may be prophylactic in terms of completely or partially preventing a disease or symptom thereof and/or may be therapeutic in terms of partially or completely curing a disease and/or adverse effect attributed to the disease. Thus "treatment" refers to both therapeutic treatment and prophylactic or preventative measures, wherein the object is to prevent or slow down (lessen) the targeted pathologic condition or disorder. Subjects in need of treatment include those already with the disorder as well as those prone to have the disorder or those in whom the disorder is to be prevented.

As used herein, when referring to a method of the present invention the term "treatment" covers any treatment of a disease in a mammal, particularly a human, and includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease. The present invention is directed towards treating patients with medical conditions relating to a loss of immunocompetence from a treatment related to a disease such as irradiation, chemotherapy, immunosuppression, etc. Accordingly, a treatment of the invention would involve preventing, inhibiting or relieving any medical condition where a desired level of immunocompetence would be achieved by the use of an IL-22 composition of the present inventions. In certain embodiments, treatment refers to exposing a subject to a therapy directed towards treating a disease, such as irradiation, chemotherapy, and the like.

As used herein, the term "administering" or "administration" refers to the act of giving a drug, prodrug, pharmaceutical composition, or other agent, or therapeutic treatment (e.g., a composition of the present invention) to a physiological system (e.g., a subject or in vivo, in vitro, or ex vivo cells, tissues, and organs). Acceptable routes of administration to the human body can be through the eyes (ophthalmic), mouth (oral), skin (transdermal), nose (nasal), lungs (inhalant), mucosal (e.g., oral mucosa or buccal), rectal, ear, by injection (e.g., intravenously, subcutaneously, intratumorally, intraperitoneally, etc.) and the like. Administration "in combination with" one or more further therapeutic agents includes simultaneous (concurrent) and consecutive administration in any order.

As used herein, the term "pharmaceutical" or "therapeutic" in reference to a composition refers to the combination of an active agent (for example, in an effective amount) (e.g., such as an IL-22 protein or IL-22 DNA)) with a carrier, inert or active, making the composition especially suitable for diagnostic or therapeutic use in vitro, in vivo or ex vivo (in vitro).

An "effective amount" of a polypeptide disclosed herein or an agonist or antagonist thereof is an amount sufficient to carry out a specifically stated purpose. An "effective amount" may be determined empirically and in a routine manner, in relation to the stated purpose. Examples of effective amounts On using the pharmaceutical composition, a safe and effective amount of the IL-22 dimer of the present invention is administered to a mammal (e.g. human) in need thereof, in which the dosage administrated is a pharmaceutically acceptable effective administration dosage. As one example, for a human of 60 kg, the administration dosage is usually 0.01-300 mg; in a preferred embodiment, the administration dosage is 0.5-100 mg, see, for example, United States Patent Application 20130171100, herein incorporated by reference in its entirety.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also may include stabilizers and preservatives. Examples of carriers, stabilizers, and adjuvants are described in the art (See e.g., Martin, Remington's Pharmaceutical Sciences, 15th Ed., Mack Publ. Co., Easton, Pa. (1975), incorporated herein by reference).

The terms "pharmaceutically acceptable" or "pharmacologically acceptable," as used herein, refer to compositions that do not substantially produce adverse reactions (e.g., toxic, allergic, or immunological reactions) when administered to a subject. Examples of forms of IL-22 of the present invention used for administration comprise ointment, powder, patch, sprayer, and inhalant.

As used herein, "cytokine" refers to a protein or glycoprotein that is used in an organism as signaling compounds. It is intended to include homologues and synthetic versions. Examples include IL-22, IL-23, IL-21, the IL-10 family, IL-7, the interferon (IFN) family, CC chemokines, CXC chemokines, and the like.

As used herein the term "biologically active polypeptide" refers to any polypeptide which maintains a desired biological activity, for one example, biological IL-22 activities as described herein, such as increasing intestinal stem cell and intestinal progenitor cell division, maturation, and the like.

Where "amino acid sequence" is recited herein to refer to an amino acid sequence of a naturally occurring protein molecule, "amino acid sequence" and like terms, such as "polypeptide" and "protein" are not meant to limit the amino acid sequence to the complete, native amino acid sequence associated with the recited protein molecule. As used herein the term "recombinant protein" or "recombinant polypeptide" refers to a protein molecule that is expressed from a recombinant DNA molecule (e.g. human IL-22 expressed by cells containing a plasmid or virus expressing a human IL-22 gene).

As used herein the term "recombinant DNA molecule" refers to a DNA molecule that is comprised of segments of DNA joined together by means of molecular biological techniques (e.g. a human IL-22 gene ligated into a plasmid DNA sequence or viral sequence).

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "gene" refers to a nucleic acid (e.g., DNA) sequence that comprises coding sequences necessary for the production of a polypeptide or precursor. It is intended that the term encompass polypeptides encoded by a full length coding sequence, as well as any portion of the coding sequence, so long as the desired activity and/or functional properties (e.g., IL-22 activity, ligand binding, enzymatic activity, etc.) of the full-length or fragmented polypeptide are retained. The term also encompasses the coding region of a structural gene and the sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as "5' untranslated sequences." The sequences that are located 3' (i.e., "downstream") of the coding region and that are present on the mRNA are referred to as "3' untranslated sequences."

The term "gene" encompasses both cDNA and genomic forms of a gene. A genomic form of a genetic clone contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "polymerase chain reaction" ("PCR") refers to the methods described in U.S. Pat. Nos. 4,683,195, 4,683,202, and 4,965,188, herein incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified." In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications. With PCR, it is possible to amplify a single copy of a specific target sequence in genomic DNA to a level detectable by the device and systems of the present invention.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "reverse-transcriptase" and "RT-PCR" refer to a type of PCR where the starting material is mRNA. The starting mRNA is enzymatically converted to complementary DNA or "cDNA" using a reverse transcriptase enzyme. The cDNA is then used as a "template" for a "PCR" reaction.

As used herein, the term "real-time polymerase chain reaction" or "quantitative polymerase chain reaction" or "qPCR" refers to measuring changes in mRNA for determination of levels of specific DNA or RNA sequences in tissue samples. It is based on detection of a fluorescent signal produced proportionally during amplification of a PCR product. For example, Real-Time PCR measuring mRNA is done using a Tagman™ method of quantitative RT-PCR for measurement of changes in mRNA using the Perkin Elmer/Applied Biosystems Division 7700 Sequence Detector.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer should be sufficiently long to prime the synthesis of extension products in the presence of the inducing agent. The exact lengths of the primers will depend on many factors, including temperature, source of primer and the use of the method.

As used herein, the term "sample template" refers to nucleic acid originating from a sample that is analyzed for the presence of "target" such as IL-22 produced in intestinal cells. In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

BRIEF DESCRIPTIONS OF THE DRAWINGS

FIGS. 1A-1F. Absence of host-derived IL-22 increases mortality after allo-BMT/HCT. A, KO recipients, minor antigen mismatch. B, KO recipients, MHC mismatch. C, Anti-IL-22 neutralizing antibody, MHC mismatch. D, KO marrow, MHC mismatch. E, KO donor T cells, MHC mismatch. F, Hematopoietic KO recipients, minor antigen mismatch with reduced intensity BMT (3 months after hematopoietic chimeras were generated by reconstituting WT B6 mice with IL-22 KO or WT congenic CD45.1 B6 marrow). Data representative (D) or combined from 2-4 independent experiments.

FIGS. 2A-2G. A, GVHD score of LP→B6 BMT/HCT with WT or IL-22 KO recipients. (n=4-5 BM without T cells and 10 BM+T mice/group). B, ELISA of supernatants from small and LI organ cultures 2 weeks after B6→BALB/c BMT. C, qPCR of lamina propria cells 2 weeks after B10.BR→B6 BMT. D, ELISA of thymus 2 weeks after sublethal radiation without BMT or B6→BALB/c BMT. E, Serum IL-22 after allo-BMT with or without GVHD. F, ELISA on intestinal homogenates from B6 mice (combined from two experiments). G, Host CD45$^+$CD3$^-$RORγt$^+$ cells from SI lamina propria 2 weeks after B6→BALB/c BMT, stimulated with IL-23 in vitro, representative of 3 independent transplants.

FIGS. 3A-3G. A, SI crypt schematic. B-C, IL-22R staining: brackets indicate progenitors, green arrows indicate ISC, and red arrows or red IF indicate Paneth cells. B, IL-22R IHC. C, IF for IL-22R (green), Paneth cell lysozyme (red), and nuclei (blue). D-G, LP→B6, 3 weeks post-BMT/HCT. D, Lgr5-LacZ recipients. Lgr5 marks CBC/ISC, and the β-galactosidase reporter is indicated by dark staining in the crypt base of normal intestine (upper right). This staining, and thus the survival of ISC, is still present in the absence of GVHD (bottom left), but staining and stem cells are significantly lost during GVHD (bottom right). Combined statistics for CBC counts are also shown (upper left). E, Assessment of ISC histologically based on niche location at the crypt bases between Paneth cells in WT or IL-22 KO mice. F, Histologic apoptosis 3 weeks post-BMT/HCT in WT or IL-22 KO recipients. G, Plasma FITC-dextran after oral gavage of WT or IL-22 KO recipients of BM+T cells. FITC-dextran translocation across epithelium into the blood stream indicates loss of barrier integrity. $*p<0.05$, $p<0.01$, $*p<0.001$.

FIGS. 4A-4G. rIL-22 administration decreases gut GVHD pathology and increases ISC recovery, but does not affect Paneth cell recovery or function. LP→B6 3 weeks post-BMT, rIL-22 administration daily starting day 7 post-BMT. A, Decreased gut GVHD pathology after IL-22 administration. B. No observed change was found in skin GVHD after IL-22 administration. C. Decreased crypt apoptosis after IL-22 administration. D. Lgr5-LacZ recipients demonstrated increased recovery of LacZ$^+$ crypt base ISCs after IL-22. E. Paneth cells were decreased in GVHD and were not increased by IL-22 administration. F-G. qPCR of mRNA from small intestine. F, No observed change was found expression of Paneth cell-derived molecules after IL-22. G, Innate antimicrobial genes are increased in GVHD after IL-22 treatment. All data representative or combined from at least two experiments and at least five mice per group. $p<0.01$, $*p<0.001$.

Figure 5A:
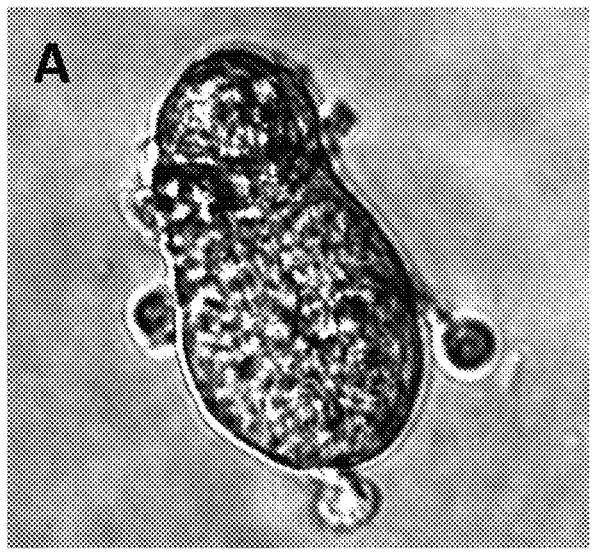
Figure 5B:
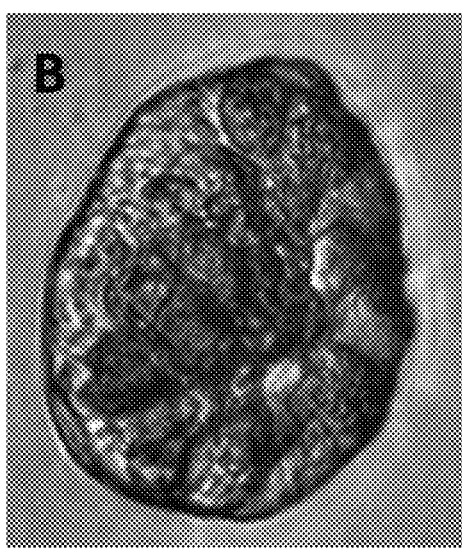
Figure 5C:
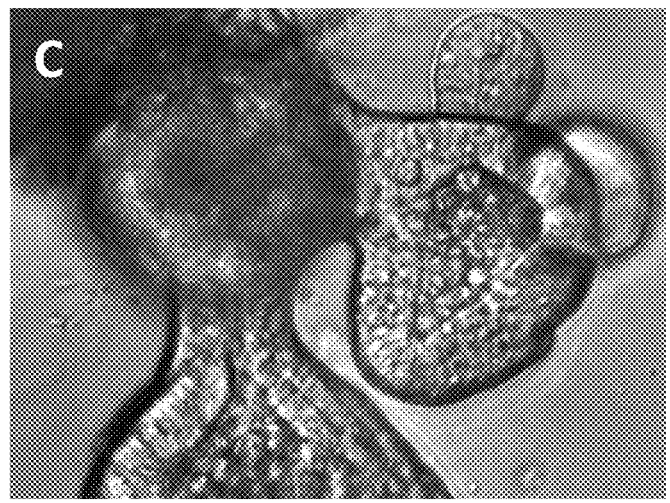
Figure 6A:
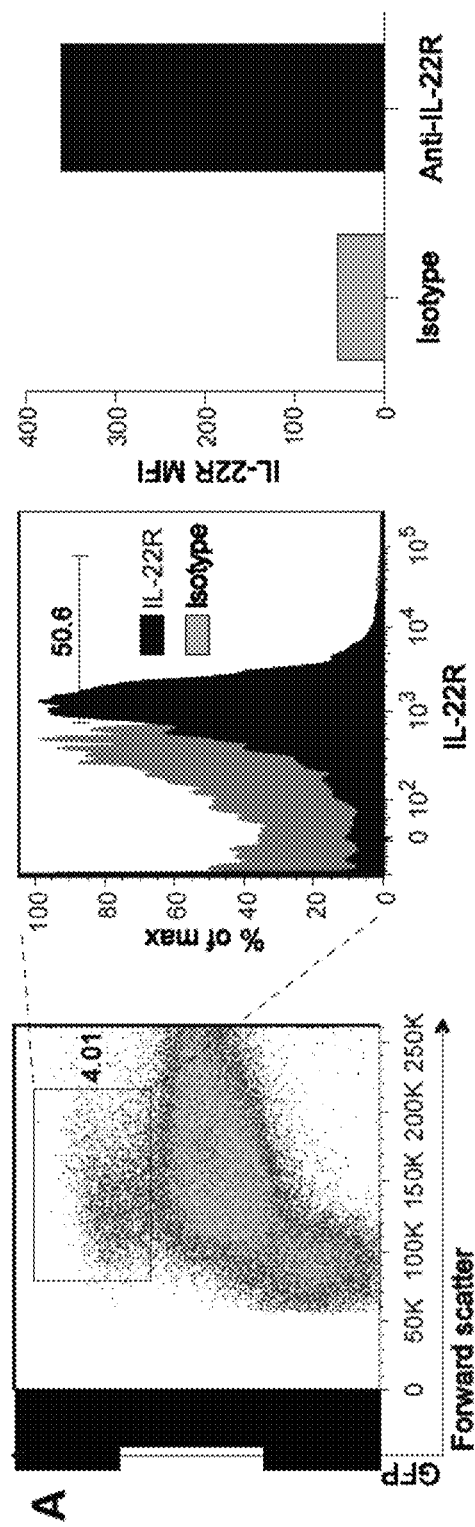
Figure 6B:
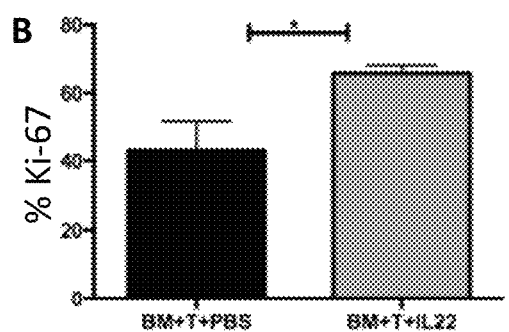
Figure 6C:
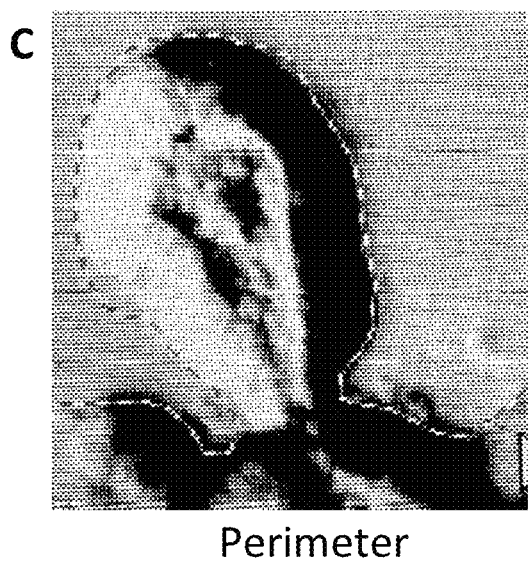
Figure 6D:
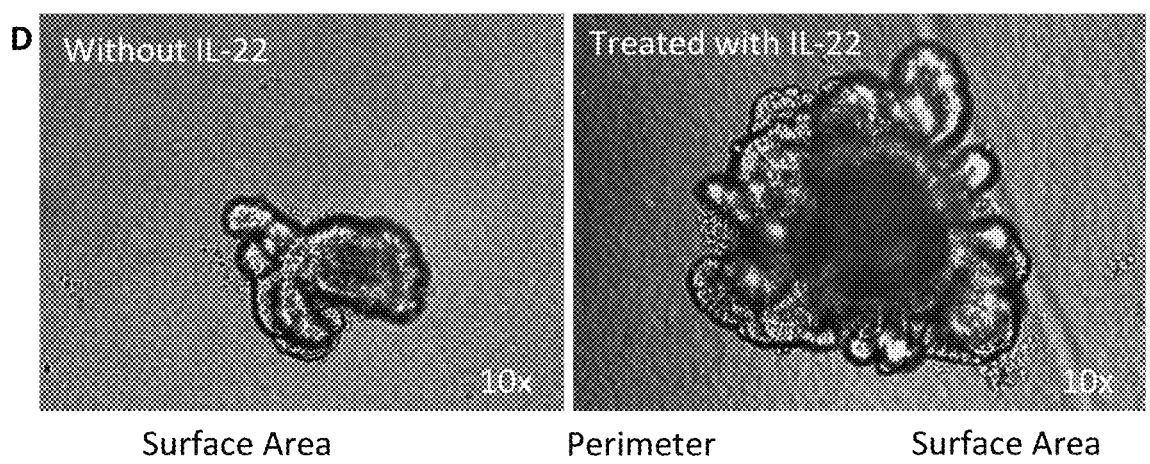
Figure 6E:
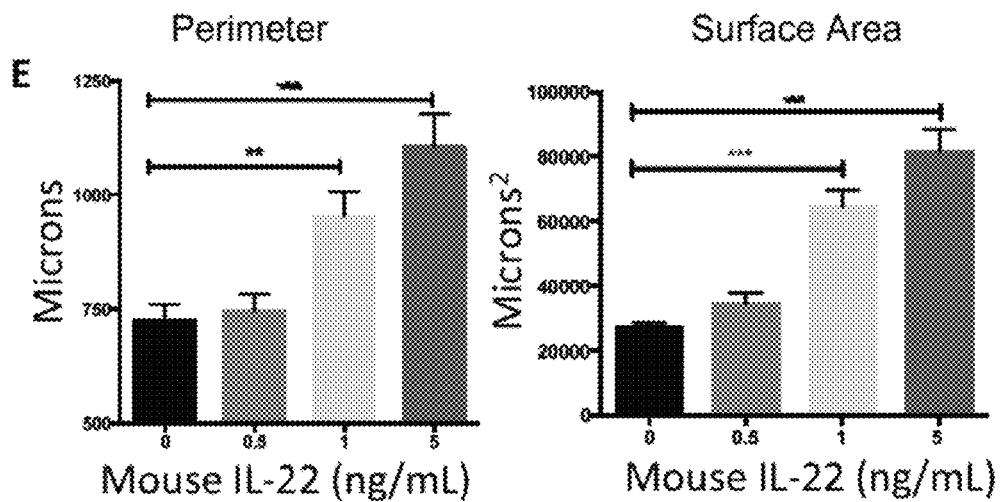
Figure 6F:
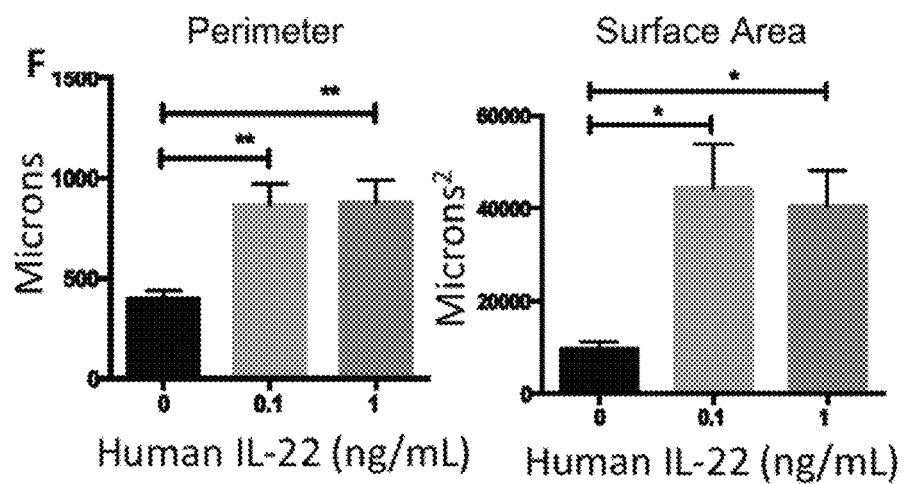

FIGS. 5A-5C. Organoids grown ex vivo from small intestine crypts. Crypts were isolated from B6 small intestine and cultured in matrigel with R-spondin1, EGF, and noggin. A. 1$^{st}$ day of culture, the crypt lumen is starting to close. B. Sphere formation from crypt after 24 hours in culture. C. Organoid with new crypt buds after 7 days in culture.

FIGS. 6A-6F. IL-22 dimer augmentation of ISC function. A. IL-22 receptor expression on SI ISCs isolated from Lgr5-GFP reporter mice: Left panel indicates gating of GFP$^+$ cells, middle and right panels indicate IL-22R expression. B. Increased Ki-67 demonstrating proliferation of Lgr5-GFP$^+$ SI ISCs from reporter mice with GVHD after treatment with IL-22. C. High magnification of in vitro organoid demonstrating perimeter tracing for measurement of organoid perimeter and area. D-E. Increased size of SI organoids after culture with IL-22 for one week. D. Representative images. E. Organoid size after culture with murine IL-22. F. Organoid size after culture with F-652 human IL-22 dimer. $*p<0.05$ $p<0.01$, $*p<0.001$.

FIGS. 7A-7H. IL-22 and innate lymphoid cells increase the growth of intestinal organoids cultured ex vivo. a, Brightfield microscopy of SI organoids after seven days of ENR culture with or without IL-22 (5 ng/ml). b, Microscopic tracing of organoid to measure perimeter and calculate surface area. c-d, Perimeter (microns) and area (microns$^2$) of the horizontal plane through the organoids cultured with 0-5 ng/ml rmIL-22 for seven days: c, SI; d, LI. e, IL-22 increased new crypt formation (budding) of SI (day 4) and LI (day 7) organoids. f-g, Size (perimeter and surface area) of SI (f) and LI (g) organoids cultured in the presence of human IL-22 dimer F-652. h, Size of SI organoids cultured in Matrigel with ENR+/−IL-2, IL-15, IL-7, and IL-23 in the presence or absence of SI LCs (crypt:LC ratio=1:3). Data combined or representative of at least two independent experiments. * p<0.05;  p<0.01; * p<0.001.

Figure 8A:
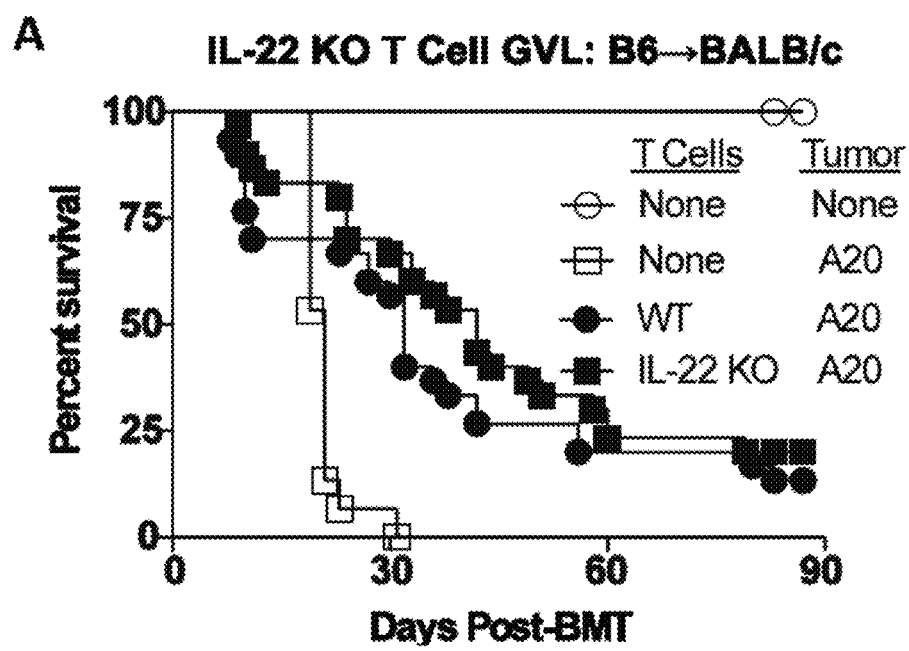
Figure 8B:
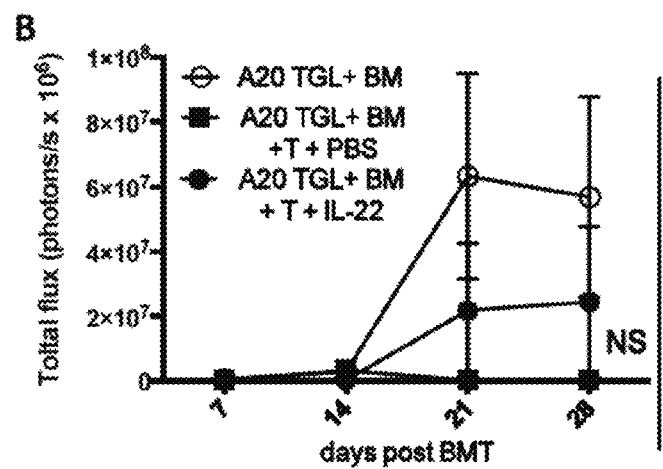
Figure 8B:
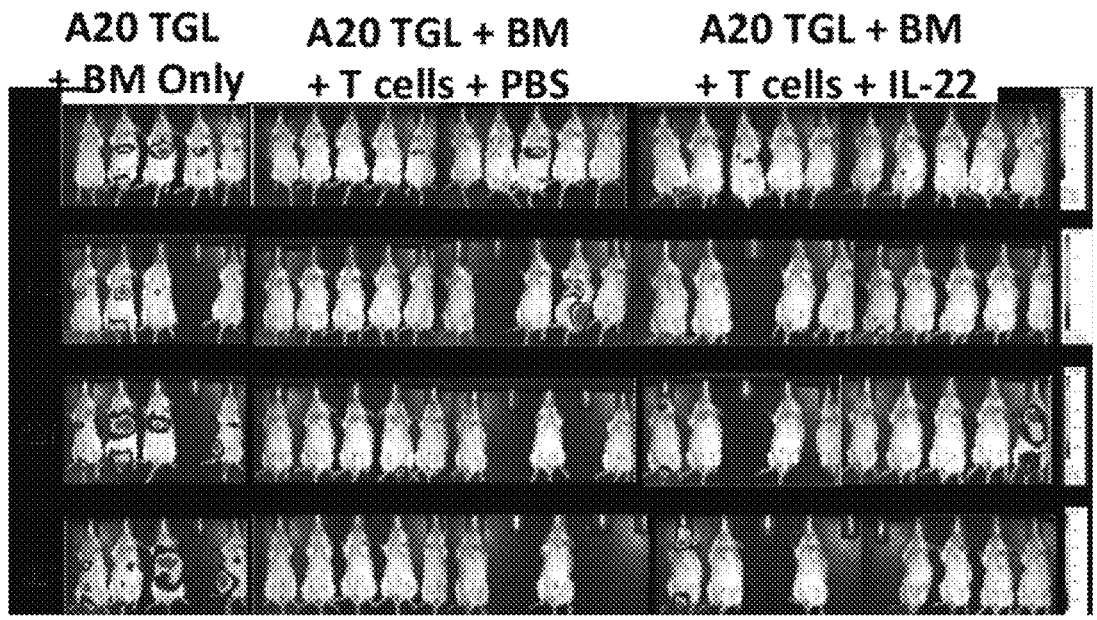
Figure 8C:
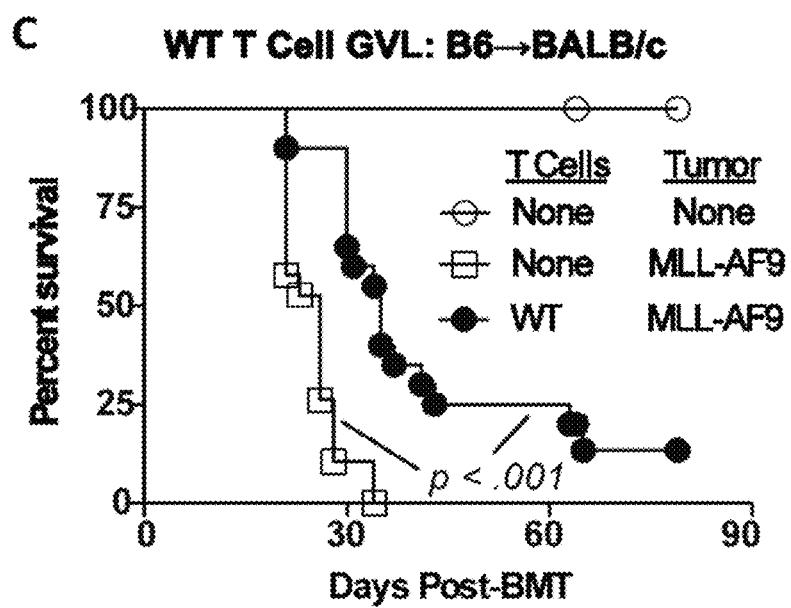

FIGS. 8A-8C. GVL models. A-B. GVL against A20 lymphoma. A, WT vs. IL-22 KO donor T cells. Donor T cell IL-22 was not observed to affect GVL against A20 lymphoma. Survival was equivalent in recipients of WT and IL-22 KO T cells after tumor challenge with A20. B, WT T cells and daily IP PBS vs. rIL-22. IL-22 administration was not observed to interfere with GVL against luciferase$^+$ A20 (A20 TGL) as evidenced by tumor bioluminescence. C. Potential alternative GVL model: MLL-related leukemia. Donor T cells mediate GVT against AML generated by lentiviral transduction with MLL-AF9 fusion construct. HCT with MLL-AF9 leukemia. Shown is a B6→BALB/c BMT with MLL-AF9 leukemia. AML was generated by transducing BALB/c BM with the MLL-AF9 construct and was then transferred to secondary recipients for testing GVL.

Figure 9:
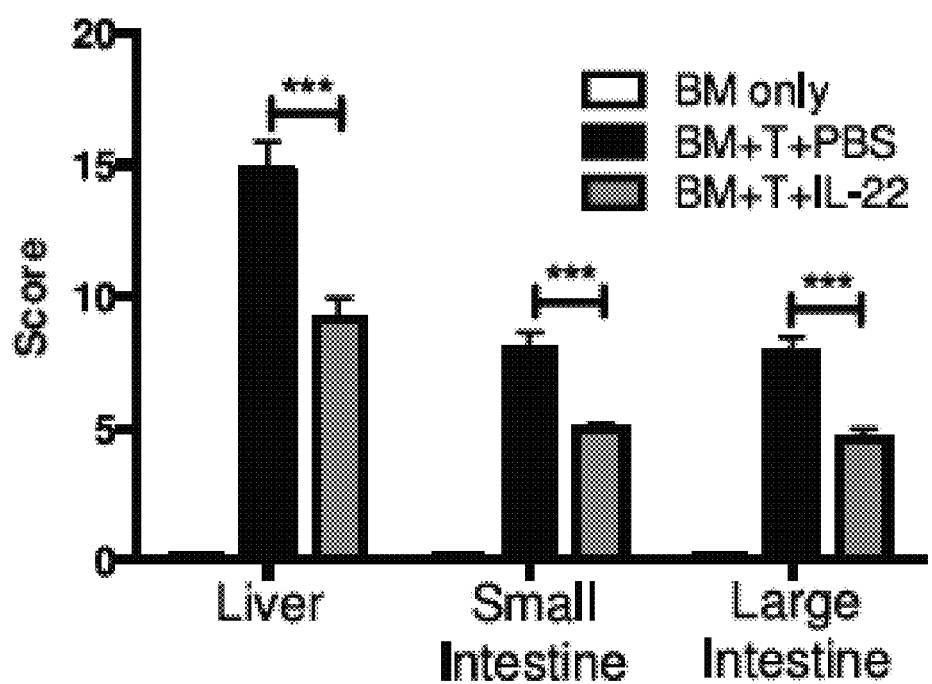

FIG. 9. Daily IP administration with rIL-22 protein. Decreased GVHD pathology was observed in recipient small intestine, large intestine, and liver three weeks post-HCT. LP→B6 BMT GVHD histopathology 3 weeks post-transplant with IL-22 administration. p<0.001.

Figure 10:
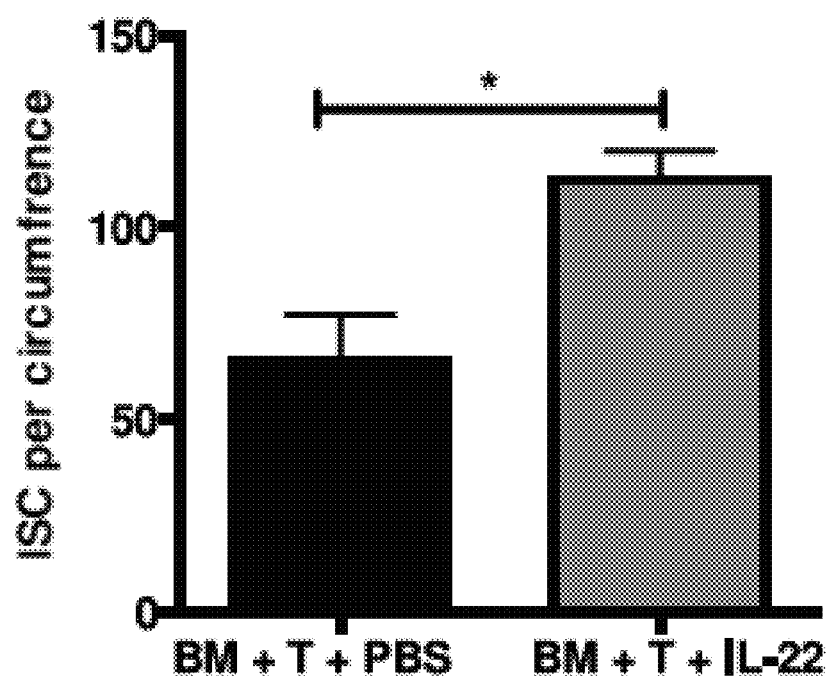

FIG. 10. Recipients treated with rIL-22 protein. Increased numbers of Lgr5+ ISC were present three weeks post-HCT during active GVHD with no observed immunosuppression. Lgr5+ intestinal stem cells 3 weeks post-transplant with rIL-22 administration. p<0.05.

Figure 11:
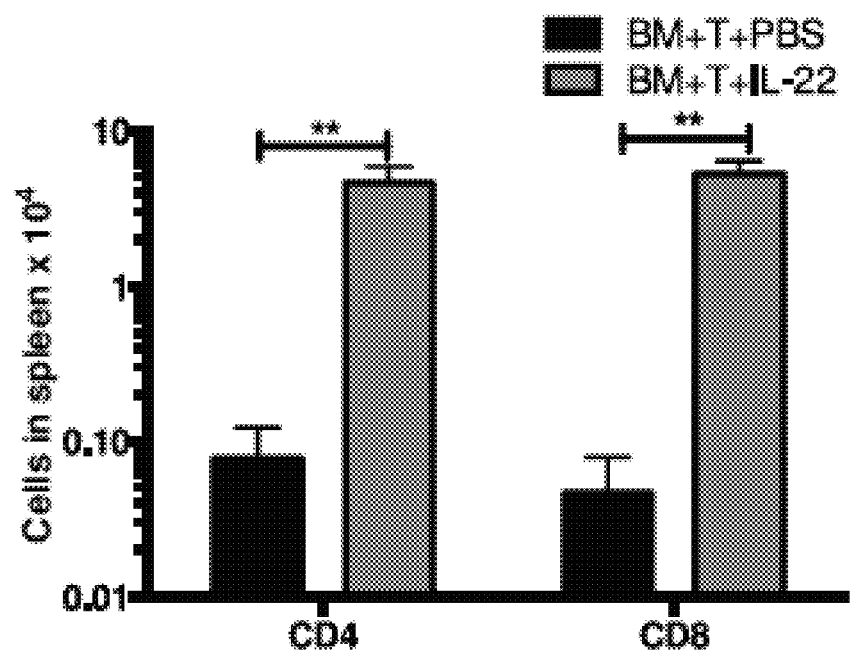

FIG. 11. FVB into BALB/c MHC-mismatched transplant with Rag2-GFP marrow and WT T cells. rIL-22 protein administration increased the development of donor marrow-derived CD4 and CD8+ thymic emigrants four weeks post-HCT. Marrow-derived T cells 4 weeks post-transplant with rIL-22 administration. p<0.01.

FIGS. 12A-12E. IL-22 administration post-HCT. LP☐B6. (A-B) 3 weeks post-HCT after daily rIL-22 IP administration of IL-22, BM without T cells (white), BM+T cells+PBS IP (black), BM+T cells+IL-22 (gray): A, intestinal GVHD pathology score B, intestinal crypt apoptosis score. C, IL-22 ELISA after *lactobacillus* culture in vitro, left bar is lacto-22s. D, IL-22 FACS of IL-22-surface-anchored *lactobacillus* with (pink) or without (blue) pH adjustment, and negative control *lactobacillus* (green). E, Survival (left) and GVHD score (right) after HCT with daily lacto gavage, BM without T cells (black, circles), BM+T+PBS (black, squares), BM+T cells+lacto-WT (green), BM+T cells+lacto-22s (red), BM+T cells+lacto-22a (blue). *p<0.05, ***p<0.001.

Figure 13:
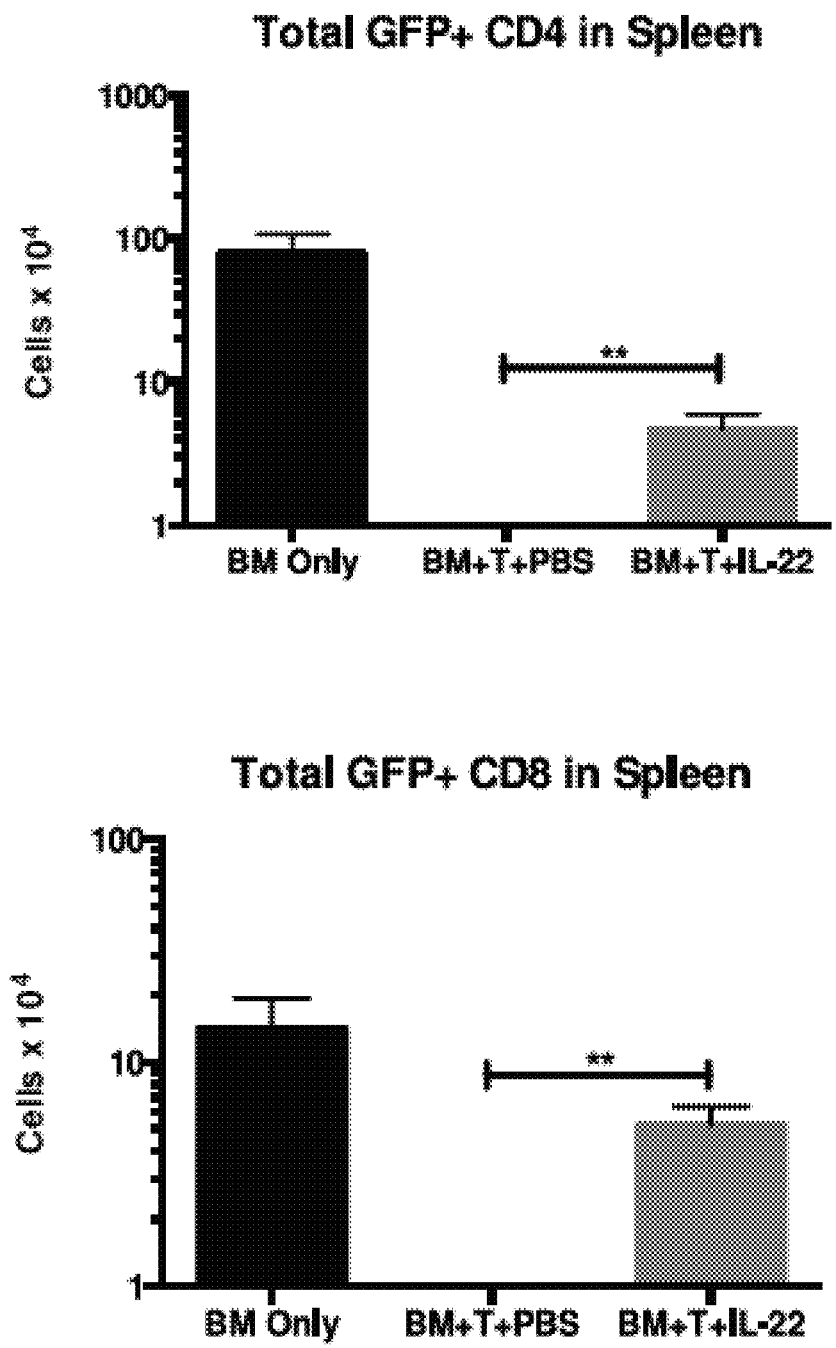

FIG. 13. IL-22 administration decreases GVHD pathology. LP into B6, 3 weeks post-BMT. IL-22: 4 ug daily starting day +7. ***=p<0.001

Figure 14:
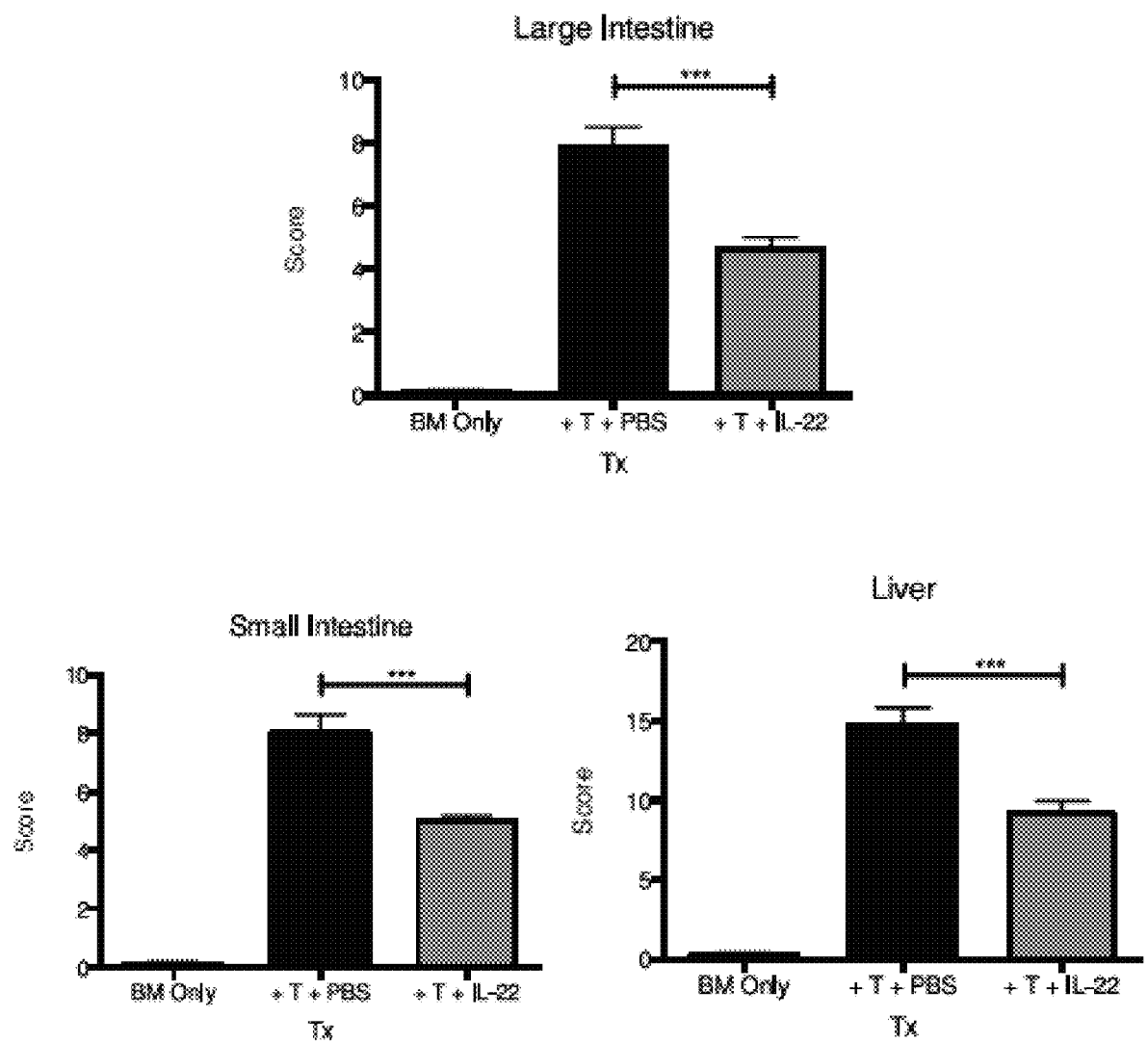

FIG. 14. IL-22 administration decreases crypt apoptosis. LP into B6, 3 weeks post-BMT. IL-22: 4 ug daily starting day +7. ***=p<0.001

Figure 15:
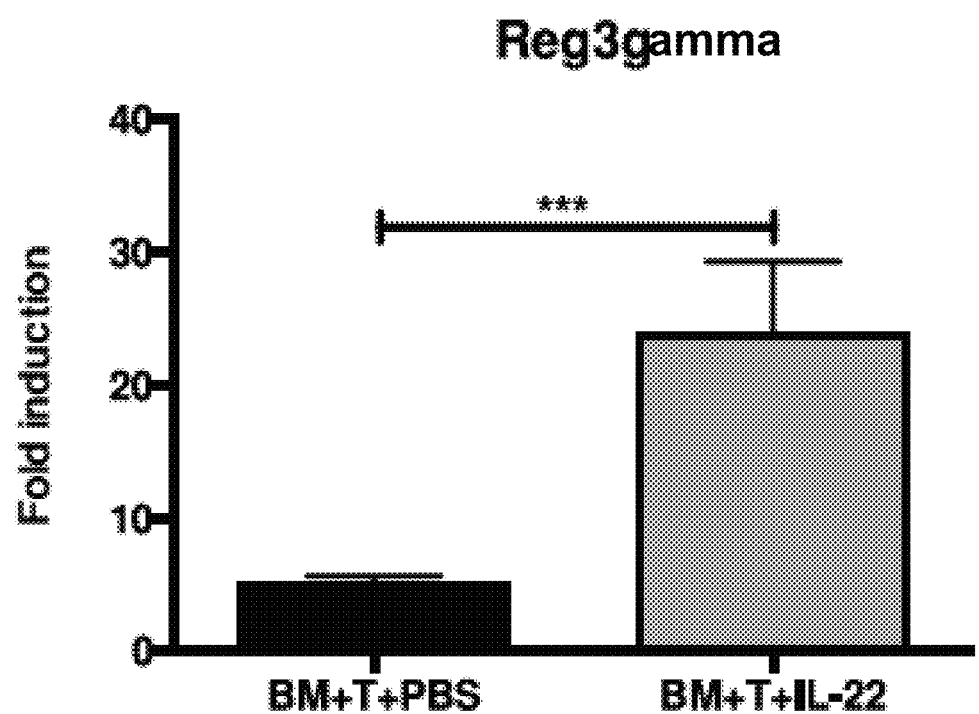

FIG. 15. IL-22 administration increases expression of innate antimicrobials. LP into B6. 3 weeks post-BMT.

FIGS. 16A-16J. IL-22 activates STAT-3 signaling within organoids and augments ISC regeneration. a-b, qPCR for relative expression of Wnt3, β-catenin, and Axin 2 genes of the Wnt/β-catenin axis (a), as well as mRNA for Reg3β and Reg3γ innate anticmicrobials (b) in SI organoids cultured with 0, 1 or 5 ng/ml rmIL-22. Data combined from three independent experiments. c, Intracellular staining of phospho-STAT3 (Y705) in organoid cells cultured under ENR conditions followed by a 20 minute pulse of 20 ng/ml IL-22, evaluated by flow cytometry. d, Brightfield images and surface area measurements of SI organoids four days after crypt culture with ENR+/−STAT3 inhibitor Stattic. e, IL-22 induced phospho-STAT3 (Y705) activation in Lgr5-GFP+ cells. f-g, Single Lgr5-GFP+ ISCs from SI were cultured into organoids in the presence or absence of rmIL-22 (1 ng/ml). f, IL-22 increased organoid budding (culture day 4). Representative images of early budding are shown in ascending order. * indicates an early organoid with no budding. ▲ indicates polarization prior to budding. ↑ indicates budding at a site of polarization. g, IL-22 also increased organoid size in cultures starting from single stem cells (culture day 13). h, IL-22 (1 ng/ml) led to increased incorporation of EdU into SI organoid crypts. i, IL-22 (1-5 ng/ml) increased the number of Lgr5-GFPhigh SI ISCs. j, Serial passaging demonstrated that increased numbers of organoids could be generated after culture with IL-22 (1 ng/ml). c-j are combined or representative of at least two independent experiments. * p<0.05;  p<0.01; * p<0.001.

FIGS. 17A-17E. IL-22 reduces intestinal tissue pathology without substantially altering alloreactive immunity. B6 recipient mice were transplanted with LP T cell-depleted bone marrow alone or with LP bone marrow and T cells (H-2b→H-2b) to induce GVHD and treated daily with PBS or 4 ug rmIL-22 by IP injection. a-b, Histopathologic assessment was performed on intestinal tissues three weeks after BMT. a, Bar graphs show scoring of GVHD and apoptosis. b, Representative haematoxylin and eosin staining of intestines from mice treated with PBS or IL-22. Arrows indicate apoptotic cells within the intestinal epithelium. c, Splenocytes from recipients were analyzed with flow cytometry three weeks after BMT, indicating frequencies of donor T cells subsets, expression of activation marker CD25, and expression of gut homing molecule α4β7 integrin. d, Expression of inflammatory cytokines in spleen and small intestine were analyzed in recipient tissues three weeks post-BMT. e, IL-22 administration increased expression of Reg3β and Reg3γ mRNA in small intestine three weeks post BMT. Data combined or representative of two independent experiments with at least nine mice per group.  p<0.01; * p<0.001.

FIGS. 18A-18I. IL-22 directly increases Lgr5+ISCs in vivo independent of the ISC niche. a-f, LP→B6 BMT (H-2b→H-2b)+/− T cells; recipients were treated daily with PBS or 4 ug rmIL-22 IP starting day seven after BMT. Data are combined from two independent experiments with at least seven mice per group. a, LP→B6 BMT was performed with Lgr5-LacZ reporter mice as recipients. Small intestine Lgr5+ CBC ISCs were assessed three weeks post-BMT (after two weeks of daily PBS or rmIL-22). b, LP→B6 BMT with Lgr5-GFP reporter mice as recipients. GFP+ ISCs were evaluated by flow cytometry for expression of Ki-67 fourteen days post-BMT (after one week of daily PBS or rmIL-22). c, Numbers of lysozyme-positive Paneth cells per small intestine crypt three weeks post-BMT. d, Relative expression (qPCR) of WNT3 and EGF mRNA from small intestines of mice with GVHD three weeks post-BMT. e, Paneth cell IL-22R expression and STAT3 phosphorylation assessed by flow cytometry. Shown are gating of Paneth cells based on side scatter and CD24 expression (left panel), Paneth cell IL-22R expression at baseline and five days after 1200 cGy total body irradiation (middle panel), and STAT3 phosphorylation in organoid-derived Paneth cells after a 20 minute pulse of 20 ng/ml IL-22 (right panel). f, Relative expression (qPCR) of R-spondin-3 mRNA from small intestines of mice with GVHD three weeks post-BMT. g, Relative expression (qPCR) of Wnt-activated genes β-catenin and Axin 2 in crypts isolated from small intestines of mice with GVHD three weeks post-BMT. h-i, Mice were treated subcutaneously with PBS or 100 ug/kg F-652 every other day for 10 weeks starting one week after LP→B6 BMT. Recipient mice were monitored for clinical signs of GVHD (h) and GVHD-related mortality (i). * p<0.05;  p<0.01; * p<0.001.

Figure 19:
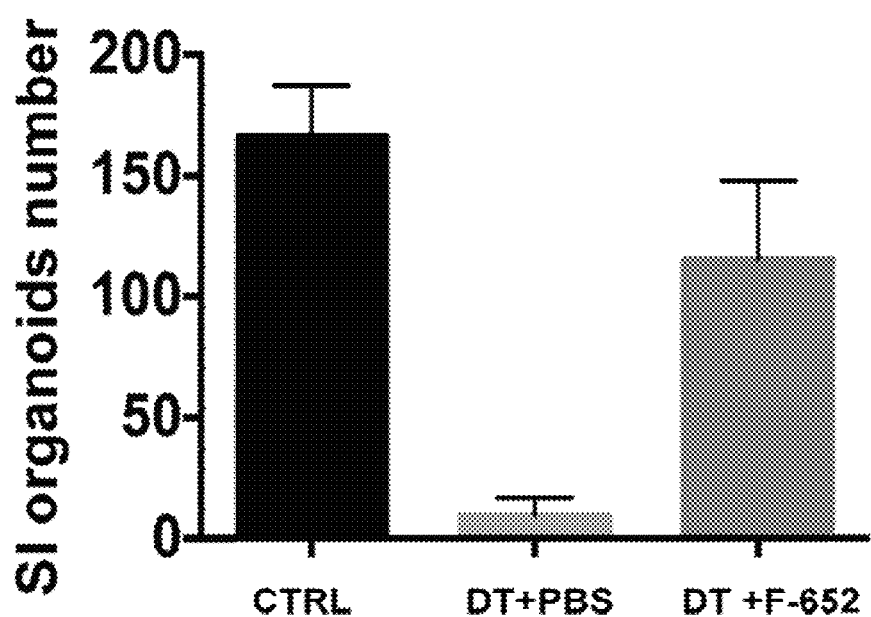
Figure 20A:
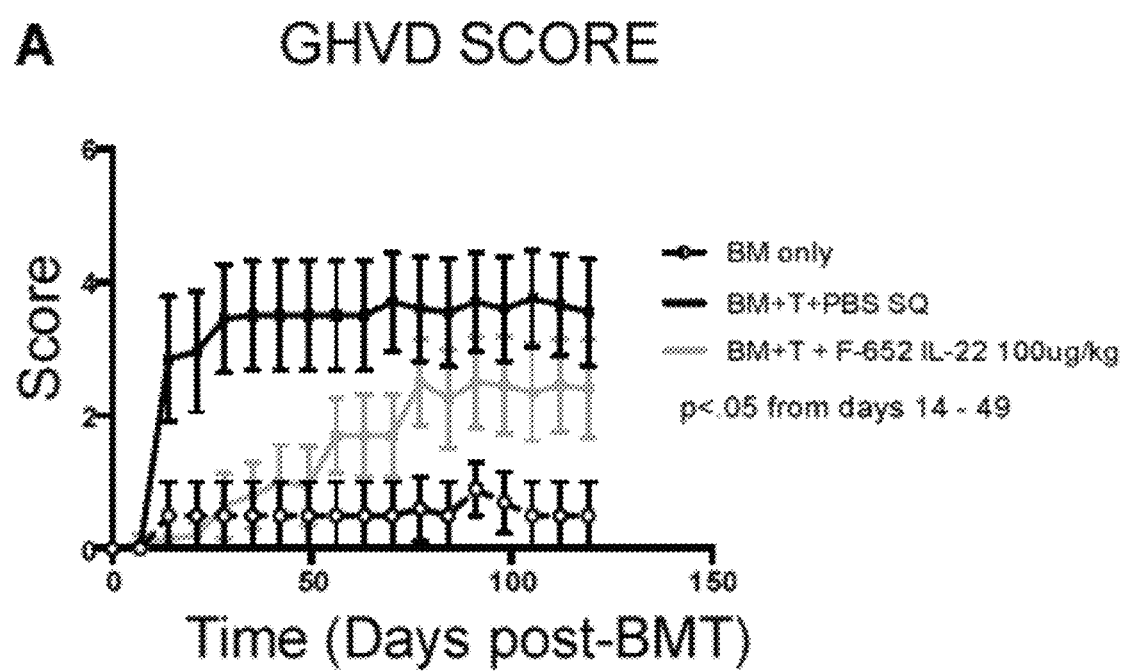
Figure 20B:
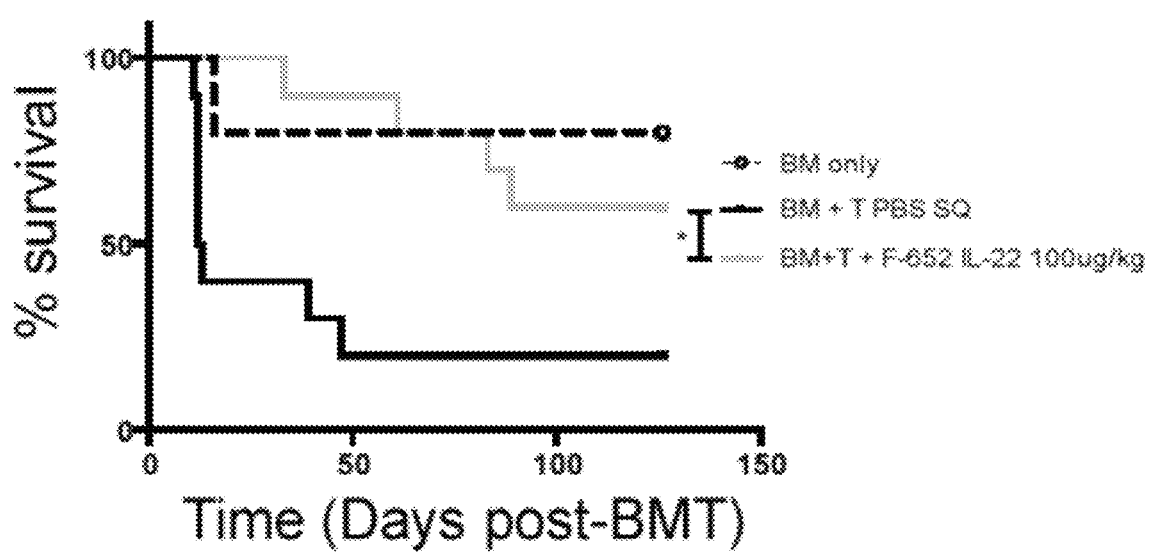
Figure 20C:
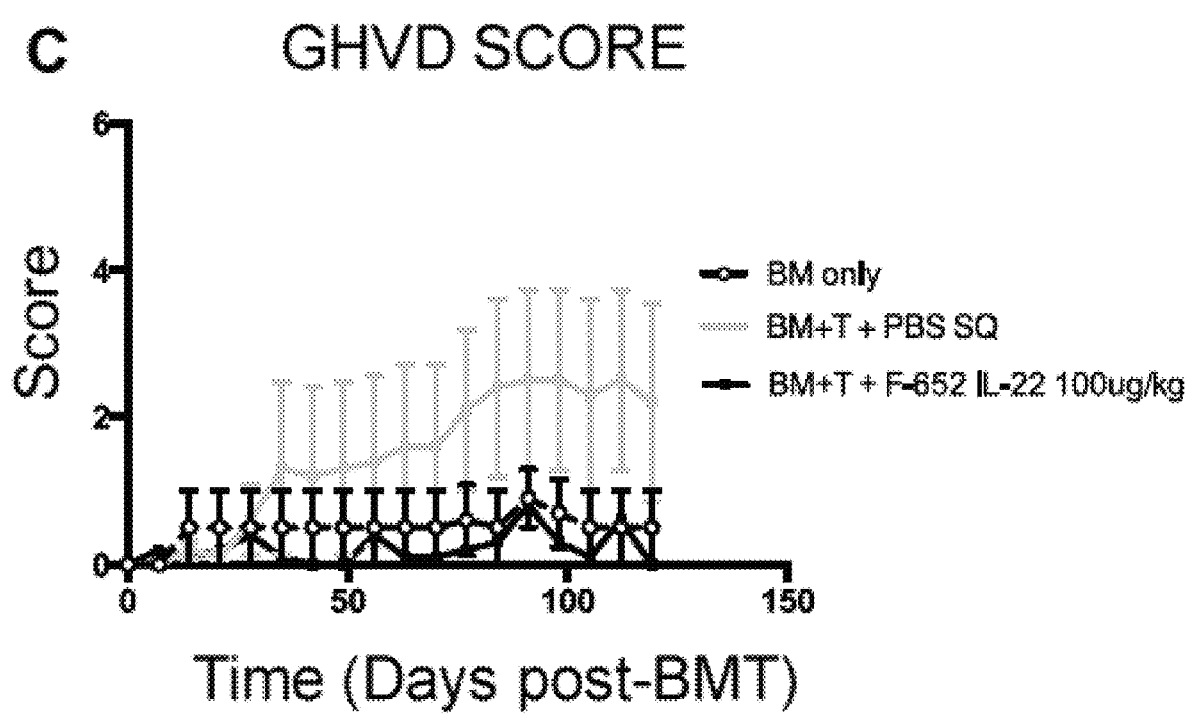
Figure 20D:
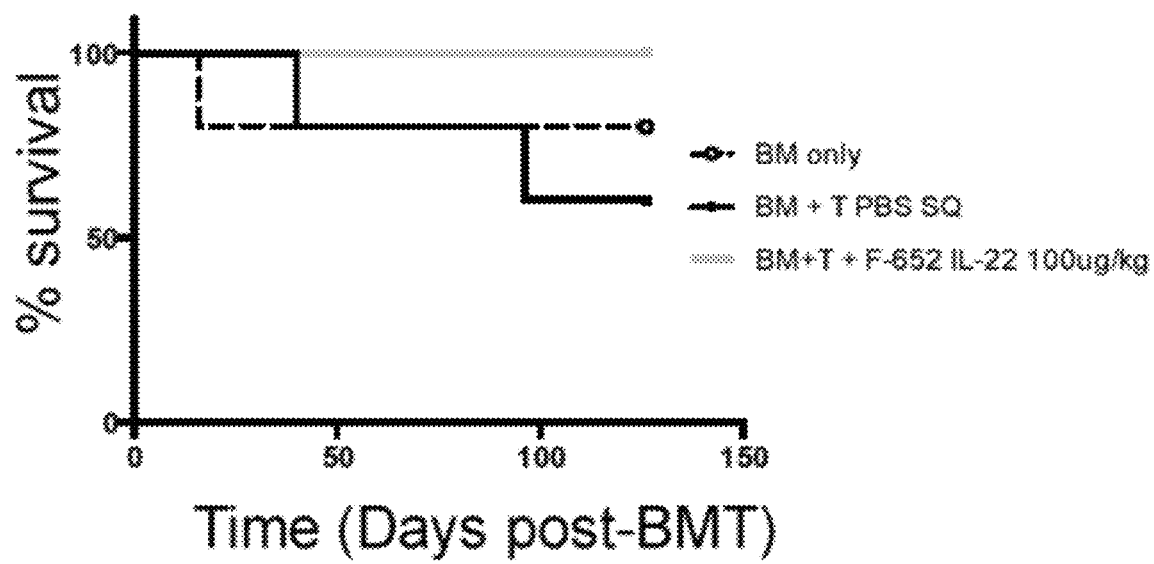

FIG. 19. F-652 treatment reduces the severity of FOX3P deletion. T-reg deletion after diptheria toxin (DT) treatment (50 ug/Kg) of FOX3P-DTR mice leads to systemic autoimmunity, including gastrointestinal autoimmunity. This disrupts crypt homeostasis and negatively affects the intestinal stem cell compartment as evidenced by impaired organoids growth from small intestine (SI). SI crypts were harvested eight days after DT treatment. When compared with DT alone (+PBS), administration of F-652 (100 ug/KG) every other day (after DT treatment) protects the ISC compartment from T-regablation, as evidenced by the increased number of organoids observed after 7 days in culture. For each determination, 20 randomly selected fields from four independent culture were analyzed and values are expressed as mean +SD. *p<0.01 vs CTRL (Anova one Way). **p<0.05 vs DT+F-652 (Anova one Way). CTRL: control, DT: diphtheria toxin.

FIGS. 20A-20D. F-652 treatment improves overall survival and reduces systemic markers of GVHD in vivo. Experimental design: LP→B6 MHC matched allogeneic bone marrow transplant model, 1100 cGy XRT split dose, 5×10^6 TCD BM cells, 4×10^6 CD5+ T cells for the BM+T cell groups then treated either with subcutaneous PBS or F-652 at a dose of 100 μg/kg every other day. A-B experiments were a MHC-matched allogeneic bone marrow transplant model with 10 mice per group in each of the treatment groups, 5 in the bone marrow only control. These mice started treatment with F-652 or PBS seven days post bone marrow transplant. Then these mice were given subcutaneous shots every other day for ten weeks with F-652 at a dose of 100 μg/kg or with PBS. A: systemic GVHD score for experiment where treatment started seven days post-BMT. B: overall survival for experiment where treatment started seven days post-BMT. * indicates p<0.05. C-D experiments were a MHC-matched allogeneic bone marrow transplant model with 5 mice per group in each of the groups receiving treatment with F-652 or PBS only after systemic GVHD symptoms started to develop (four weeks post-BMT). Then these mice were given subcutaneous shots every other day with F-652 at a dose of 100 μg/kg or with PBS. C: systemic GVHD score for experiment where treatment was started only after mice exhibited GVHD symptoms. D: overall survival for experiment where treatment was started only after mice exhibited GVHD symptoms.

DESCRIPTION OF THE INVENTION

The present invention provides methods and compositions for the use of IL-22 for treating conditions of intestinal injury and inflammatory conditions such as graft vs. host disease. Specifically, IL-22 can be used to increase Intestinal Stem Cell (ISC) recovery and for enhancing immune reconstitution following allogeneic hematopoietic transplantation. In particularly preferred embodiments, the present invention provides methods of using therapeutic IL-22, including a dimeric form of IL-22, in therapeutic compositions for treating graft vs. host disease, including affected cells such as hepatic, thymic, gastrointestinal, or other graft vs. host disease effects in hematopoietic stem cell transplant patients and in patients with inflammatory intestinal conditions.

The use of IL-22 was reported for use in the treatment of human diseases, such as pancreatic disease (for example, U.S. Pat. No. 6,551,799, herein incorporated by reference in its entirety) and viral hepatitis including for promoting hepatocyte survival and proliferation (for example, United States Patent Application 20130171100, herein incorporated by reference in its entirety). However IL-22 is not currently used as a treatment for human GVHD. In fact, the inventors found that treatment of GVHD with donor T cells engineered to produce IL-22 may cause undesirable effects such as increased skin GVHD.

An IL-22 for use in practicing the method of the present invention can not only be generated using recombinant DNA technology, but can also be produced through fusion of heterologous polypeptides. A description of other methods, vectors and host cells for synthesis of an IL-22 for use in practicing the method of the present invention can be found in Gething et al., Nature, 293:620-625; Mantei et al., Nature, 281:40-46; EP117,060 and EP117,058. Recombinant IL-22, dimers and fusion proteins thereof are produced using methods known to those of skill in the art. For more details, see U.S. published application no. 2013/0171100, the contents of which are hereby incorporated by reference into the present disclosure.

DNA sequences encoding an IL-22 dimer or fusion protein can be entirely synthesized artificially. Alternatively, DNA encoding IL-22 can be obtained by PCR amplification or synthesis and then joined together to form a DNA sequence encoding an IL-22 dimer.

Briefly, suitable host cells are transformed or transfected with an IL-22 expression vector in accordance with known methods and subsequently grown under conditions known to those of skill in the art to promote growth; transfection techniques are described in greater detail in, for example, Molecular Cloning: a Laboratory Manual 3rd edition, J. F. Sambrook and D. W. Russell, ed. Cold Spring Harbor Laboratory Press 2001.

Host cells suitable for expression of IL-22 are also known in the art and include invertebrate cells, such as insect cells, and mammalian cells. Suitable mammalian cells include Chinese Hamster Ovary (CHO), COS cells; in particular, SV40-transformed monkey kidney CV1 cell line (COS-7, ATCC CRL 1651); human embryo kidney cell line 293 (Graham et al., J. Gen Virol., 36:59 (1997)); CHO/−DHFR (Urlaub and Chasin, Proc. Natl. Acad. Sci. USA, 77:4216 (1980)); murine testis trophoblastic cells (TM4, Mather, Biol. Reprod., 23:243-251) (1980)); human lung cells (W138, ATCC CCL 75); human liver cells (Hep G2, HB 8065); murine breast cancer cells (MMT 060562, ATCC CCL51).

A nucleic acid comprising a nucleotide sequence encoding IL-22 can be inserted into a replicable vector for gene cloning or protein expression. Many vectors for protein expression are known in the art. Using these techniques, a nucleic acid sequence encoding IL-22 is inserted into an appropriate vector, which may further include any of the following: one or more signal sequences, an origin of replication, one or more reporter genes, an enhancer element, a promoter, and a transcription termination sequence.

Methods of transfecting eukaryotic cells and transforming prokaryotic cells are also known to those of skill in the art, and may include the use of calcium chloride, calcium phosphate precipitation, lipofectamine or electroporation. One skilled in the art will be able to select a suitable method depending on the host cell selected.

In one embodiment, a recombinant protein containing human IL-22 and produced in CHO cells in serum-free culture is used.

A pharmaceutical composition for use in practicing the method of the present invention comprises a safe and effective amount of IL-22 or dimer, fusion protein or conjugate thereof and a pharmaceutically acceptable excipient or carrier. "Safe and effective amount" refers to an amount of a compound sufficient to significantly improve the condition of the patient in need thereof, without causing serious side-effects. In general, a pharmaceutical composition of IL-22 comprises 0.001-1,000 mg of IL-22 or its dimer per dose; in one embodiment, the pharmaceutical composition comprises 0.05-300 mg of IL-22 or its dimer per dose; in a further embodiment, the pharmaceutical composition comprises 0.5-200 mg of IL-22 or its dimer per dose.

Pharmaceutically acceptable excipient or carrier are well known to those of skill in the art and may include cellulose and its derivatives (e.g. sodium carboxymethylcellulose, sodium ethylcellulose, cellulose acetate, etc), gelatin, speckstone, solid lubricating agent (e.g. stearic acid, magnesium stearate), calcium sulphate, plant oil (e.g. pea oil, sesame oil, peanut oil, olive oil, etc.), polyols (e.g. propylene glycol, glycerol, mannitol, sorbitol, etc.), emulsifier (e.g. Tween®), wetting agent (e.g sodium lauryl sulfate), colorant, flavoring agent, stabilizer, anti-oxidant, antiseptic, pyrogen-free water, etc.

Routes of administration of IL-22, dimer, fusion protein or conjugate thereof includes oral administration, rectal administration, parenteral administration (intravenous, intramuscular, or subcutaneous), and partial administration.

Allogeneic lymphocytes produce a strong graft-versus-leukemia (GVL) effect, but the beneficial effect is limited by graft-versus-host disease (GVHD). Depletion of T cells abrogated GVHD and GVL effects. Thus in IL-22 knock-out mouse and irradiated mouse models, IL-22 was produced by recipient-derived innate lymphoid cells (ILCs) and contemplated to provide a signal for epithelial recovery following experimental allogeneic hematopoietic cell transplantation (allo-HCT). These IL-22-deficient recipients demonstrated increased GVHD mortality and significantly worse loss of crypt base intestinal stem cells (ISCs) during GVHD. Paradoxically, GVHD also led to reduced gastrointestinal (GI) IL-22 levels in irradiated wild-type (WT) recipients due to the elimination of radioresistant intestinal cells (ILCs). Therefore the inventors were surprised to discover that IL-22 administration after allo-HCT negated (reduced) the effect of ILC elimination and further reduced GVHD pathology without impairing graft versus leukemia (GvL) responses.

Benefits from using IL-22 compositions and methods comprising administering exogenous IL-22 of the present inventions include prophylactic protection and disease recovery of cells from GVHD including but not limited to cells of the small intestine, large intestine and liver.

I. IL-22 Contributions to Intestinal Epithelium Cell Biology and GVHD.

A. In Vivo Epithelial Maintenance Post-Transplant with and without GVHD.

Figures 3A, 3B:
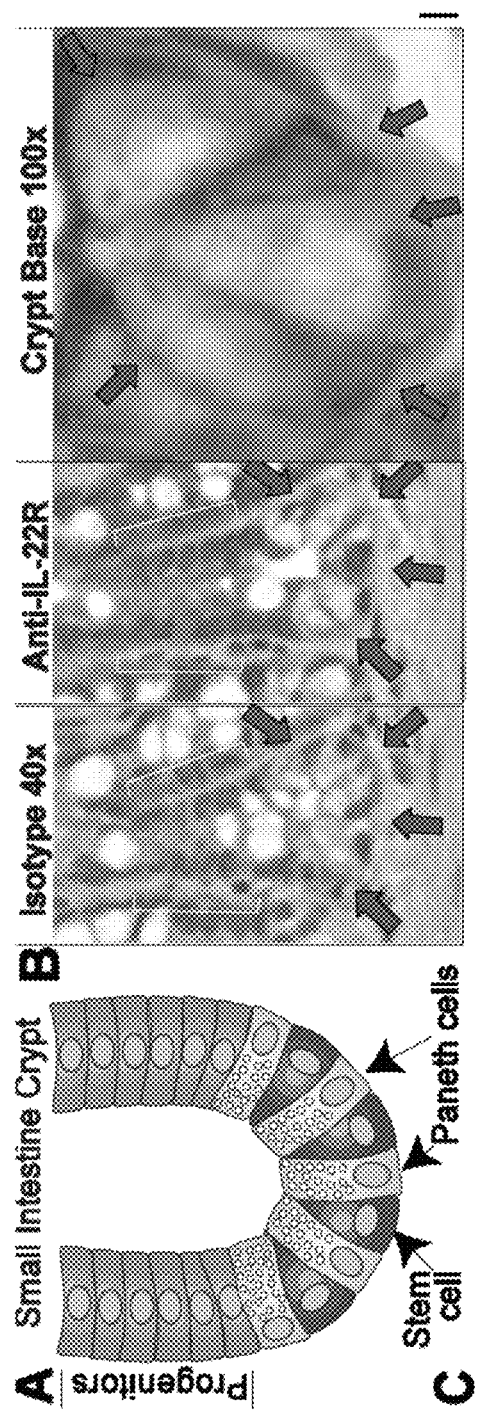
Figures 3C, 3D:
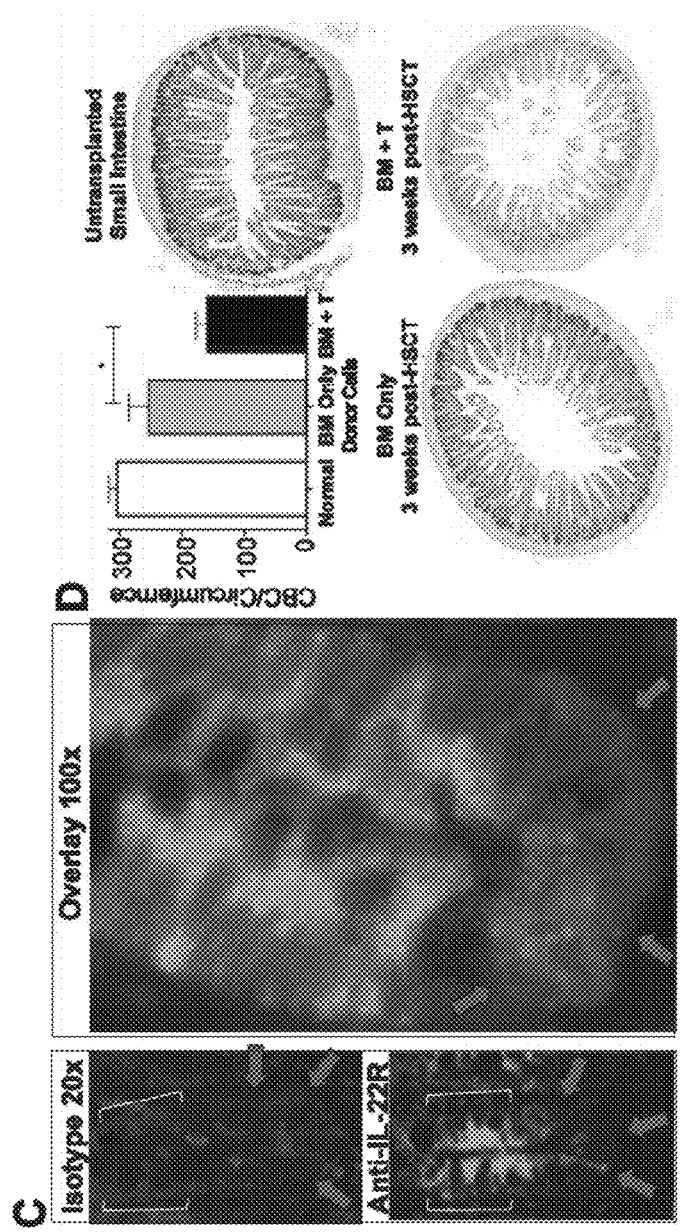
Figures 4A, 4B, 4C:
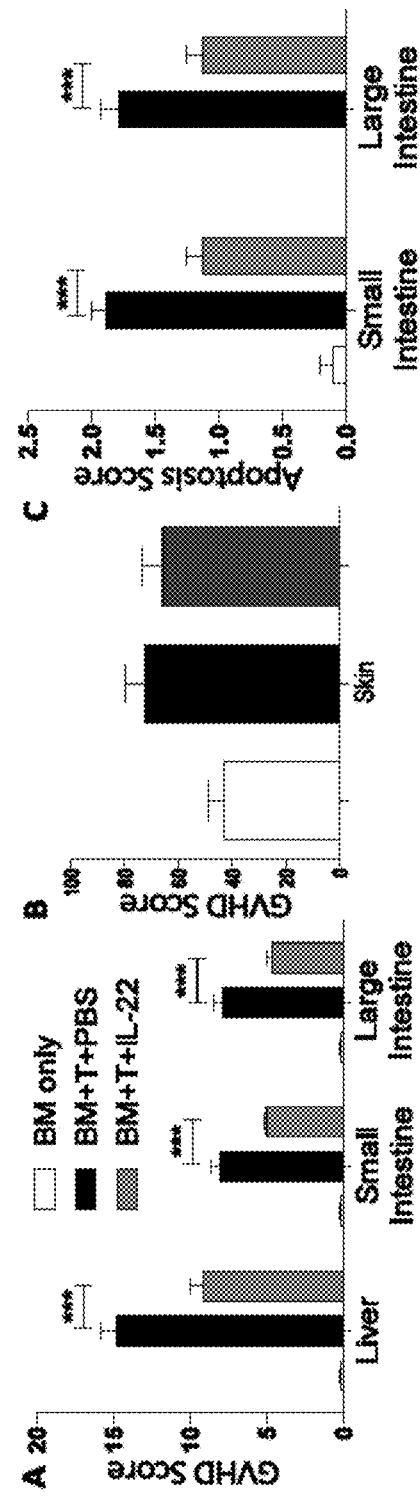
Figure 4D:
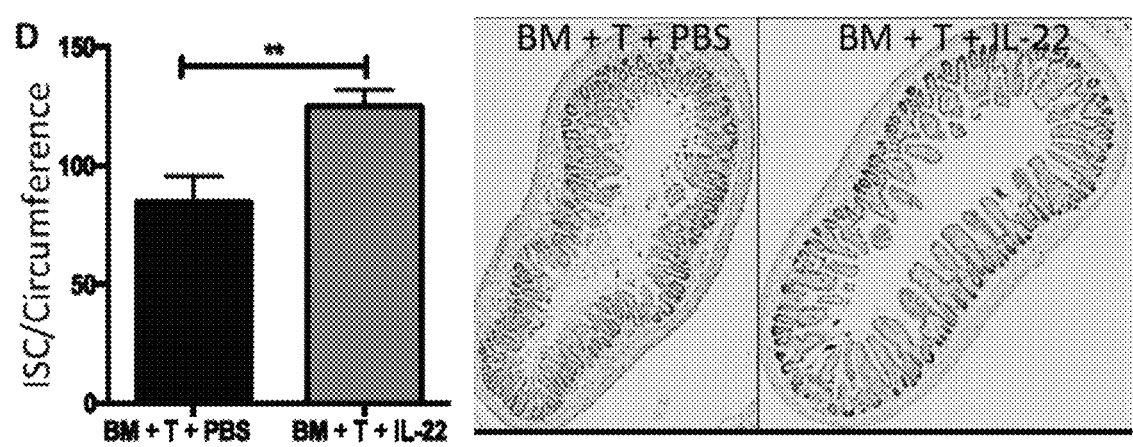
Figure 4E:
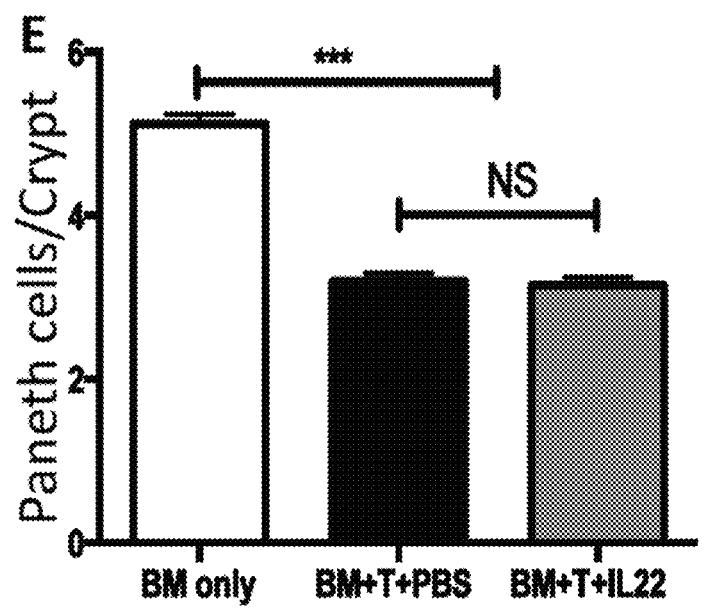

ISC and Paneth cell numbers persist post-transplant in the absence of GVHD however these numbers are reduced in GVHD (FIGS. 3D, 4E). Loss of ISCs in GVHD may be due to the loss of their niche, or the loss of Paneth cells may be due to the loss of their parental ISCs. The villus epithelium of the SI is thought to renew every 3-5 days in normal homeostasis, while Paneth cells are more long-lived, lasting for three weeks or even longer. These kinetics may be altered after tissue damage and in the transplant setting specifically.

1. Epithelial Renewal from $Lgr5^+$ ISCs in Mice without GVHD.

Measurement of the GI expression of molecules involved with ISC and Paneth cell function and kinetics of epithelial renewal. Using C57BL/6 (B6) background inducible Lgr5-LacZ lineage-tracing reporter mice developed in collaboration with colleagues at MSKCC. These mice express a β-galactosidase reporter molecule in $Lgr5^+$ cells and in their progeny after treatment with tamoxifen. By treating recipient mice with tamoxifen on the day of transplant, this will allow for identification of cells in the crypt and villus regenerated from $Lgr5^+$ ISCs post-transplant. Mice will be evaluated for the kinetics of epithelial regeneration from $Lgr5^+$ cells in both the small and LI, and specific attention will be paid in the SI to the kinetics of Paneth cell renewal. Mice will be evaluated 5, 7, and 10 days after a) sublethal (550 cGy×1) and lethal (550 cGy×2) TBI in the absence of transplantation, after b) syngeneic (B6→B6) TCD BMT and after c) syngeneic T cell replete BMT to control for the effects of a) conditioning, b) cellular transplantation, and c) T cell transfer in impacting the kinetics of Paneth cell renewal from ISCs. In addition to lineage tracing, intestinal tissue will be harvested to measure RNA and protein expression of reported ISC genes (Lgr5, BMI-1, Hopx, mTert, Lrig1), Paneth cell genes involved with ISC function (Wnt3, EGF) by quantitative (q)PCR and western blot.

2. Epithelial Renewal, ISC Loss, and Paneth Cell Loss in Mice with GVHD.

ISC and Paneth cell numbers are reduced in GVHD (FIGS. 3D, 4E). Crypt function and Paneth cell renewal post-BMT are altered due to the observed Paneth cell loss in GVHD. Loss is due to impaired stem cell function or due to immune-mediated loss of the stem cells will be determined. Evaluation of kinetics of ISC and Paneth cell loss in GVHD can be done to identify the earliest evidence of damage to ISCs and their niche. Lineage tracing of epithelial cells in Lgr5-LacZ lineage-tracing reporter mice can be conducted as described herein, however in an allo transplant setting. Crypt, villus, and Paneth cell renewal post-BMT in recipients of LP→B6 ($H-2^b→H-2^b$) miHA and B10.BR→B6 ($H-2^k→H-2^b$) MHC mismatched transplants can be evaluated, comparing recipients of TCD BMT (no GVHD) vs. recipients of marrow and T cells (GVHD). Lineage tracing can again be performed 5, 7, and 10 days post-BMT to evaluate the kinetics of epithelial regeneration from $Lgr5^+$ ISCs. The expression of ISC and Paneth cell related molecules (Lgr5, BMI-1, Hopx, mTert, Lrig1, Wnt3, EGF) can be measured again.

Additionally, a temporal relationship between ISC loss and Paneth cell loss can be established by a time course study measuring ISC and Paneth cell numbers pre-transplant and 1, 3, 5, 7, 10, and 14 days post-BMT. This can be performed using Lgr5-LacZ stem-cell-only B6 reporter mice in which the β-galactosidase reporter molecule is expressed constitutively in Lgr5$^+$ ISCs but not in their progeny. Lgr5$^+$ ISCs can thus be counted with use of the reporter mice, and Paneth cells can be counted based on their characteristic histologic appearance after H&E staining. The earliest direct evidence of damage to the ISC compartment can be established in order to determine if ISC loss or Paneth cell loss occurs prior to the other in GVHD.

As per the standard in murine models, TBI can be used as the method of pre-transplant conditioning. Additionally, evaluating GI epithelial renewal after treatment with non-myeloablative and ablative doses of chemotherapy may be done by evaluating for damage to the ISC compartment in patients having undergone clinical transplantation. The studies proposed emphasize Lgr5 expression as a marker of ISCs supported by the in vivo and ex vivo stem cell function of Lgr5$^+$ cells. An alternative approach to stem cell phenotyping such as assessment of CD44$^+$CD166$^+$CD24$^-$ cells. Paneth cells make up the ISC niche in the SI but are largely absent in the LI, where Wnt signals are thought to be provided to the ISCs by niche-supporting kit$^+$ cells. Therefore studies described herein and contemplated experiments are described herein to evaluate Paneth cells in the SI in GVHD. Additional studies on LI can be done by evaluating histologically for ckit$^+$ LI niche cells.

3. Crypt Damage from GVHD with an In Vitro Model of ISC Function.

Figure 3E:
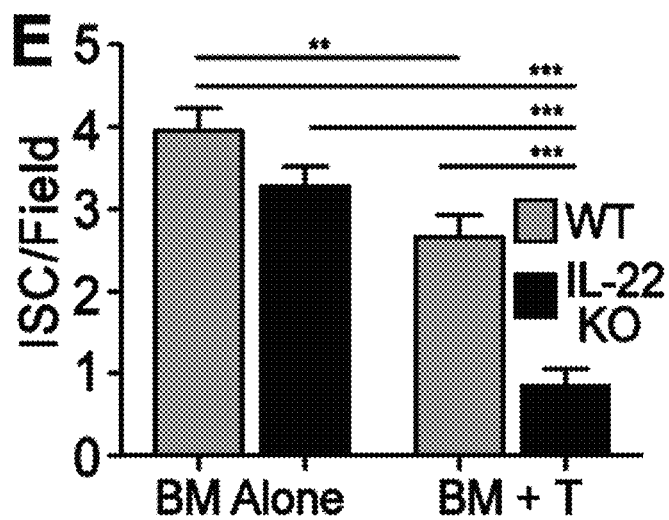
Figure 3F:
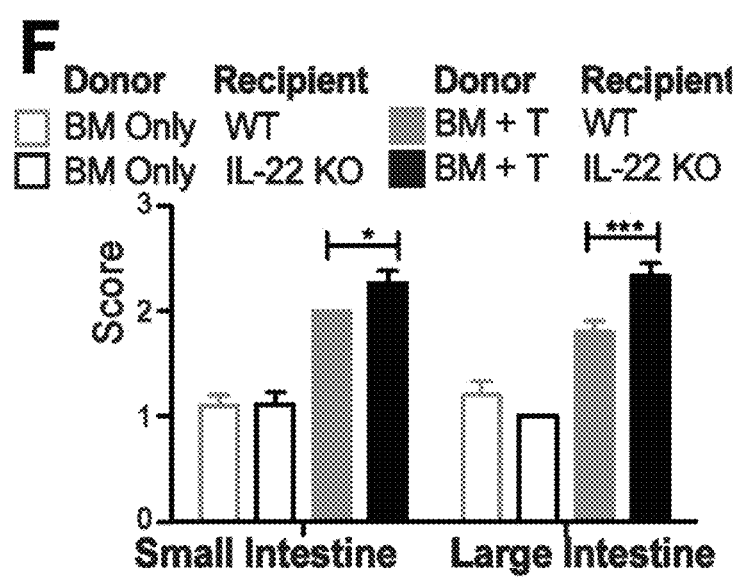
Figure 3G:
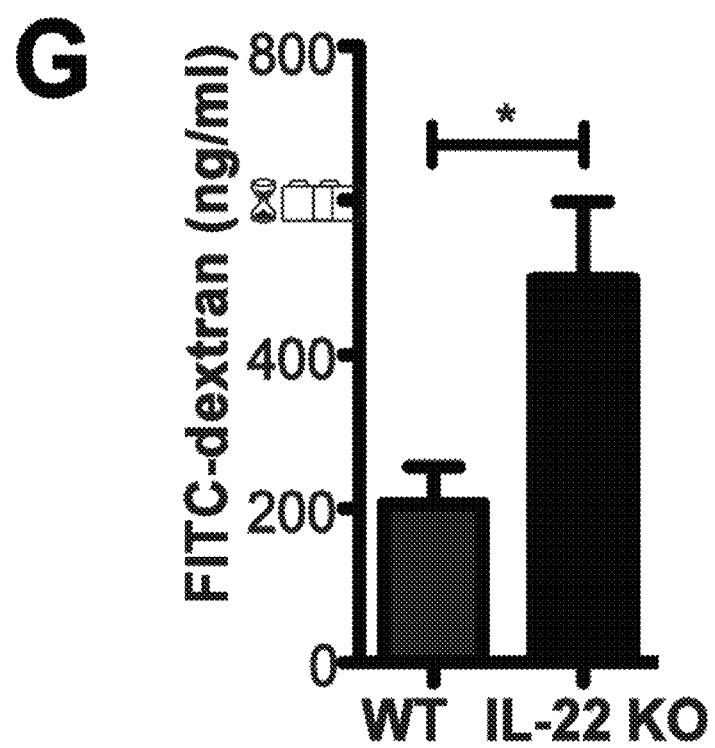

ISCs post-BMT can be assessed by culturing intestinal organoids from transplanted mice. ISCs are reduced in GVHD through the use of genetic, phenotypic, and histologic markers (FIGS. 3D-E). Stem cells can be evaluated functionally in GVHD by their ability to form intestinal organoids in vitro. Crypts were isolated from the small and LI from intestinal epithelium and cultured in semisolid medium in the presence of stem cell growth factors (R-spondin1, EGF, noggin for SI; R-spondin1, EGF, noggin, HGF, and Wnt3a for LI). As each crypt contains a functional stem cell compartment with ISCs and supportive niche cells, crypts cultured ex vivo grow into organoids with crypt buds that recapitulate the in vivo intestinal organization with crypt-villus structures and central lumens (FIG. 6). Additionally, as evidence of their ISC capacity, single Lgr5$^+$ cells from SI and LI grown in this fashion are able to generate their own niche cells and form organoids from single cells[38, 39]. Allo-BMTs as described in herein may be done by and isolating SI and LI crypts from recipients without GVHD (TCD marrow alone) and recipients with GVHD (marrow+T cells). Crypts can be harvested on days 1, 3, 5, 7, 10, and 14 post-BMT to evaluate the kinetics of damage to functional stem/progenitor cell niche. In addition, Lgr5-GFP reporter mice can be used as transplant recipients so that single ISCs can be isolated by FACS post-BMT and cultured in vitro to evaluate the function of isolated ISCs in GVHD, providing a functional read out of the stem cell niche and specifically ISCs in GVHD.

4. An In Vitro System Modeling GVH Reactions Against the Stem Cell Niche.

Gut GVHD manifests as intestinal disease however it apparently is the culmination of a systemic process involving T cell activation and migration. Indeed, the direct interactions occurring between allo T cells and recipient epithelial cells are not known. In order to visualize and efficiently test the mechanisms without limiting the invention to any particular mechanism of T cell-mediated damage to the stem cell niche, an in vitro system modeling gut GVHD with T cells directly interacting with GI epithelium cultured ex vivo can be tested. In preliminary studies, crypts cultured in vitro in the presence of allo T cells have a reduced capacity to grow into organoids.

Therefore, murine SI and LI crypts can be isolated and cultured into organoids in the presence of allo T cells. Crypts are cultured with naive T cells, T cells pre-activated polyclonally (anti-CD3/anti-CD28), and T cells activated by APCs from crypt-background mice. Crypts can be assessed for their capacity to grow into organoids. This allows for discrimination between the requirement for pre-activation/antigen presentation and the ability of intestinal epithelium to activate T cells directly for its own elimination, as well as for differential capacities of CD4 and CD8 T cells. Organoids can be counted and measured for diameter and area by light microscopy. High resolution three-dimensional images can also be evaluated by confocal microscopy. In addition to culturing intact crypts, the above experiments can be repeated by culturing individual ISCs isolated from Lgr5-GFP reporter mice with allo T cells and measuring organoid formation as above. This also allows for direct imaging of ISCs in cultured organoids by expression of GFP, and also allows for evaluation of interactions between allo T cells and ISCs to determine if allo T cells can directly eliminate or impair the function of ISCs.

Alternatively, single ISCs could be isolated by FACS based on the CD44$^+$CD166$^+$CD24$^{-37}$ phenotype. Additionally, this would provide an added benefit of being able to culture cells from mice of additional backgrounds.

B. Assess Stem Cell Elimination in GVHD.

1. Assess ISC and Niche Cell Expression of Death Receptors Before and after BMT.

The loss of ISCs in GVHD may be due to the loss of their niche-providing Paneth cells, or the loss of Paneth cells may be due to the loss of their precursor ISCs. Alternatively, there may be comprehensive nonspecific damage to the ISC compartment mediated by allo T cells attacking both the ISCs and niche cells. We hypothesized that ISCs and/or Paneth cells will express death receptors that are involved in their immune-mediated elimination in GVHD.

In this subaim we can isolate murine ISCs and Paneth cells from Lgr5-GFP reporter mice and phenotyope these cells by FACS for expression of potential death receptors involved in GVHD (Fas, TNFR, IFNγR, and DR5). Expression can be compared at baseline, after TCD BMT, and in mice with GVHD. ISCs and Paneth cells can be distinguished by GFP expression in ISCs, and the granular (sideward scatter high) CD24$^+$ bright phenotype (see FIG. 18E) for Paneth cells. We can also compare ISCs and Paneth cells by their expression of MHC class I and II and their expression of molecules that could provide resistance to apoptosis (BCl-2, Bcl-6, and c-FLIP).

2. Function of T Cell Cytotoxic Molecules in Damaging the ISC Compartment.

T cell cytotoxic pathways may be involved in the damage of the ISC compartment during GVHD. We can test the ability of T cells deficient for cytotoxic pathways to damage ISCs and their niche in vivo and in vitro. SI and LI crypts can be cultured with allo T cells from mice deficient in secreted or cell surface death receptor ligands (FasL, TNFα, IFNγ, TRAIL) as well as perforin and evaluate the number and size of organoid development as described herein. T cells with impaired ability to damage crypts in vitro are then evaluated in vivo by performing allo BMT with deficient T cells and assessing histologically post-BMT for ISC and Paneth cell elimination. If the in vitro allo T cell/crypt culture system proves unreliable, effects of potential death ligands can be tested in traditional in vivo GVHD models.

Utilizing cytotoxic-deficient T cells require primarily the use of B6 mice as the allo T cell source, preventing the use of B6 background Lgr5 reporter mice for in vivo readout of Lgr5 expression and for selection of individual ISCs for culture with deficient T cells. Therefore, neutralizing antibodies may be used to block cytotoxic pathways regardless of the T cell and crypt strains used, and may isolate ISCs by FACS based on $CD44^+CD166^+CD24^{-37}$ phenotype and culturing them with B6 background deficient T cells.

3. Expression of ISC Molecules and Niche Molecules in Patients Post-BMT.

Crypt apoptosis is a hallmark of GI GVHD, and we have observed deficiency of ISCs and Paneth cells in experimental GVHD models, and low Paneth cell counts are associated with increased non-relapse mortality in patients. However, specific damage to the ISC and niche cell compartment in clinical GVHD is poorly understood. Therefore, we can evaluate the expression of ISC-related molecules in BMT patients.

In order to assess ISCs and their niche in clinical GVHD, we can evaluate mRNA and protein expression of ISC-related molecules in the GI tract of patients requiring endoscopy for evaluation of GI complaints post-transplant. Biopsy specimens for research purposes can be acquired under MSKCC IRB protocol from patients undergoing clinically indicated GI biopsies related to symptoms post-transplant. Samples are compared between patients found to have biopsy proven GI GVHD and those without GVHD, including patients having undergone TCD transplantation. Tissue specimens can be evaluated for expression of Lgr5, BMI-1, Hopx, mTert, Lrig1, Wnt3, and EGF as described above. In addition, given our findings of IL-23-dependent IL-22-mediated support of ISCs in experimental GVHD, we can evaluate the expression of IL-22 and IL-23 in biopsied samples as well. We can also perform IHC on these samples to identify IL-22R expression in human crypts. Finally, GI expression of the molecules listed above can be compared to their expression in peripheral blood drawn the day of endoscopy to evaluate correlation between gut and systemic expression.

Biopsy specimens may also be evaluated by FACS to identify IL-22R expression on phenotypically identified ISCs and Paneth cells as described above with CD44, CD166, and CD24 staining. Alternatively, ISCs could be identified by in situ hybridization or IF for Lgr5.

4. Functional Damage to the ISC Compartment in Patients with GVHD.

While ISC damage is thought to occur due to the crypt damage found in GI GVHD, and while there is data for ISC loss in mice with GVHD, this type of damage has not been directly demonstrated in patients. We contemplate that patients with GVHD will have fewer detectable ISCs than patients without GVHD.

In order to assess the loss of ISCs in human patients with GVHD, SI and LI crypts can be isolated from patients undergoing clinically indicated endoscopies and biopsies for evaluation of GI symptoms post-transplant. Crypts isolated from patient biopsy specimens can then be cultured in vitro for organoid formation as described herein, comparing organoid generation from patients with or without GVHD, as well as comparing the stage of GVHD severity. As an alternative, we can also evaluate the loss of ISCs and niche cells by performing FACS of isolated cells for ISCs niche cells as described above. Additionally, normal GI tissue from the MSKCC Pathology department can therefore be evaluated as well to serve as a negative control for transplant-related effects on the ISC compartment.

C. ISC-Supportive Strategies to Treat GVHD.

We have identified that mice deficient for IL-22 have exacerbated ISC loss in GVHD and show herein that exogenous IL-22 administration increases ISC recovery. Therefore IL-22 can be used to serve as an ISC growth factor on organoids in vitro and as an epithelium-targeted GVHD treatment in mice with GVHD.

1. Effect of IL-22 on Organoids In Vitro.

While IL-22 can maintain epithelial integrity after damage, the effect of IL-22 on the ISCs compartment is largely unknown. Our preliminary data indicates that IL-22R is expressed on ISCs (FIG. 7A) and that IL-22 administration to mice with GVHD increases the recovery of ISCs (FIG. 4D). In addition, we have observed that IL-22 administration increases ISC proliferation in vivo (FIG. 7B) and that SI and LI crypts cultured with 1-5 ng/ml rmIL-22 grow into larger organoids than crypts cultured without IL-22 (FIGS. 7C-F).

Effect of IL-22 on ISC function can be observed by culturing crypts and ISCs isolated as described above in the presence of 0.1-10 ng/ml rIL-22 starting day zero or day two of culture. IL-22 can also be added on day zero of culture and then removed from the culture media on day two. Organoids can be evaluated for size and number, and can also be evaluated by confocal microscopy for high-resolution images. After identifying optimal IL-22 culture conditions, we can culture organoids from Lgr5-GFP reporter mice with IL-22 then can evaluate for JAK/STAT signaling, proliferation, and expression of anti-apoptotic molecules by FACS. We also evaluated the effect of IL-22 on human crypts isolated from transplant patients.

Figure 7A:
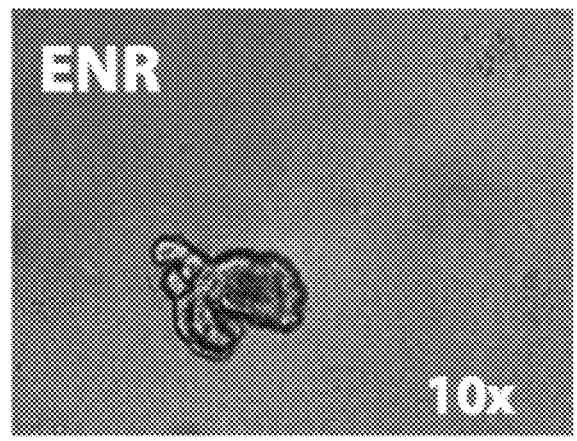
Figure 7A:
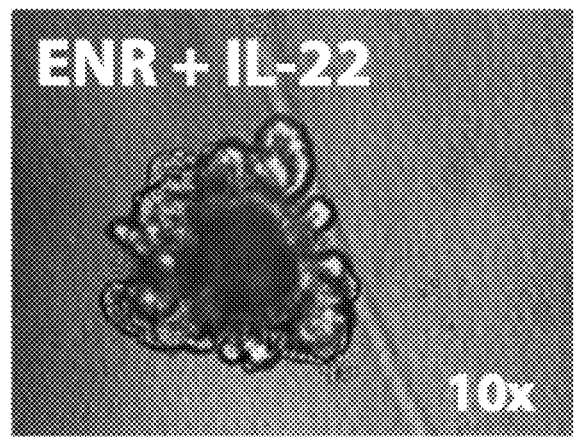
Figure 7B:
Figure 7C:
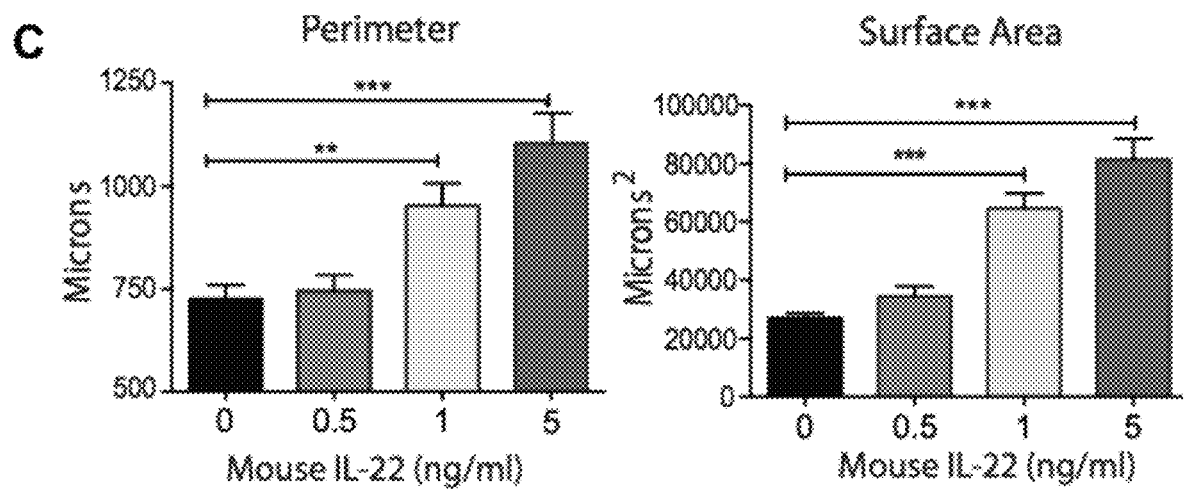

To begin evaluating for a role of IL-22 in regulation of the ISC compartment, murine small intestine (SI) crypts were isolated and cultured with EGF, Noggin, and R-spondin-1 (ENR) in the presence or absence of recombinant murine (rm)IL-22. Culturing crypts with rmIL-22 for seven days led to the growth of substantially larger organoids than those cultured with ENR alone (FIG. 7A). Increased organoid size was apparent as early as 5 days after culture. Two-dimensional perimeter tracing of organoids grown in three-dimensional culture conditions allowed for precise measurement of organoid size (FIG. 7B). Culture with 0.5-5 ng/ml rmIL-22 led to increased growth of SI organoids in a concentration-dependent fashion as determined by both perimeter and surface area (FIG. 7C). Although culture with >5 ng/ml rmIL-22 also led to increased organoid size, higher concentrations of IL-22 resulted in decreased numbers of organoids grown from cultured crypts (data not shown). This toxicity was dependent on additive effects of growth signals, as increasing concentrations of R-spondin-1, Wnt3, and EGF all further reduced the plating efficiency of organoids generated with IL-22 as a percentage of crypts put in culture.

Figure 7D:
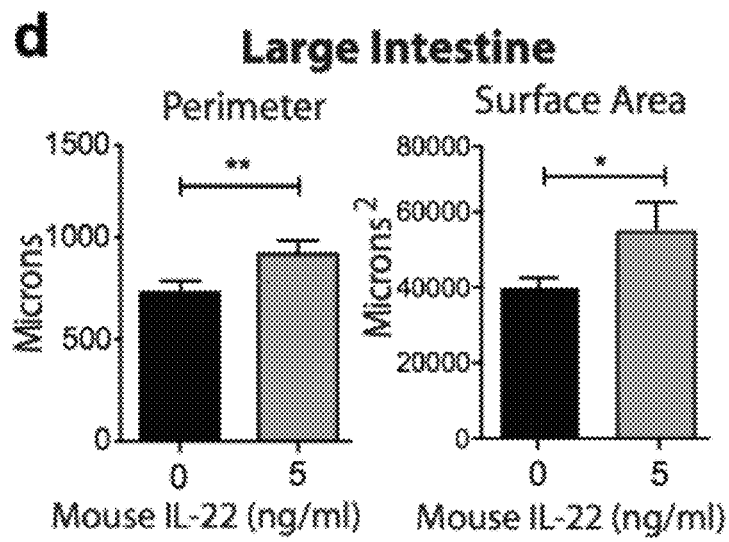
Figure 7E:
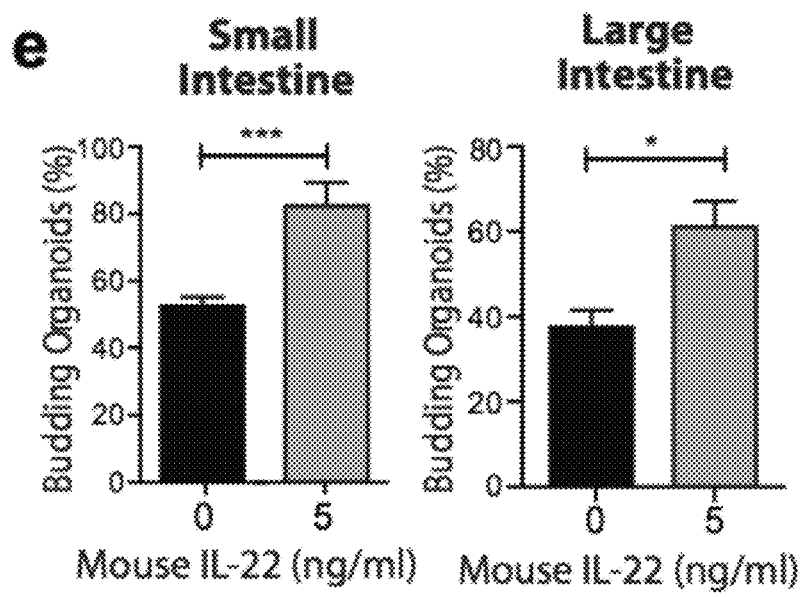

In addition to the augmented size of SI organoids, culture with IL-22 led to increased perimeter size and surface area of large intestine (LI) organoids (FIG. 7D). ISCs are located within the crypt buds that grow during organoid development. IL-22 culture led to significantly greater crypt budding in both SI and LI organoids (FIGS. 7A,E), suggesting structural evidence of stem cell compartment regeneration. Additionally, a recombinant human IL-22 dimer protein was able to increase the size of SI and LI organoids (FIGS. 7F,G), suggesting a translational potential for this compound.

Group 3 TLCs are a major source of GI IL-22 in colitis, during enteric bacterial infection, and after BMT13-16. To determine if ILCs could regulate the ISC compartment and augment organoid growth, CD45+CD11b−CD11c−B220−CD3−CD90+ cells were sorted from intestinal lamina propria and cultured in Matrigel with freshly isolated SI crypts. ENR provided basic signals for organoid development, and a cocktail of cytokines including IL-23 was included for activation of TLCs. The presence of ILC activation cytokines alone had no effect on the growth of SI organoids. However, co-culture with ILCs led to increased organoid size (FIG. 7H), demonstrating the potential of ILCs to regulate the ISC compartment and epithelial regeneration ex vivo.

Figure 16A:
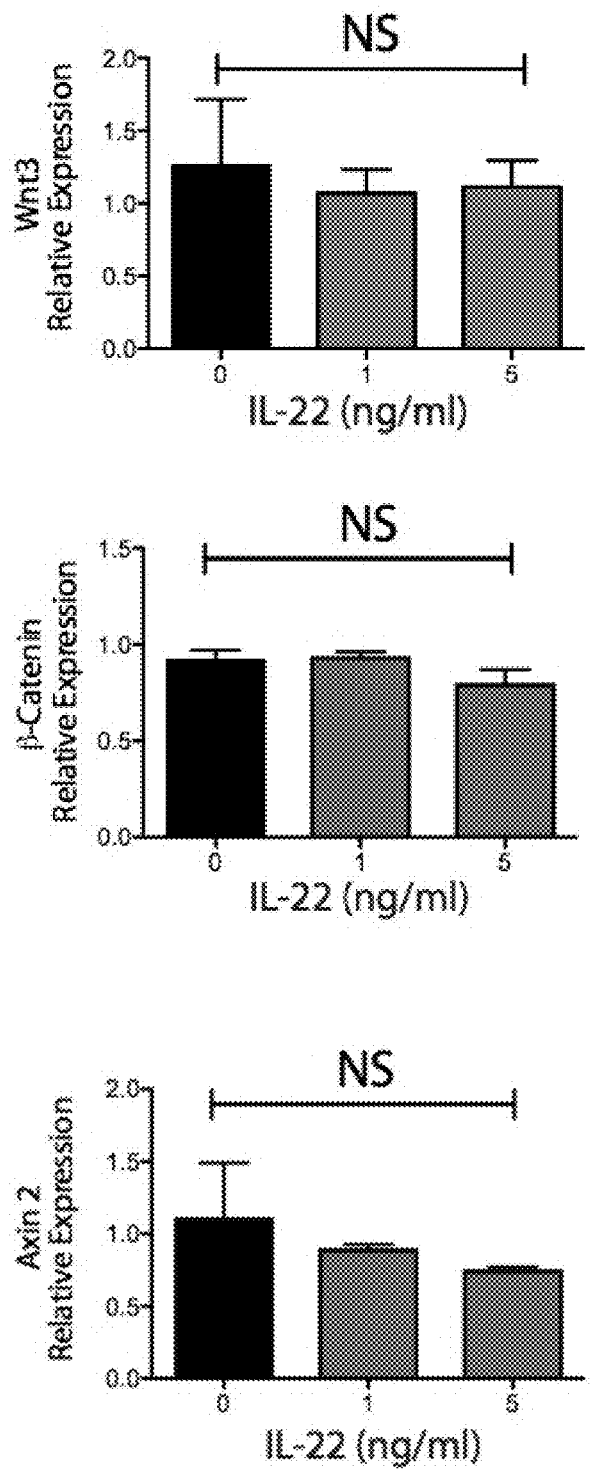
Figure 16B:
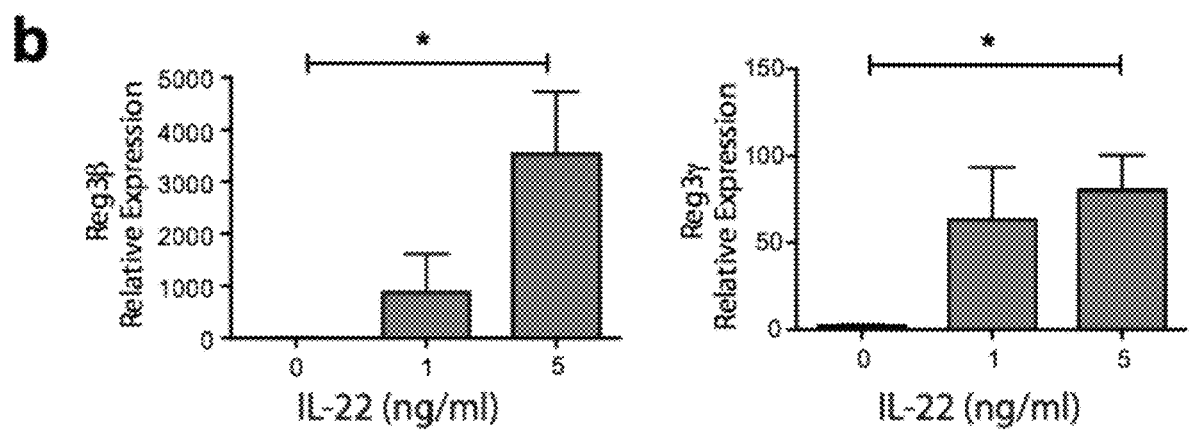

We next evaluated intracellular signaling activated by IL-22 within organoids. Although Wnt/β-catenin signaling is essential for ISC maintenance and organoid function ex vivo12, we found no evidence of enhanced production of molecules in the Wnt/β-catenin pathway within SI organoids cultured with IL-22, including no difference in expression of Wnt3, β-catenin, or Axin 2 (FIG. 16A). Despite the recent finding that Slit2 and Robo1 can regulate ISC recovery from damage induced by chemotherapy and radiation17, we also found no difference in their expression after culture with IL-22 (not shown). However, organoid culture with rmIL-22 led to increased mRNA for Reg3β and Reg3γ (FIG. 16B), innate antimicrobial molecules whose expression is dependent on STAT3 signaling.

Figure 16C:
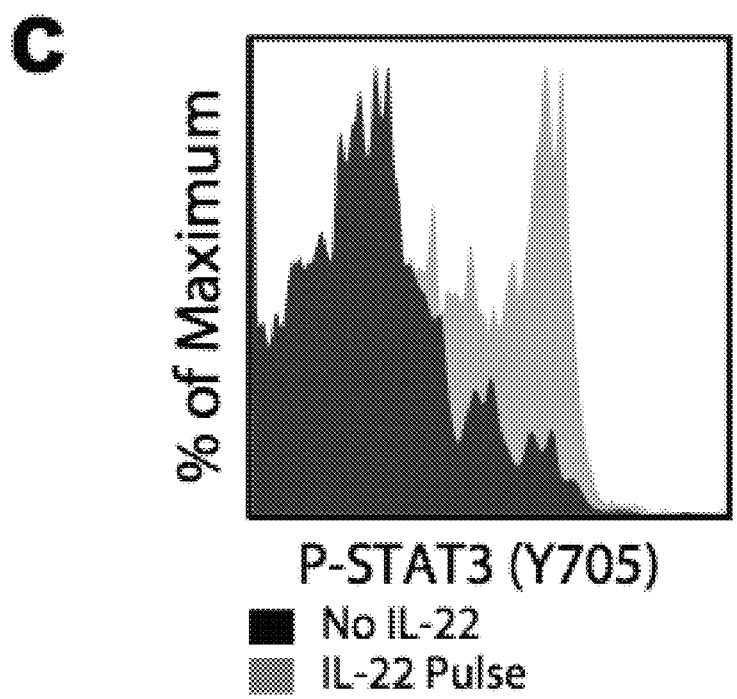
Figure 16D:
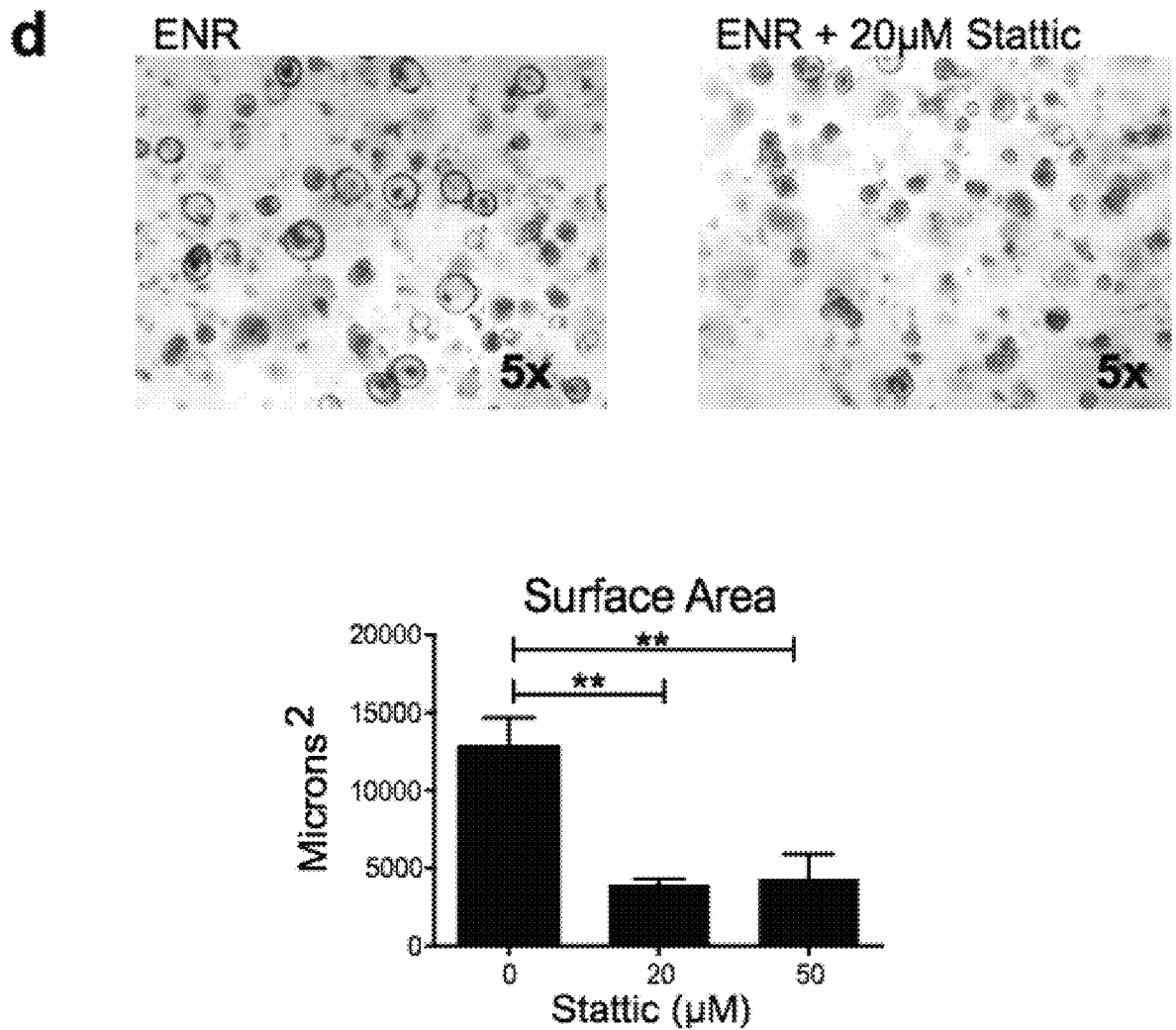
Figure 16E:
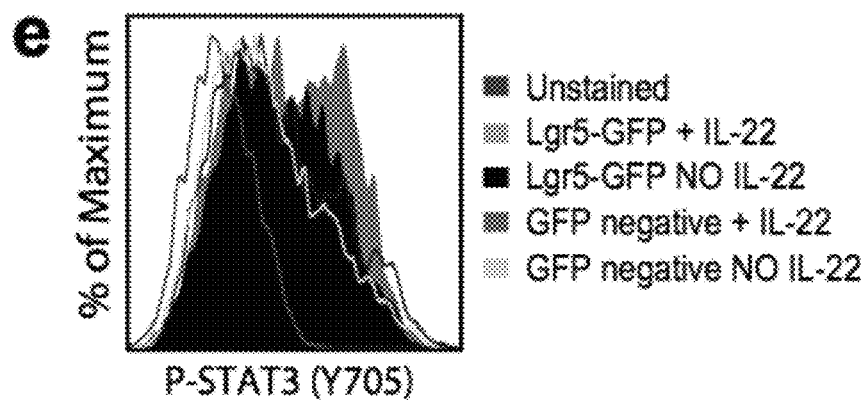
Figure 16F:
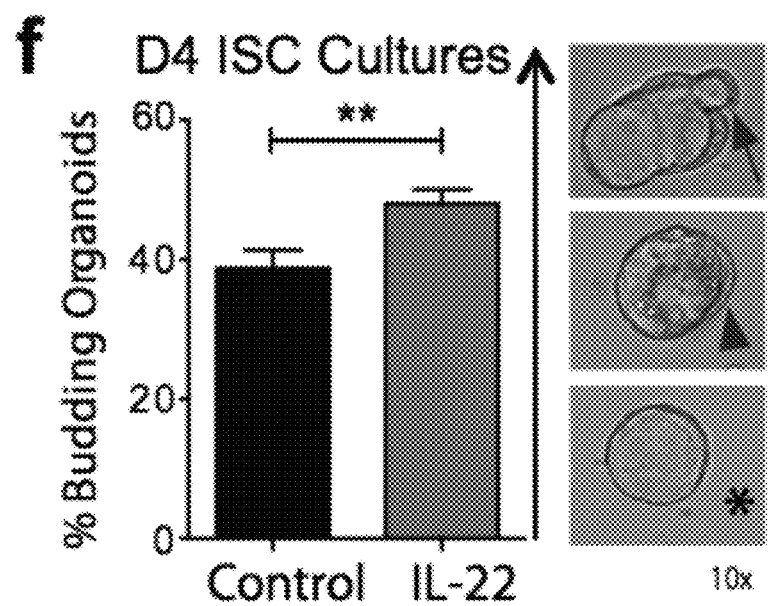

Little is known about JAK/STAT signaling within ISCs, although it has been reported that STAT3 may be important for ISC maintenance. We evaluated STAT3 signaling in SI organoids by phosflow and found that IL-22 led to phosphorylation of STAT3 Y705 (FIG. 16C). Furthermore, culture with the STAT3 inhibitor Stattic significantly impaired the growth of SI organoids (FIG. 16D). Lgr5+ ISCs can generate all cell types of mature intestinal epithelium in vivo and ex vivo. Examination of SI crypt cells isolated from Lgr5-GFP reporter mice by flow cytometry indicated STAT3 Y705 phosphorylation within GFP+ ISCs in response to IL-22 stimulation in vitro (FIG. 16E), thus demonstrating IL-22 signaling within Lgr5+ cells.

Figure 16G:
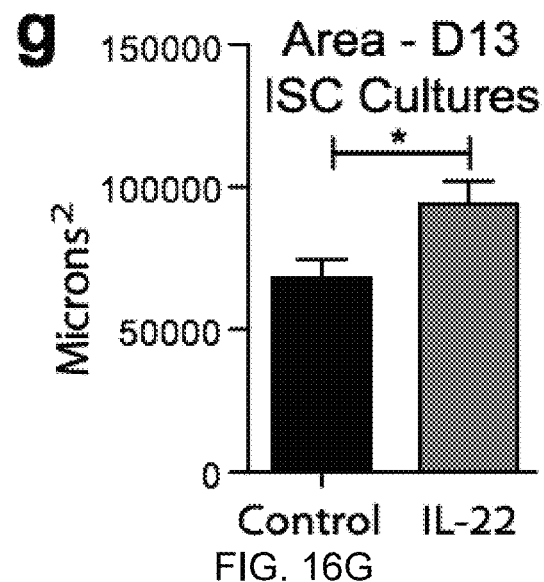

To determine if IL-22-dependent signaling in ISCs was functionally significant, we isolated Lgr5-GFP ISCs by fluorescence-activated cell sorting, and cultured single ISCs in Matrigel under standard conditions +/−IL-22. IL-22 led to significantly greater budding of early organoids after just four days in culture (FIG. 16F), ultimately resulting in increased organoid size after starting with single ISCs cultured in the presence of IL-22 (FIG. 16G). IL-22 can thus act on individual ISCs to activate STAT3 phosphorylation and accelerate organoid growth.

Figure 16H:
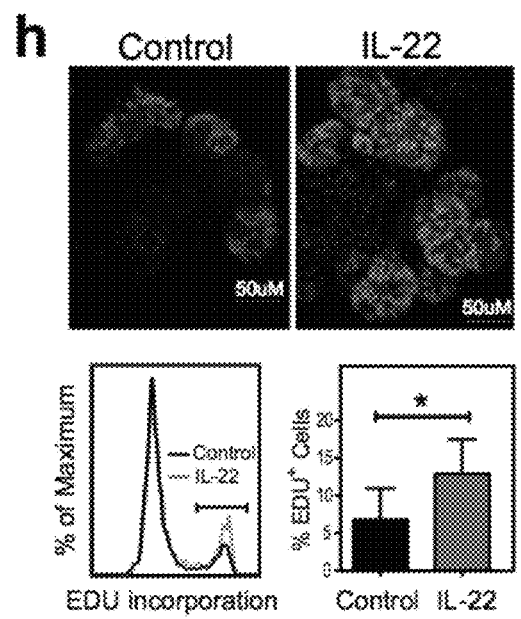
Figure 16I:
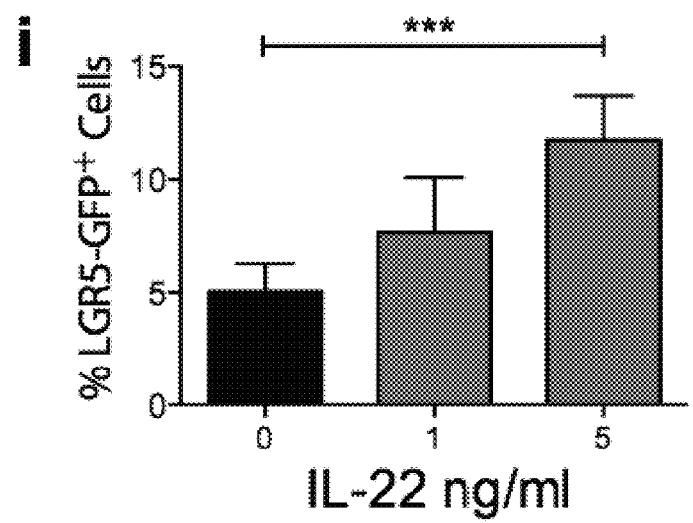
Figure 16J:
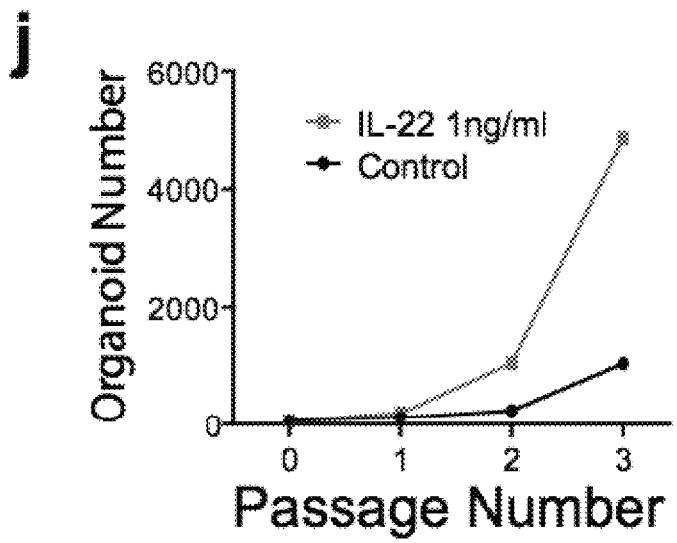
Figure 17A:
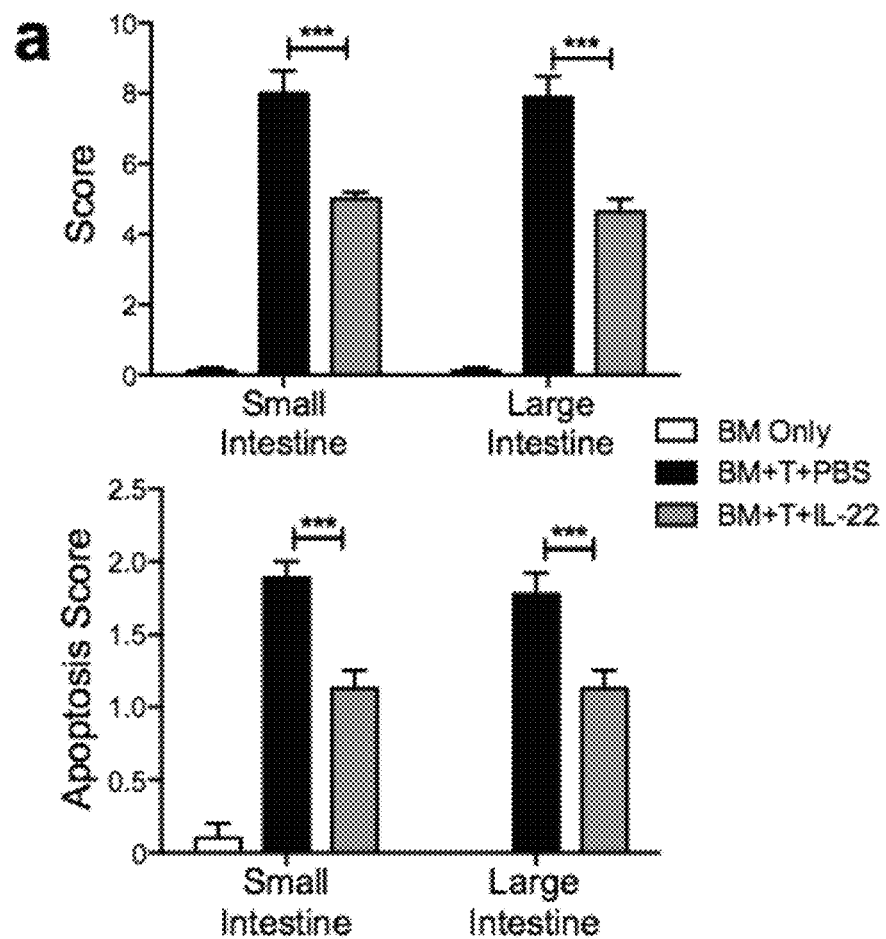
Figure 17B:
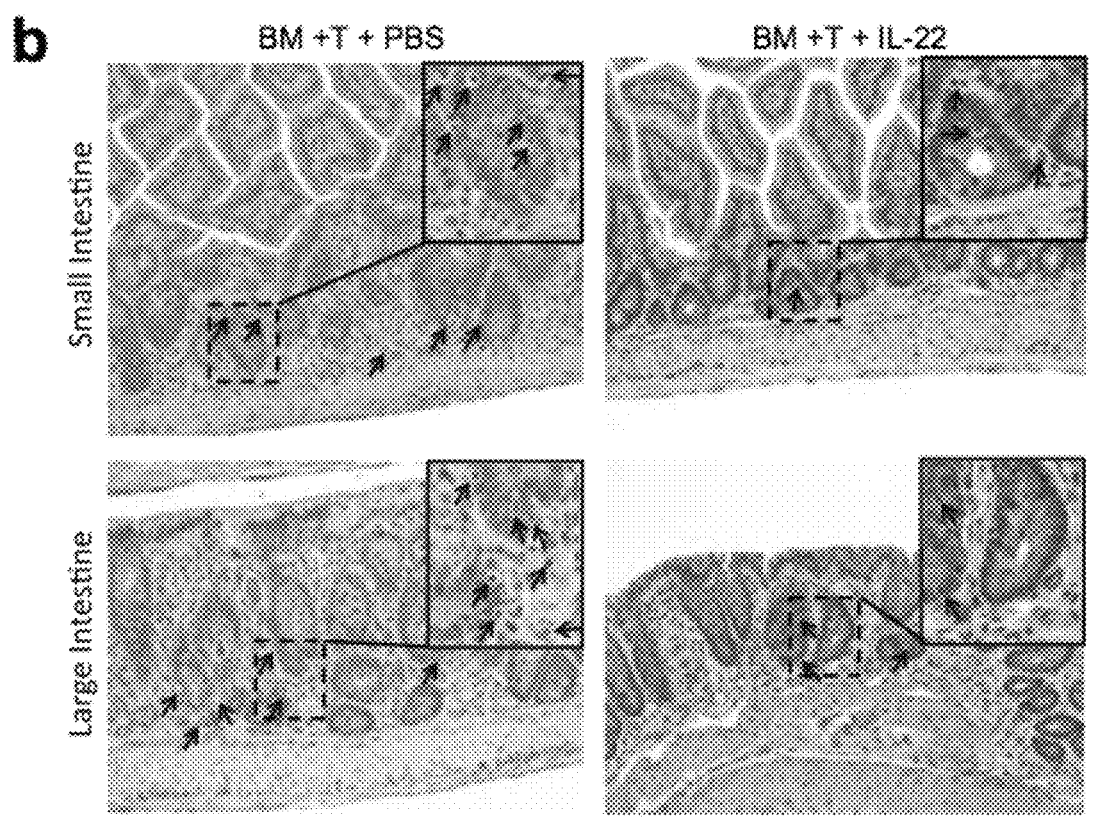
Figure 17C:
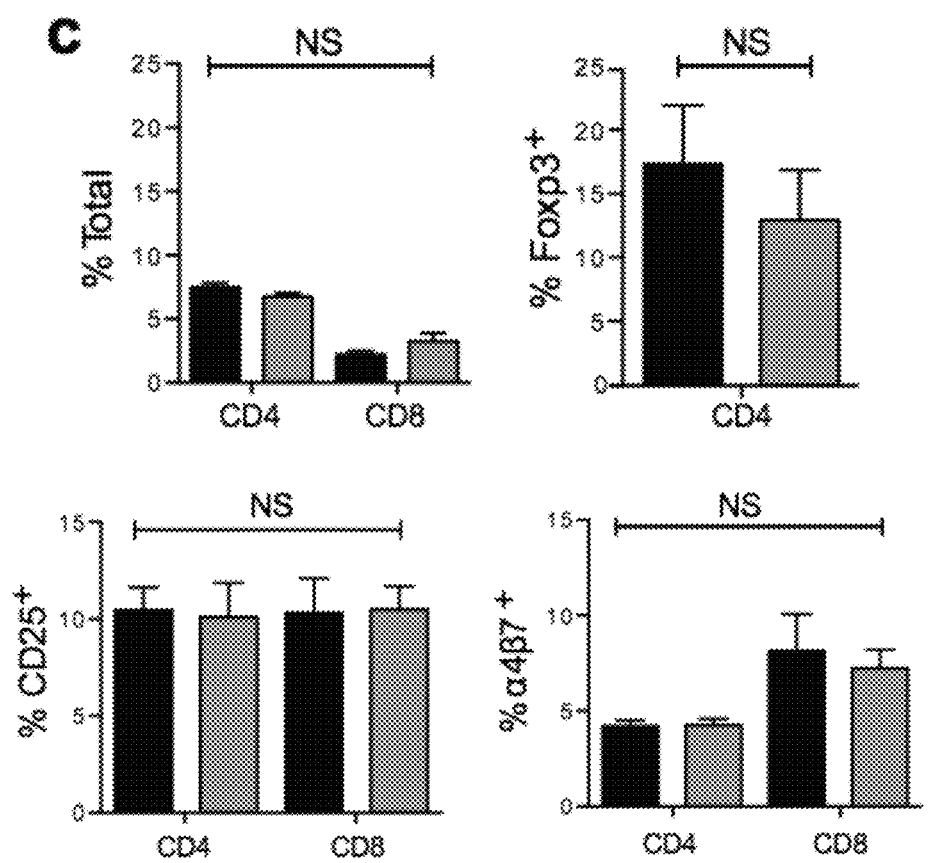
Figure 17D:
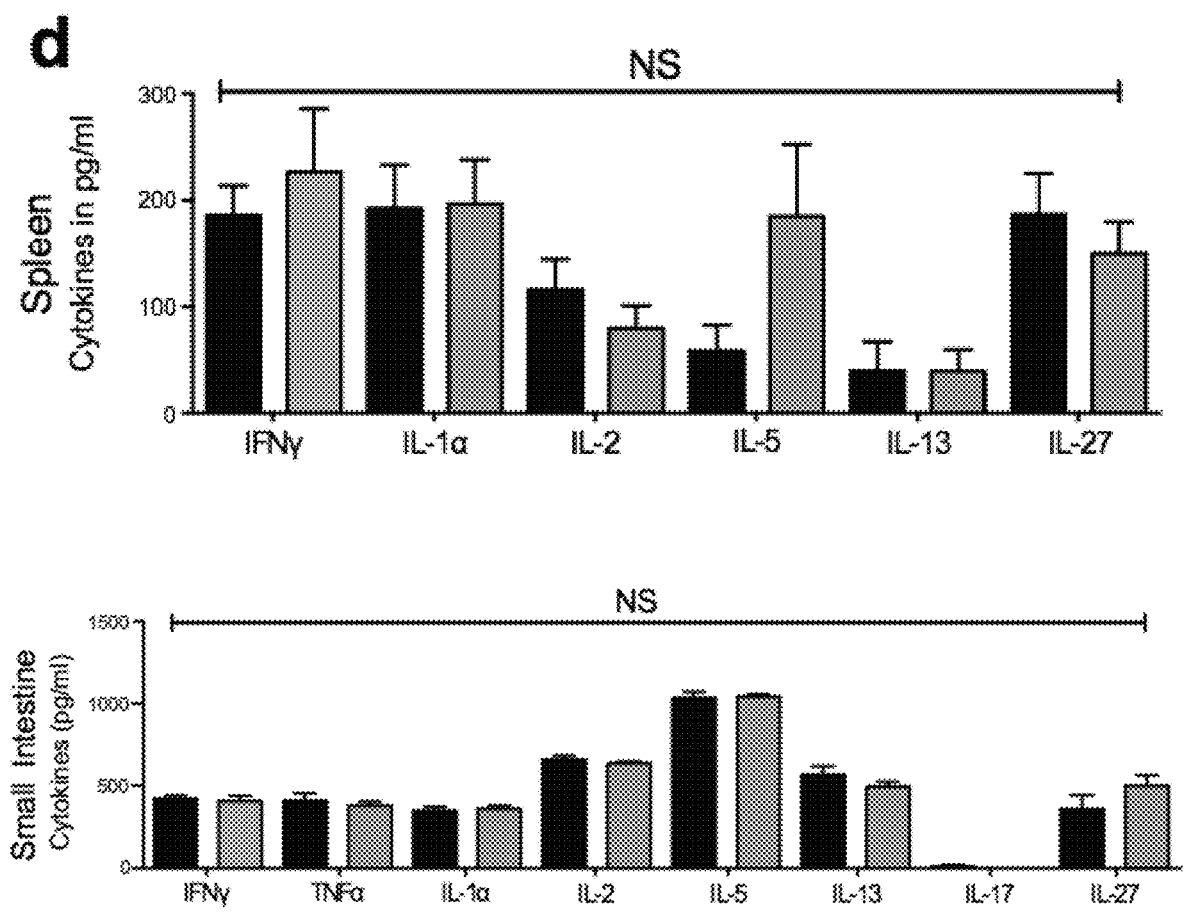
Figure 17E:
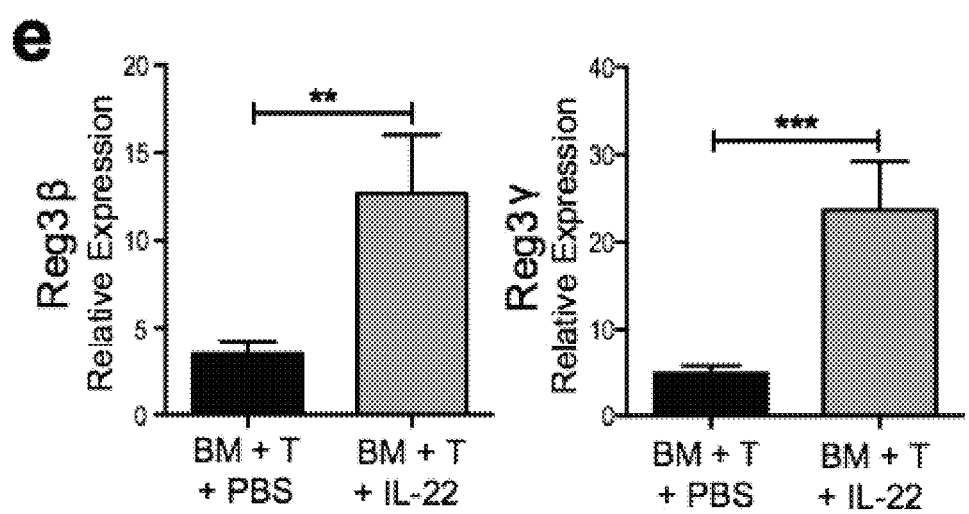

As IL-22 led to increased organoid size, crypt budding, and STAT3 activation, we next sought to determine if this resulted in expansion of ISCs. We evaluated 5-ethynyl-2'-deoxyuridine (EdU) incorporation into organoids cultured with IL-22, as a short one-hour incubation of organoids with EdU has been shown to mark the S phase of fast-cycling CBC cells. IL-22 led to increased organoid EdU incorporation, indicating augmented proliferation within organoid crypts (FIG. 16H). Furthermore, culturing organoids derived from Lgr5-GFP reporter mice with IL-22 indicated expansion of Lgr5-GFPhigh ISCs in response to IL-22 (FIG. 16I). Finally, serial passaging demonstrated that increased numbers of organoids could be generated after culture with IL-22, further indicating the expansion of functional ISC compartments (FIG. 16J).

FACS of cultured organoids purified from semi-solid media may have high background staining and may be difficult to interpret. In that case, organoids grown +/−IL-22 could be evaluated for proliferation and apoptosis by gene expression. In addition, microarray could be performed to globally evaluate crypt gene expression after IL-22 treatment.

2. Effect of IL-22 Administration on GVHD In Vivo.

ISC biology proposed here develops a therapeutic modality to promote ISC function as an epithelium-targeted treatment for GVHD. Preliminary data described herein indicated that IL-22 production is impaired in GVHD due to the loss of IL-22-producing ILCs (FIG. 2), and reintroduction of IL-22 by administration of rmIL-22 to mice with GVHD decreases gut GVHD pathology and increases ISC recovery (FIG. 4). Additionally, the IL-22 pathway does pathway does not appear to be a component of GVL, as IL-22 KO T cells as well as WT T cells in mice treated with rIL-22 administration demonstrated equivalent GVL against A20 lymphoma tumor cells. (FIGS. 8A,B).

Figure 7F:
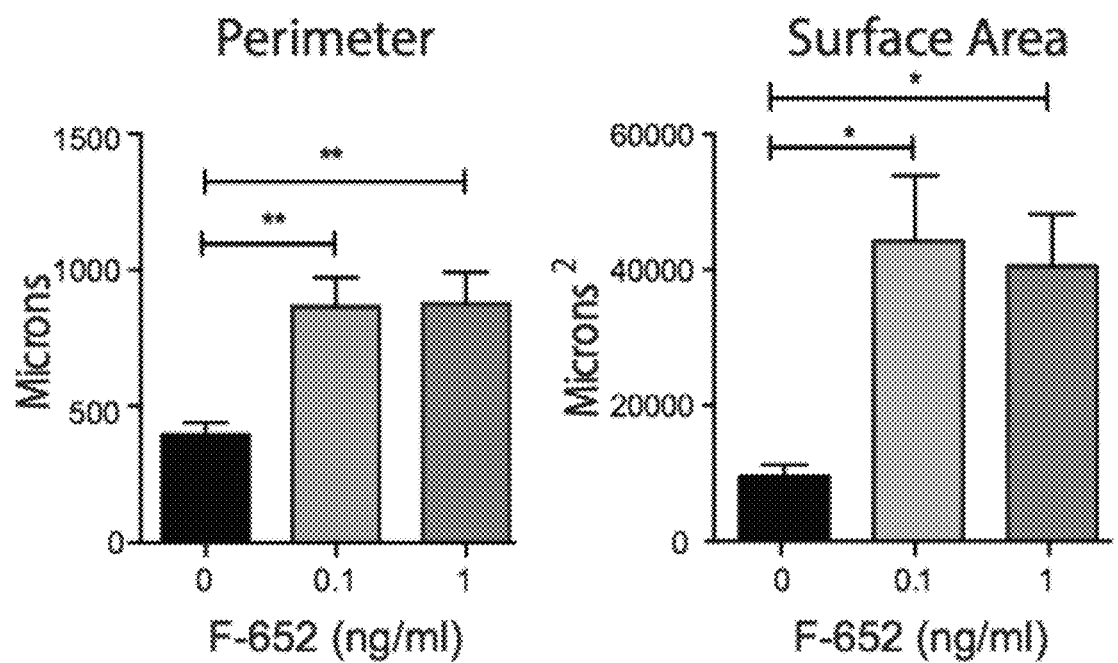
Figure 7G:
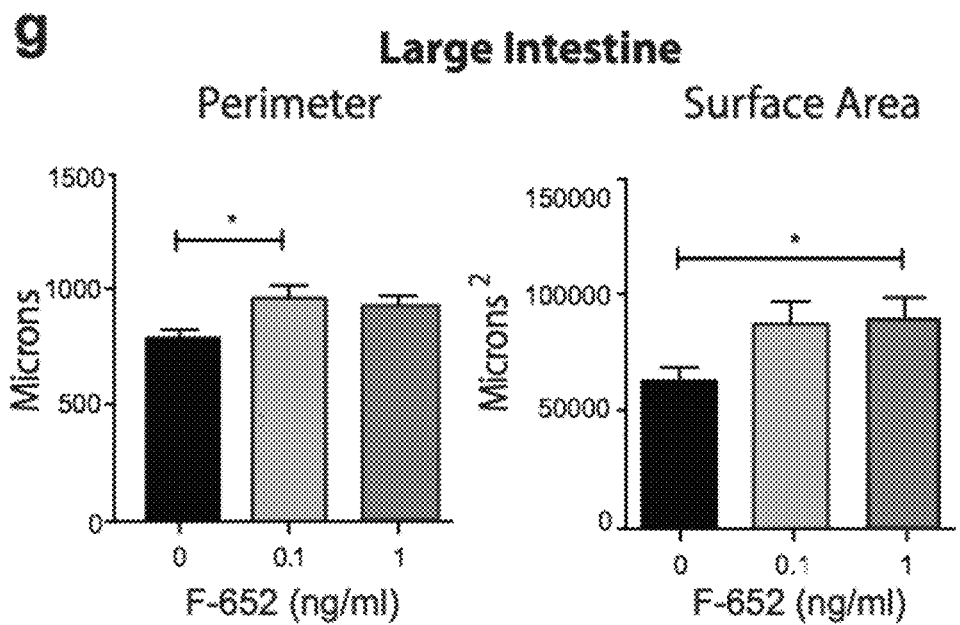
Figure 7H:
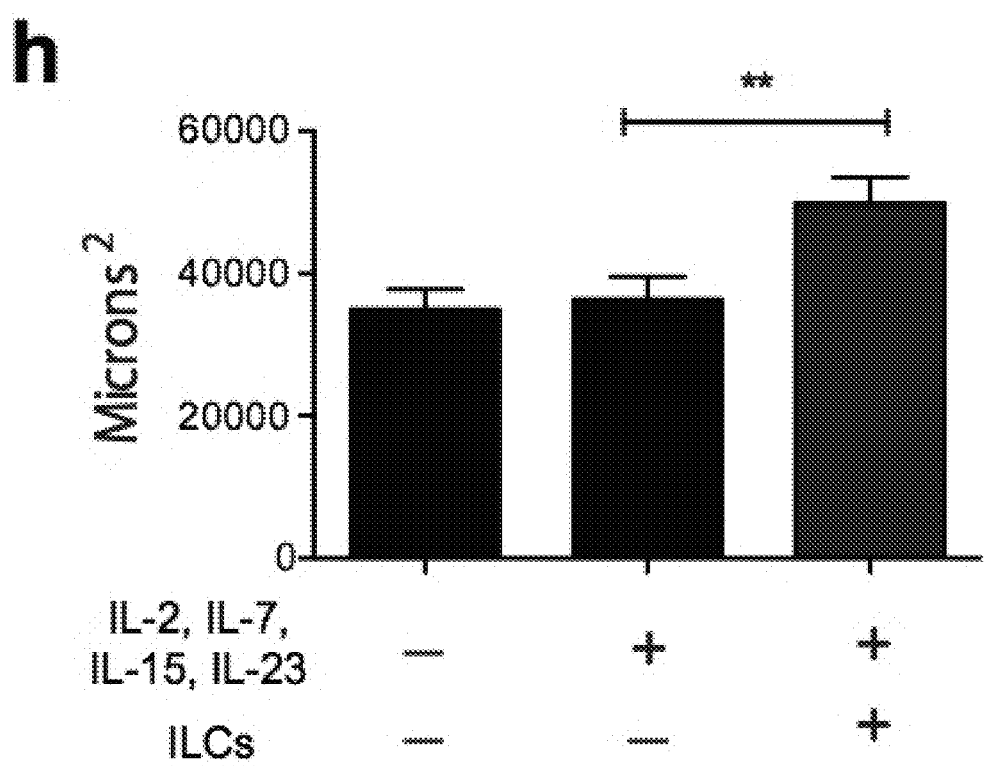

We acquired a clinical grade human IL-22 dimer, F-652 (Evive Biotechnology (Shanghai) Ltd.), that cross-reacts with mouse IL-22R. Potential benefits of using this dimer, formed by two IL-22 monomers with Fc fragments via coupling of the Fc fragments, include use in clinical translation along with the benefit of the increased half-life if the IL-22 dimer compared to the recombinant IL-22, as described in U.S. Patent Appln. No. US2003/0100076, herein incorporated by reference in its entirety. We observed that F-652 was able to augment the growth of organoids in vitro (FIGS. 7F,G). Therefore, we can test the effect of this IL-22 dimer on ISC recovery, GVHD pathology and survival, and on GVL in addition to further growth effects on organoids in vitro. In one preferred embodiment, the use of an IL-22 dimer is contemplated for treating patients with conditions involving inflammatory gastrointestinal tissue including but not limited to irradiation, radiation treatment, chemotherapy treatment, inflammatory bowel disease, colitis, Crohn's disease, autoimmune disorders, infectious disease and graft vs. host disease. In another preferred embodiment, the use of an IL-22 dimer is contemplated as a prophylactic treatment for patients undergoing procedures including but not limited to radiation exposure, chemotherapy treatments, tissue transplantation, cell transplantation, including patients at risk of conditions involving inflammatory gastrointestinal tissue including but not limited to an irradiated patient, a chemotherapy patient, a patient with an infectious disease, a transplantation patient, a patient with an autoimmune disease and the like.

Allo-BMT can be performed as described above with Lgr5-LacZ reporter mice as recipients with both miHA and MHC mismatched models. Recipients can be treated pre-transplant and/or post-transplant with F-652 human IL-22 dimer and then sacrificed three weeks post-BMT to evaluate for GVHD pathology and ISC recovery. Allo-BMT with WT recipients can be performed and evaluated for survival differences in GVHD after F-652 treatment, and we can transplant mice in the presence of hematologic malignancies (such as in FIG. 8) to evaluate the efficacy of GVL after treatment with F-652. As IL-22 administration may be most effective at promoting ISC function if provided with an immunosuppressive agent, we will also evaluate the combination of F-652 administration with a targeted anti-IL-23 neutralizing antibody. The role of IL-23 in stimulating allo T cells to mediate GVHD and the potential benefit of blocking it in GVHD was described. However, anti-IL-23 neutralizing antibodies meant to prevent T cells from causing GVHD us expected to limit the production of endogenous IL-22 expression. Therefore, this combinatorial approach may therefore serve to limit T cell mediated GVHD by blocking IL-23 while also promoting ISC function by adding back the IL-22 that is lost due to GVHD and IL-23 neutralization. Although IL-23 neutralization is a potential treatment of GVHD, it is not a current standard of care for treating GVHD.

Preliminary data indicated that IL-22 may be reducing GVHD by directly stimulating ISC proliferation, and not by indirectly supporting ISCs by targeting the ISC-supporting Paneth cells (FIGS. 4,7). These observations are made without limiting the invention to any particular mechanism. Therefore, an alternative approach is to test the reintroduction of new stem cells by transferring isolated ISCs or intact crypts to mice with GVHD as has been described in an experimental model of colitis.

Figure 18A:
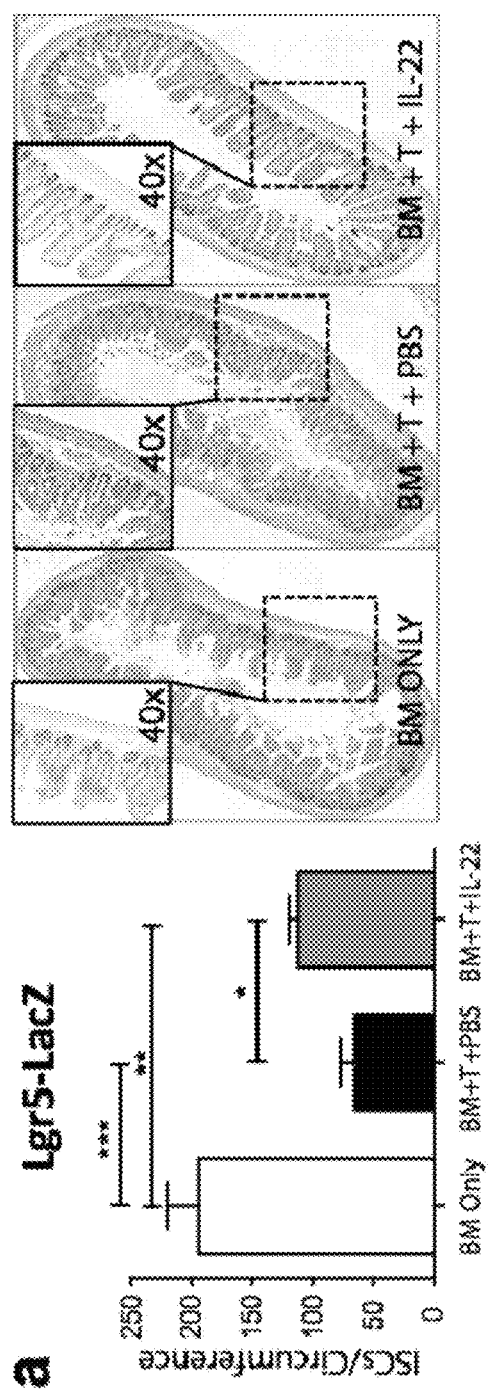

Reduced numbers of ISCs and niche-forming Paneth cells have recently been described in mice with GVHD. Given the stable alloreactive immunity after IL-22 treatment, we next evaluated the effect of IL-22 on the ISC compartment directly. We performed LP→B6 allogeneic BMT using Lgr5-LacZ recipients to identify ISCs post-transplant. BMT with T cells led to GVHD and significant loss of Lgr5+SI ISCs three weeks post-BMT (FIG. 18a). However, daily treatment with rmIL-22 led to increased recovery of Lgr5+ ISCs even with an ongoing alloimmune response and no immunosuppression (FIG. 18A).

Figure 18B:
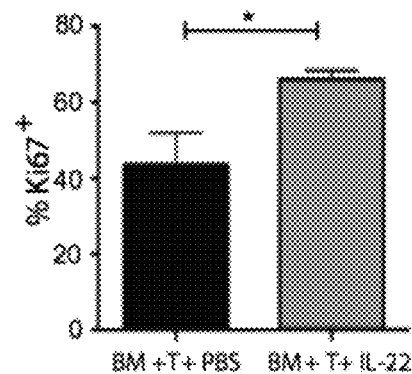

To understand how IL-22 administration could lead to increased numbers of ISCs in mice with GVHD, we transplanted B6 Lgr5-GFP reporter mice with LP marrow and T cells. Recipients were treated daily for seven days with rmIL-22 or PBS IP, and then SI crypts were isolated and evaluated by flow cytometry on day 14 post-BMT. Consistent with our ex vivo findings of increased organoid growth and EdU incorporation, Lgr5-GFP+ cells expressed increased Ki-67 after in vivo treatment with rmIL-22, indicating that the treatment augmented proliferation of the ISC pool (FIG. 18B).

Figure 18C:
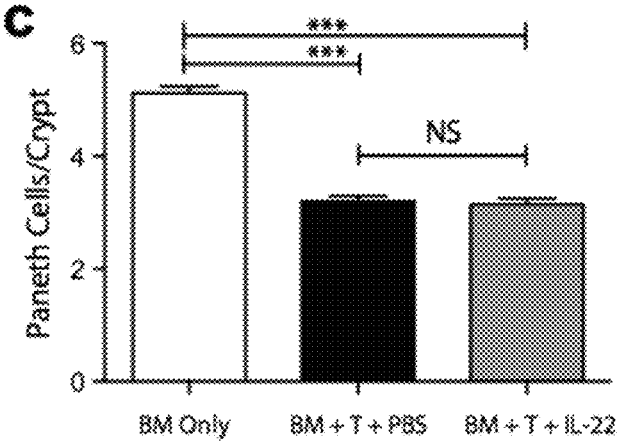
Figure 18D:
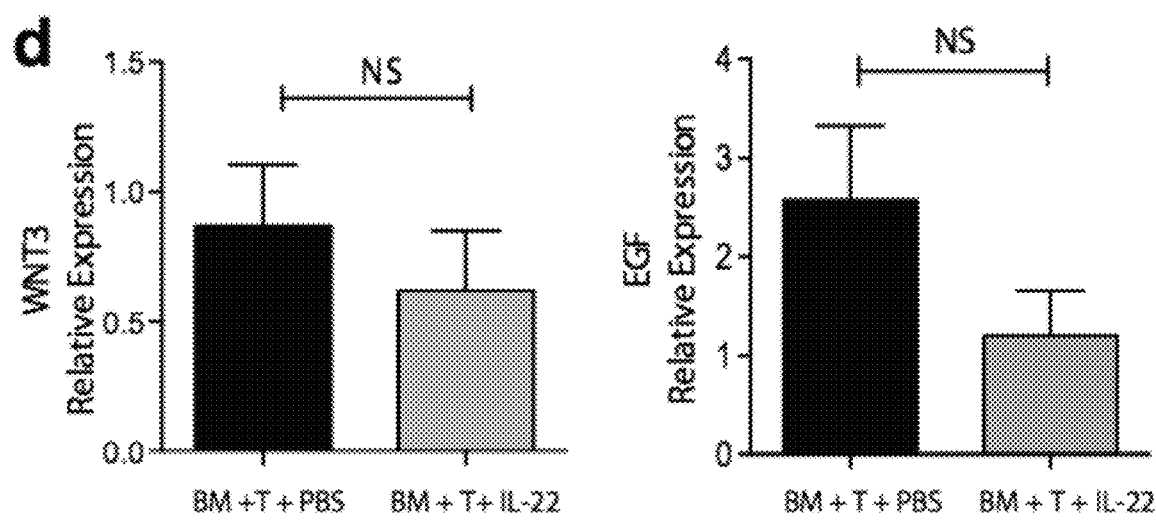
Figure 18E:
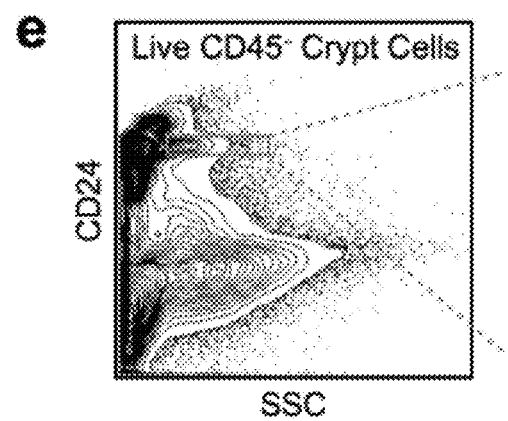
Figure 18E:
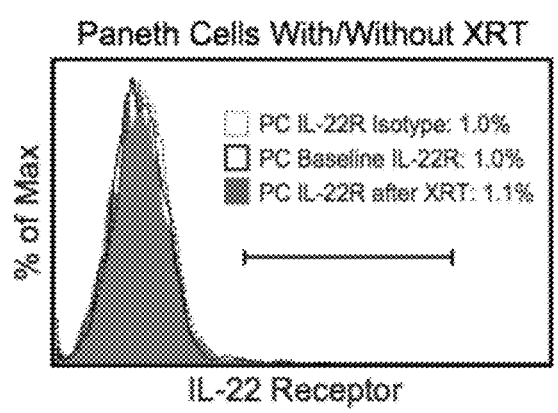
Figure 18E:
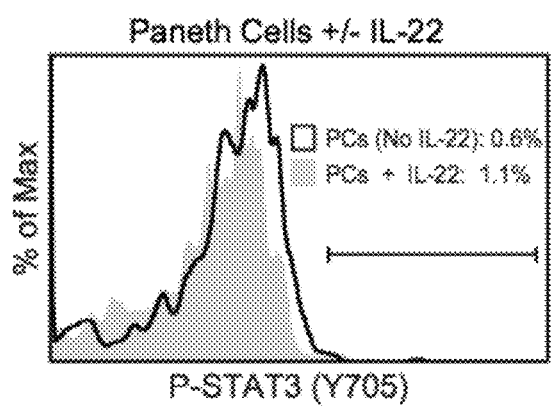
Figure 18F:
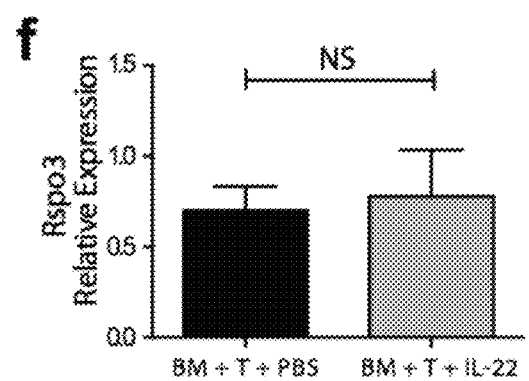
Figure 18G:
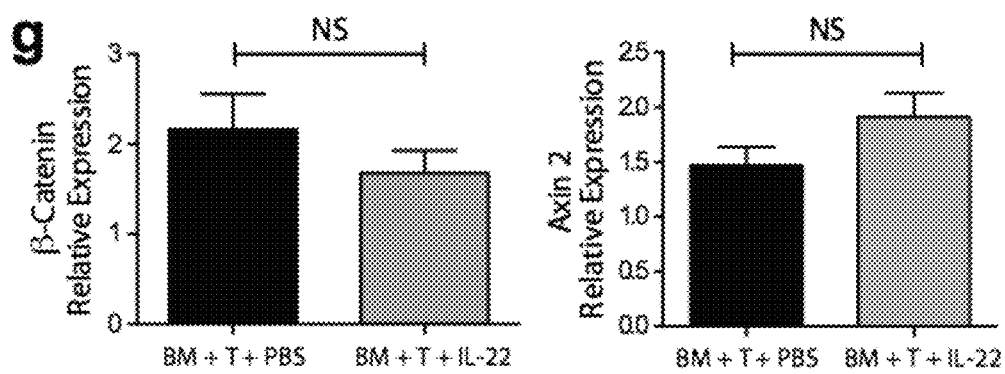

Paneth cells provide a supportive microenvironment for Lgr5+ISCs through delivery of Wnt and EGF signals to CBC stem cells. Additionally, IL-22 is thought to regulate Paneth cells and their production of innate antimicrobial molecules. We thus hypothesized that IL-22 administration could support ISC recovery post-BMT by improving the stem cell niche and augmenting Paneth cell-mediated support of ISCs. Consistent with studies of clinical GVHD and MHC-mismatched experimental models, LP→B6 minor antigen-mismatched BMT led to a reduction in Paneth cells three weeks post-transplant (FIG. 18C). However, despite the reduction in tissue pathology (FIG. 17A), rmIL-22 administration post-BMT did not increase recovery of Paneth cells (FIG. 18C). Furthermore, we observed no increase in SI mRNA for the Paneth cell-derived molecules Wnt3 and EGF that are known to support Lgr5+ISCs (FIG. 18D). We also found little evidence for expression of IL-22R on Paneth cells at baseline or after radiation injury, and while they may still respond to IL-22 under other circumstances, Paneth cells did not demonstrate STAT3 phosphorylation in response to IL-22 in vitro (FIG. 18E).

Although IL-22 did not improve the niche-supporting capacity of Paneth cells, it remained possible that IL-22 could indirectly promote ISC proliferation in vivo by augmenting stroma-mediated stem cell support. It was recently shown that stromal cells can contribute to maintenance of the ISC niche, supporting normal intestinal homeostasis in vivo through production of Wnts and R-spondin-3, even in the absence of Paneth cell-derived Wnts33. However, we found no evidence for increased niche-derived Wnt signals after IL-22 treatment in vivo (FIGS. 18F,G), indicating that IL-22 can induce proliferation of ISCs after immune-mediated damage without acting through either the Paneth cell or stromal-derived stem cell niches.

Figure 18H:
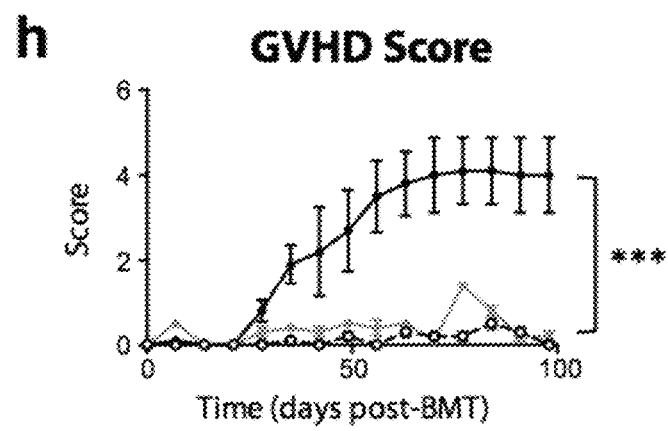
Figure 18I:
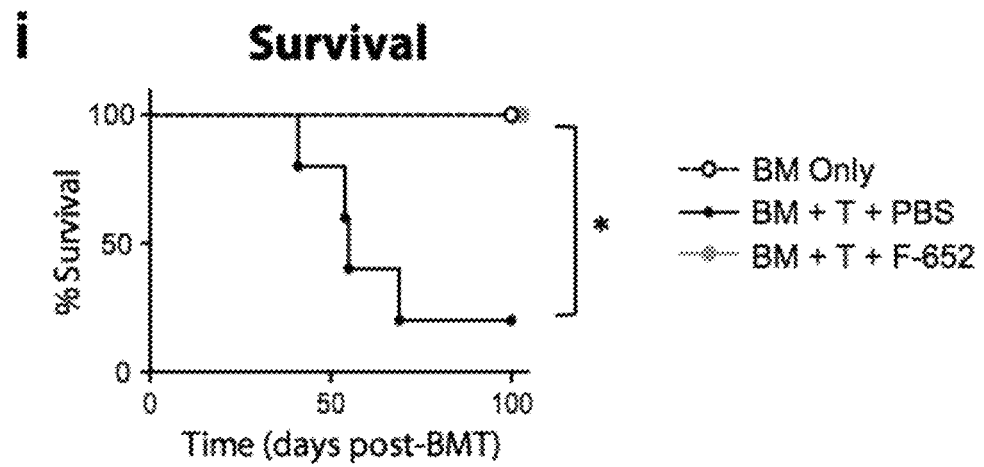

Finally, given the clear effect of IL-22 in augmenting ISC regeneration and epithelial recovery in vivo, we evaluated the impact of IL-22 administration on systemic GVHD. It has been proposed that GI damage may be central to the pathogenesis of systemic GVHD. Consistent with a recent report where IL-22 was administered peri-transplant, we found no improvement in GVHD mortality following F-652 administration to recipients of MHC-mismatched BMT (not shown). However, we found that an early intervention model with F-652 starting one week after MHC-matched allogeneic BMT led to reduced systemic signs of GVHD and significantly improved overall survival (FIGS. 18H,I).

II. IL-22+ Lactobacilli as a Novel Targeted Therapeutic Approach for Prevention and Treatment of Clinical GVHD.

As an alternative approach to pharmacologic reintroduction of IL-22, i.e. exogenous IL-22, we developed a probiotic strategy with *lactobacillus* that constitutively produces IL-22, see below and in the Experimental section. Thus in one embodiment, exogenous IL-22 is used in methods of treatment along with a probiotic. In another embodiment, exogenous IL-22 is administered to patients as described herein, along with a probiotic. In preliminary studies, administration of a probiotic of the present inventions to mice post-BMT appeared to reduce systemic GVHD.

Therefore, IL-22+lactobacilli are contemplated as a novel targeted therapeutic approach for prevention of clinical GVHD and transplant-related tissue damage without limiting essential donor immune functions. *Lactobacillus* administration was shown to reduce experimental GVHD. Moreover, *Lactobacillus paracasei* is a normal constituent of human GI flora. Therefore the inventors contemplated the use of engineered *Lactobacillus paracasei* to deliver therapeutic doses of exogenous IL-22 for providing additional therapeutic benefits. Indeed, the following describes making and using IL-22 expressing bacteria along with preliminary experiments showing the results of reduced endogenous IL-22 production, section A. Methods and materials for making and using IL-22+lactobacilli including contemplative experiments are described in section B.

A. HCT in Mice Expressing Reduced Endogenous IL-22.

IL-22−/− KO recipients of HCT demonstrated increased mortality following both minor (FIG. 1A) and major (FIG. 1B) antigen-mismatched HCT, as did wild-type (WT) recipients treated systemically with an anti-IL-22 neutralizing antibody (FIG. 1C). Transplantation into IL-22 KO recipients led to increased histopathologic evidence of GI and hepatic GVHD (FIG. 2A). Therefore, host-derived IL-22 effected mortality and post-transplant GVHD pathology.

Figure 2B:
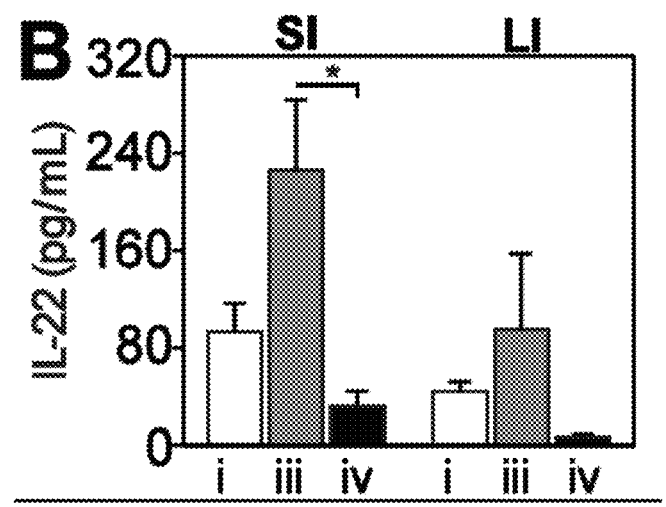
Figure 2E:
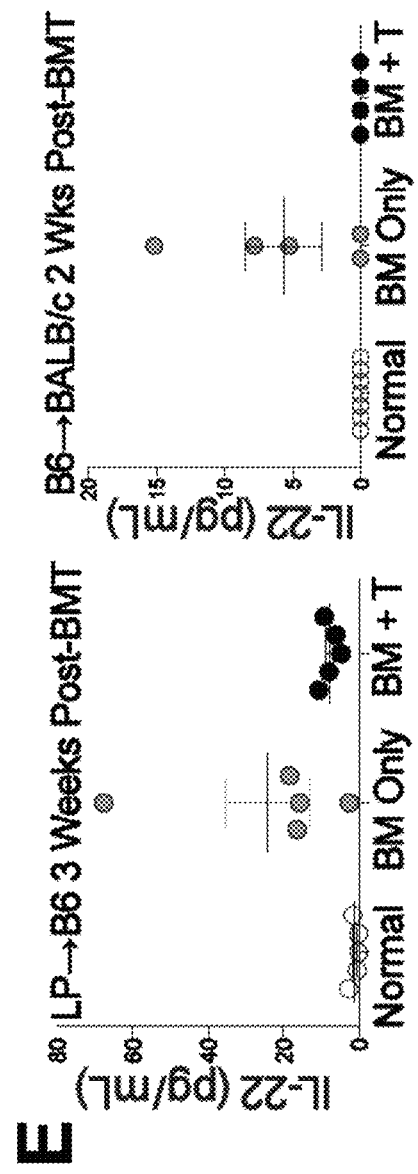
Figures 2F, 2G:
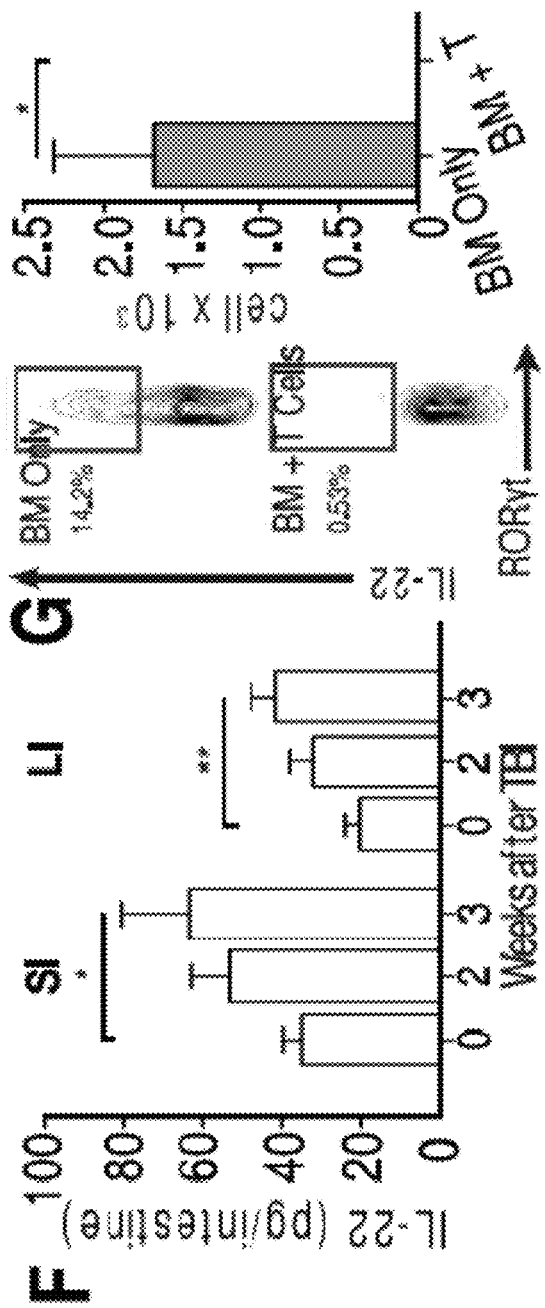

Expression of IL-22 was found within the GI tract (FIG. 2B) and serum (FIG. 2E) after allo-HCT. However, IL-22 levels were reduced during GVHD (FIGS. 2B, E). Intestinal IL-23, a dendritic cell-derived regulator of IL-22 expression, was also expressed post-HCT. IL-22-producing $CD45^+$ $CD3^-ROR\gamma t^+$ ILC were identified in the lamina propria after T cell-depleted (TCD) HCT (FIG. 2G). These ILC were host-derived $IL-7R^+CCR6^+NKp46^-$ lymphoid tissue inducer-like cells. Despite their radioresistance, IL-22-producing ILC were rapidly eliminated during GVHD (FIG.

2G). Therefore, host-derived IL-22 reduced GVHD mortality, but an IL-22 response to injury is blunted during GVHD due to elimination of host ILC.

Although host IL-22 deficiency increased GVHD (FIGS. 1A-C and 2A), there were no observable differences in donor lymphocyte intestinal infiltration or cytokine secretion in IL-22 KO recipients, indicating that the reduction in GVHD was unlikely due to manipulation of alloreactive donor immunity. Intestinal IL-22R expression was measured by fluorescence-activated cell sorting (FACS) with an observed increase of IL-22R on GI epithelium post-HCT.

Immunohistochemistry (IHC) and immunofluorescence (IF) indicated IL-22R expression within intestinal crypts where the ISC niche is located (FIGS. 3A-C). Allo-HCT were transplanted into Lgr5-LacZ reporter mice, which produced β-galactosidase downstream of Lgr5 to identify ISC. As evidence of ISC function, single $Lgr5^+$ crypt base columnar cells (CBC) were able to generate entire crypt structures in vitro and in vivo. A dramatic reduction of ISC during GVHD was observed (FIG. 3D). Furthermore, assessment of the ISC niche by IHC in non-reporter WT mice confirmed the loss of CBC/ISC during GVHD (FIG. 3E). Strikingly, IL-22 KO recipients demonstrated the greatest loss of CBC/ISC (FIG. 3E) and increased apoptosis of crypt epithelial cells (FIG. 3F) during GVHD, indicating that IL-22 protected ISC and progenitor cells. Finally, IL-22 KO mice with GVHD demonstrated decreased GI expression of the IL-22-regulated antimicrobial molecules Reg3γ and Reg3β and increased serum translocation of the non-absorbable carbohydrate FITC-dextran after oral challenge (FIG. 3G) indicating increased damage to the epithelial barrier.

Figure 12A:
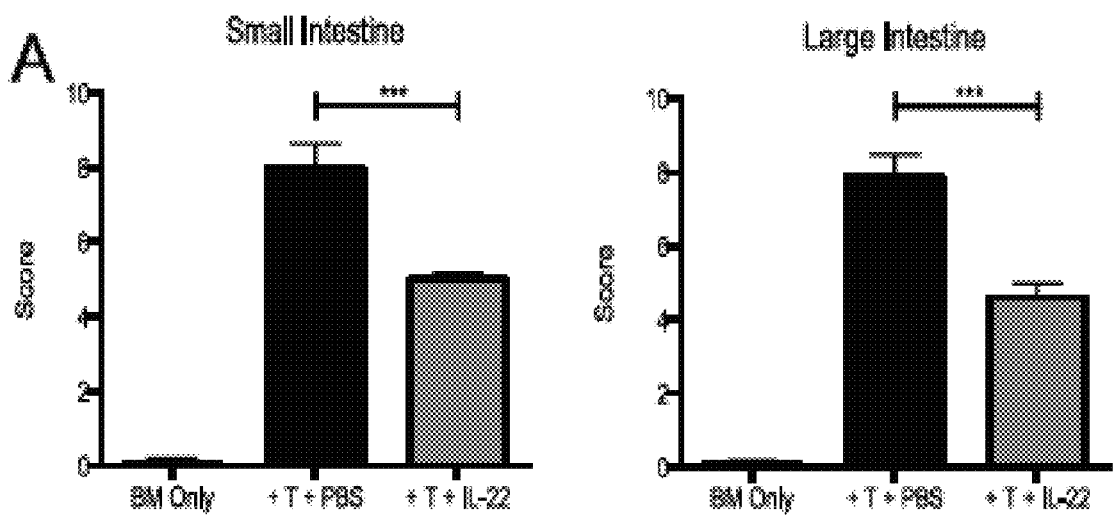
Figure 12B:
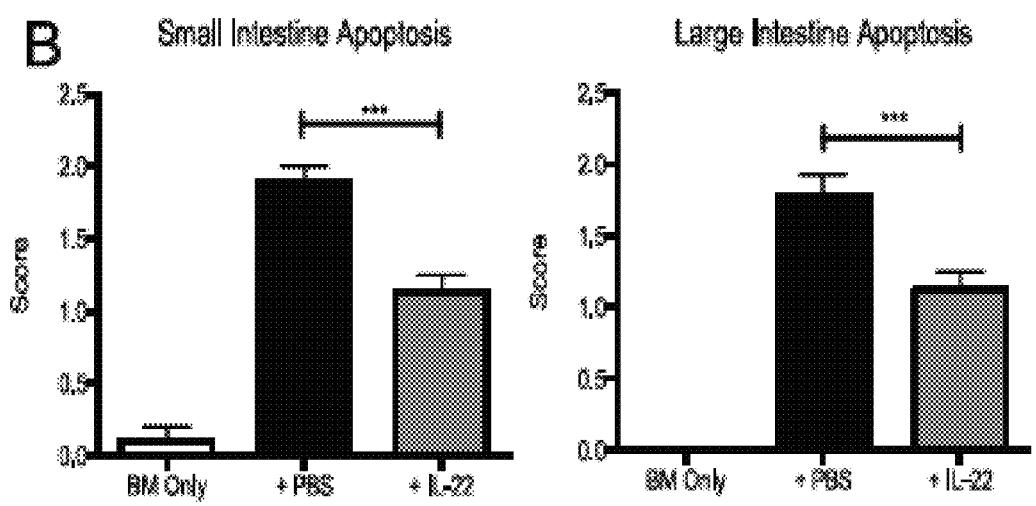
Figure 12C:
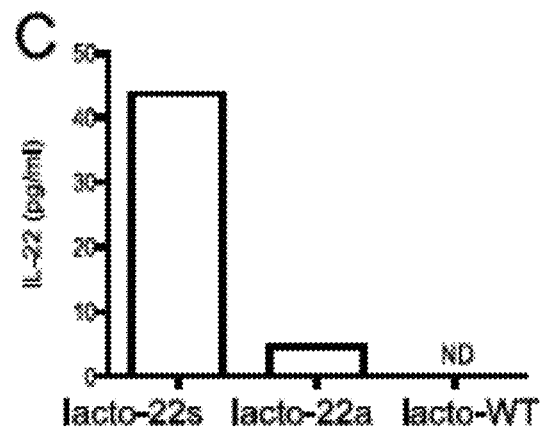
Figure 12D:
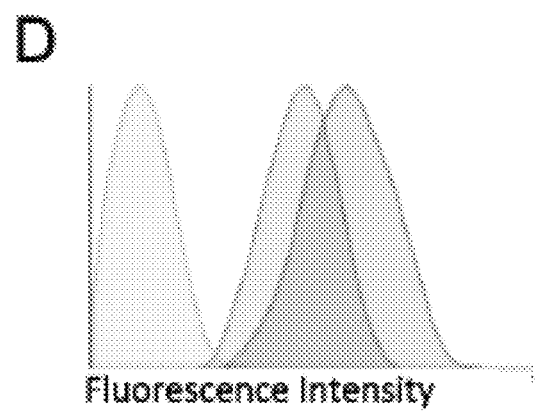

Therefore, GI damage led to induction of IL-23. IL-23 in turn can stimulate IL-22 production by ILC. This endogenous IL-22 protected the epithelium and the stem/progenitor cell compartment from inflammatory tissue damage. However, IL-22-producing ILC necessary for limiting tissue damage were lost during GVHD. As shown herein, administration of rIL-22 post HCT by intraperitoneal injection (for example, 4 ug/mouse daily) reversed the effects of ILC depletion and loss of IL-22 in GVHD pathology within the intestines as well as reduce apoptosis within intestinal crypts where the ISC/progenitor compartment is located (FIGS. 12A-B). However, for clinical use systemic cytokine administration is costly and may have unanticipated systemic effects. Therefore, the inventors made two strains of *Lactobacillus paracasei* that constitutively produced IL-22 (FIGS. 12C-D). One strain produces secreted IL-22 (lacto-22s) while the other strain produced IL-22 anchored to the bacterial cell surface (lacto-22a).

B. IL22+ Lactobacilli Treatment of GVHD.

Figure 12E:
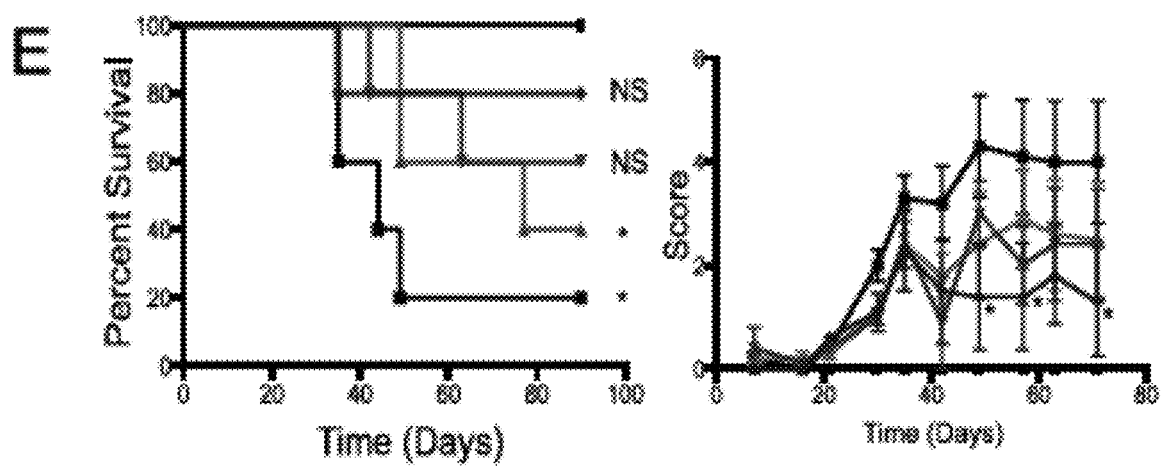

As described herein, after discovering that IL-22 deficiency leads to increased GVHD (FIGS. 1 through 3), IL-22-mediated reduction of GVHD (FIG. 12), and IL-22-dependent induction of antimicrobial molecules post-HCT, IL-22 was administered post-HCT using lacto-22s and lacto-22a bacteria of the present inventions as described herein. The two strains of *lactobacillus* were administered associated with HCT (FIG. 12E). Mice underwent allo-HCT with bone marrow and T cells to cause GVHD. Starting on the day of transplant, mice were gavaged with $10^8$-$10^9$ wild type *Lactobacillus paracsei* (lacto-WT), lacto-22s, or lacto-22a resuspended in PBS, or with PBS alone until day 30 post-HCT. GVHD led to significant mortality in mice gavaged with PBS. While there was a trend toward improved survival in mice receiving lacto-WT, these mice still suffered significant mortality due to GVHD.

In contrast, mice receiving lacto-22s or lacto-22a did not have significantly different mortality compared to mice transplanted without T cells. Furthermore, recipients of lacto-22s had significantly reduced clinical scores of GVHD, an assessment encompassing weight, fur quality, skin integrity, posture, and activity. While the change in weights of mice post-HCT can serve as a surrogate measure for GI GVHD, the systemic nature of these findings suggest that GI protection may be central to preventing systemic disease from GVHD.

T cell depleted MHC matched allo-HCT was done as described above and mice were gavaged daily with lacto-WT, lacto-22s, and lacto-22a. Additionally, PCR for IL-22 is contemplated to be performed from recipient intestinal pellets to confirm presence of lacto-22 in the GI tract. MHC matched allo-HCT model most closely matches transplants that are performed clinically in human patients, where transplant donors are selected preferentially based on MHC matching to the recipient. In addition, experiments will be performed where mice will be sacrificed three weeks post-HCT to assess GVHD pathology and crypt apoptosis. In order to directly test the effect of lacto-22 on ISC, transplants as described above will be made with Lgr5-LacZ mice as recipients to assess the elimination of Lgr5' ISC. Lacto-22 administration will be compared to rIL-22 for safety and reduction of GI pathology and mortality.

Effects of IL-22 Produced by *Lactobacillus* on Intestinal Epithelium.

Lacto-22 treatment of mice appeared to reduce GVHD mortality and symptoms. Therefore experiments are contemplated for effects on lacto-22 on intestinal epithelium by measuring systemic IL-22 in serum by ELISA. ELISA for IL-22 from homogenized tissue samples and assess downstream effects of IL-22 within the tissues by measuring intestinal phosphorylated STAT-3 by IHC and western blot. Finally, electron microscopy will be performed in an attempt to image if gavaged *lactobacillus* can penetrate into the epithelium. Alternatively, *lactobacillus* from the blood or tissue homogenates of transplanted mice will be cultured to determine if the bacteria are entering the systemic circulation. Lacto-22 carries a resistance gene for chloramphenicol to facilitate proper identification of lacto-22 under culture conditions.

Effects of Lacto-22 on Donor T Cells and Recipient Flora.

B6 HCT into BALB/c allo-HCT mice will be treated daily with a gavage of lacto-WT and lacto-22 as described above. Donor marrow will be derived from CD45.1 B6 and T cells will be derived from WT B6 (CD45.2+) to facilitate identification of donor T cells by flow cytometry. Donor T cell expansion in the spleen, mesenteric lymph nodes, and intestinal lamina propria eill be measured including the effector-to-regulatory T cell ratio. We will also assess donor T cell expression of activation/memory markers and cytotoxic effector molecules including Fas ligand. Serum and intracellular cytokine expression for inflammatory cytokines, and we will measure by PCR epithelial tissue expression of innate antimicrobial molecules induced by IL-22 (Reg3γ and Reg3β). As antimicrobials downstream of IL-22 may have effects on the flora and the presence of administered lactobacilli may themselves have profound effects on the flora, we will perform 16S rDNA sequencing as we have recently published in order to assess diversity of the microbiota after administration of lacto-22.

Effect of Lacto-22 on GVL.

Given the limitation of IL-22R expression to non-hematopoietic cells, lacto-22 should not suppress GVL or promote hematopoietic tumor growth. This line of experimentation is important for potential clinical translation of lacto-22. Preliminary experiments with IL-22 KO donor T cells or with WT T cells after rIL-22 treatment in vivo showed no observable differences in GVL capacity (FIGS. 8A-B). Therefore, effects of the lacto-22 on GVL can be measured by performing T cell replete HCT with standard tumor cell lines (A20, EL4). Mice can be monitored for tumor progression and related morbidity/mortality. In addition, tumor growth will be monitored by bioluminescence.

While experimentally efficient, HCT with tumor cell lines represents a model with questionable direct correlation to clinical transplant with de novo malignancies. We have thus developed a model of experimental GVL (FIG. 8C) against mixed lineage leukemia (MLL)-related acute myeloid leukemia (AMIL). Rearrangements involving the MLL gene are particularly relevant for transplant studies, as they are highly prevalent in therapy-related AML, carry a poor clinical prognosis, and are an indication for allo-HCT[31]. Following lacto-22 gavage, GVL will be measured against AML induced by transduction with MLL-AF9. This model of high-risk secondary leukemia reflects clinical disease more closely than tumor cell lines. Tumor progression could thus be monitored by transplant outcome and GFP reporter expression in peripheral blood, spleen, and marrow.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); mnol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); .degree. C. (degrees Centigrade); Gy (gray) and cGy (centigray).

Example I

This Example describes materials and methods used herein.

Materials and Methods

C57BL/6 (CD45.2 B6, H-2b), B6.SJL-Ptprca Pepcb/BoyJ (CD45.1 B6 congenic, H-2b), Il12b-/-B6, BALB/c (H-2d), and LP (H-2b) mice were obtained from the Jackson Laboratory. B6 and BALB/c Il22-/-mice were provided by Genentech, as was anti-IL-22 neutralizing antibody 8E11. Lgr5-LacZ and Lgr5-GFP B6 mice were provided by H. Clevers (Barker et al., 2007). BMT procedure was performed as previously described (Petrovic et al., 2004), with 850 cGy split-dosed lethal irradiation of BALB/c hosts receivingbone marrow (5×106), T cell-depleted with anti-Thy-1.2 and low-TOX-Mrabbit complement (Cedarlane Laboratories), or performed with 1100 cGysplit-dosed lethal irradiation of B6 hosts receiving T cell-depleted bonemarrow (5×106) as well. Donor T cells (typically 1×106B6 or 4×106 LP, unless otherwise specified) were prepared for transplantation by harvesting donor splenocytes and enriching for T cells by either nylon wool passage (routinely >70% T cell purity) or by Miltenyi MACS purification of CD5 (routinely >90% purity). Recipient mice were monitored for survival and clinical GVHD symptoms and were sacrificed for blinded histopathologic and flowcytometric analysis as previously described (Petrovic et al., 2004). Forchimeric experiments, CD45.1 B6 congenic mice were lethally irradiated andreconstituted with either wild-type or Il22-/-CD45.2 marrow. Three months later, donor reconstitution was confirmed by FACS of peripheral blood for CD45.1 versus CD45.2, and chimeric mice were irradiated again (900 cGy,split dose) and transplanted with LP marrow (10×106) and T cells (3×106). Mice.

C57BL/6 (CD45.2 B6, H-2b) and LP (H-2b) mice were obtained from Jackson Laboratory (Bar Harbor, USA). B6 Lgr5-LacZ and B6 lgr5-gfp-ires-CreERT2 (Lgr5-GFP) mice were kindly provided by H. Clevers. Mice were housed in micro-isolator cages, five per cage, in MSKCC pathogen-free facilities and received standard chow and autoclaved sterile drinking water. Mouse maintenance and procedures were done in accordance with the institutional protocol guideline of the Memorial Sloan Kettering Cancer Center (MSKCC) Institutional Animal Care and Use Committee.

Crypt Isolation and Cell Dissociation.

Isolation of intestinal crypts and the dissociation of cells for flow cytometry analysis were largely preformed as previously described. Briefly, after euthanizing the mice through $CO_2$ asphyxiation, and harvesting small and large intestine, the organs were opened longitudinally and washed. Small intestine has been incubated in ethylenediamine-tetraacetatic acid (EDTA) 5 mM for 60 min or 10 mM for 25 min (4° C.) to dissociate the crypts; large intestine was incubated in Collagenase Type 4 (Worthington) for 30 min (37° C.). The supernatant containing crypts was collected. For crypt disaggregation into single cells, the crypt pellet was further incubated in 1× trypLE express (Gibco, Life technologies) complemented with 0.8 KU/ml DNase1 (Roche). Isolated crypts for RNA extraction were resuspended in 1 ml of Trizol (invitrogen) and stored at −80° C.

Organoid Culture.

400 crypts per well were suspended in liquefied growth factor reduced Matrigel (Corning) (25% Advanced DMEM/F12 medium (Gibco); 75% growth factor reduced Matrigel) at 4° C. Then, they were plated in pre-warmed delta-surface Nunc 24-well plates in 50 µL drops for small intestine, 30 ul drops for Large intestine, each containing approximately 100-500 crypts. After the Matrigel drops polymerized, 500 ul complete crypt culture medium was added to small intestine crypt cultures (ENR-medium: advanced DMEM/F12 (Sigma), 2 mM L-glutamine (Sigma), 10 mM HEPES (Sigma), 100 U/ml penicillin/100 µg/ml streptomycin (Sigma), 1 mM N-acetyl cysteine (Sigma), 1× B27 supplement (Invitrogen,), 1×N2 supplement (Invitrogen), 50 ng/ml mEGF (Peprotech), 100 ng/ml mNoggin (Peprotech) and 10% human R-spondin-1 conditioned medium of hR-spondin-1-transfected HEK 293T cells. In some experiments evaluating budding, the concentration of hR-spondin-1 was lowered to 1.25-5%. Large intestine crypts were cultured in WENR-medium containing 50% of Wnt3a conditioned medium in addition to the aforementioned proteins and 1% Bovine serum Albumin (Sigma). For large intestine cultures 10 uM SB202190 (Sigma, Cat.nr.S7067) and ALK5 inhibitor (A83-01, Tocris) were added to the WENR. All plates were incubated at 37° C./5% $CO_2$ and the media was replaced every 2-3 days. Control wells were left untreated, and where applicable, treatment wells received different concentrations of recombinant murine (rm)IL-22 (Genscript) along with medium changes. Crypts were passaged at day seven by mechanically disrupting them with a seropipet, washing away the Matrigel by spinning down the crypts in excess medium, and replating them after reconstitution of the pellet in liquefied Matrigel. We also tested the effects of F-652, a recombinant human IL-22 dimer molecule provided by Evive Biotechnology (Shanghai) Ltd, China. In some experiments, organoids were cultured from crypts in the presence of Stattic (STAT three inhibitory compound, 6-Nitrobenzo[b]thiophene 1,1-dioxide; Tocris Bioscience).

Intestinal stem cells were isolated from LgR5-GFP mice using a modified crypt isolation protocol with 20 minutes of 30 mM EDTA3,4 followed by several strainer steps and a 5 min incubation with TrypLE and 0.8 under min to minute vortexing to make a single cells suspension. The Lgr5-GFPhigh cells were isolated by fluorescence-activated cell sorting. 5000 TLCs were plated in 30 uL growth factor reduced Matrigel drops and cultured in WENR containing 10 uM rho-kinase inhibitor Y-27632 in the medium and 1 uM Jagged 1 notch ligand (Anaspec) and Rhokinase inhibitor (10 uM) in the Matrigel. ISC cultures were cultured without Wnt from D4.

For innate lymphoid cell (LC) co-culture experiments, intestinal lymphocytes were isolated from the small intestine lamina propria. After washing small intestine fragments, 20 ml/mouse prewarmed EDTA/IEL solution (1×PBS with 5% FBS, 10 mM Hepes Buffer, 1% Pen/strep Corning, 1% L-glutamine (Gibco), 1 mM EDTA and 1 mM DTT was added, followed by placing the samples in a 37° C. shaker for 15 minutes. The samples were strained (100 uM) and put in a Collagenase solution (RPMI 1640, 5% FCS, 10 mM Hepes, 1% PS, 1% Glutamine and 1 mg/ml Collagenase A (Roche) and 1 u/ml DNAse 1 (Roche) and left for 10 minutes in the 37° C. shaker. Afterwards, the samples were centrifugated at 1500 rpm for five minutes and washed with RPMI solution without enzymes. After several washes, the cell suspension was transferred into a 40% Percoll solution (Percoll in RPMI), which is overlaid on a 80% Percoll solution. After spinning the interface containing the lamina propria mononuclear cells was aspirated and washed in medium. Then the cell suspension was stained with extracellular markers and Topro 3 for viability. ILCs were selected and sorted as Topro3−, B220−, CD11b−, CD11c−, CD45+, CD3+ and CD90.2+ cells. 1000 ILCs were plated with 400 crypts in the Matrigel per well. For co-cultures with ILCs rmIL-2 (1000 u/ml), rmIL-15 (10 ng/ml) and rmIL-7 (50 ng/ml) and rmIL-23 (50 ng/ml) were added to the ENR medium. Cocultures were compared to crypts cultured in the cytokine containing ENR without the ILCs present.

Bone Marrow Transplantation.

Bone marrow transplantation (BMT) procedures were performed as previously described. A minor histocompatibility antigen-mismatched BMT model (LP→B6, $H-2^b \rightarrow H-2^b$) was utilized. Female B6 WT mice were typically used as recipients for transplantation at an age of 8 to 10 weeks. Recipient mice received 1100 cGy of split-dosed lethal irradiation (550 cGy×2) 3-4 hours apart to reduce gastrointestinal toxicity. To obtain LP bone marrow cells from euthanized donor mice, the femur and tibia were harvested aseptically and the bone marrow canals washed out with sterile medium. Bone marrow cells were depleted of T cells by incubation with anti-Thy 1.2 and low-TOX-M rabbit complement (Cedarlane Laboratories). The T cell-depleted bone marrow was analyzed for purity by quantification of the remaining contaminating T cells. The contamination of T cells usually was about 0.2% of all leukocytes after a single round of complement depletion and 0.1% after a second round. The LP donor T cells were prepared by harvesting splenocytes aseptically from euthanized donor mice. T cells were purified using positive selection with CD5 magnetic Microbeads with the MACS system (Miltenyi Biotec). The purity of the cells was determined by flow cytometry and was routinely approximately 90%. Recipients typically received 5×106 bone marrow cells with or without 4×106 T cells per mouse unless otherwise specified via tail vein injection.

Mice were monitored daily for survival and weekly for graft vs. host disease (GVHD) scores with an established clinical GVHD scoring system (including weight, posture, activity, fur ruffling, and skin integrity) as previously described6. A clinical GVHD index with a maximum possible score of ten was then generated. Mice with a score of five or greater were considered moribund and euthanized by $CO_2$ asphyxia.

Cytokine Administration.

Recombinant murine IL-22 was purchased from GenScript and reconstituted as described by the manufacturer to a concentration of 40 g IL-22/1000 ul phosphate-buffered saline (PBS). Each mouse was treated with either 100 µl PBS or 100 µl PBS containing 4 g recombinant mouse IL-22 daily via intrapertitoneal injection. IL-22 administration was started day seven post-BMT. This schedule was based on the results of rIL-22 pharmacokinetics tested in untransplanted mice. For F-652 administration in vivo, mice were treated with PBS or 100 µg/kg F-652 subcutaneously every other day for ten weeks starting day seven post-BMT.

Histopathologic Analysis of GVHD Target Organs.

Mice were euthanized for organ analysis at D21 post-BMT using $CO_2$ asphyxiation. For histopathological analysis of GVHD, the small and large intestines were formalin-preserved, paraffin-embedded, sectioned, and stained with hematoxylin and eosin (H&E). A semi quantitative score consisting of 19 different parameters associated with GVHD was calculated, as described previously.

Paneth Cell and Stem Cell Histologic Staining.

For staining of Paneth cells, intestines were harvested from euthanized mice and formalin-preserved, paraffin-embedded, sectioned, and stained with a polyclonal rabbit anti-human lysozyme 3.2.1.17 (Dakocytomaion). For evaluation of stem cell numbers, small intestines from Lgr5-LacZ recipient mice that were transplanted with LP bone marrow (and T cells where applicable) were harvested. β-galactosidase (LacZ) staining was preformed as previously described by Barker et al. Washed 2.5 cm sized small intestine fragments were incubated with an ice-cold fixative, consisting of 1% formaldehyde, 0.02% NP40 and 0.2% gluteraldehyde. After removing the fixative, organs were stained for the presence of LacZ. Then the organs were formalin-preserved, paraffin-embedded, sectioned, and counterstained with Nuclear Fast Red (Vector).

Cytokine Multiplex Assay.

Spleen and small intestine were harvested from euthanized BMT recipients. Then organs were homogenized, spun down and the supernatant stored at −20° C. until used for cytokine analysis. The cytokine multiplex assays were performed on thawed samples with the mouse Th1/Th2/Th17/Th22 13plex FlowCytomix Multiplex kit (eBioscience) and performed according to the manufacturer's protocol.

Flow Cytometry.

For the in vivo experiments evaluating the effect of IL-22, lymphoid organs were harvested from euthanized mice and processed into single cell suspension. Cells were stained with the appropriate mixture of antibodies. For analysis of intracellular molecules an eBioscience Fixation/Permeabilization kit was used per the manufacturer's protocol for intracellular staining. After thorough washing, the cells were stained with intracellular and extracellular antibodies simultaneously. Fluorochrome-labeled antibodies for intracellular and extracellular staining were purchased from BD Pharmingen (CD4, CD8, CD24, CD25, CD45, α4β7, Ki-67, and P-STAT3 Y705), eBioscience (Foxp3), R&D (IL-22R), and Invitrogen (GFP). DAPI and Fixable Live/Dead Cell Stain Kits (Invitrogen) were used for viability staining. Paneth cells were identified based on bright CD24 staining and side scatter granularity as described by Sato et al. 7.

For flow cytometry of small intestine organoid cells, the ENR medium was removed and the crypts and Matrigel were resuspended in TrypLE for approximately eight minutes. After vigorously pipetting through a p200 pipette causing mechanical disruption, the crypt suspension was washed with 10 ml of DMEM/F12 medium containing 10% FBS and 0.8 KU/ml DNase1. Suspensions were then evaluated for percentage of GFP+ cells. Where applicable, the cells were directly stained or first fixed and permeabilized depending on the extra- or intracellular location of the target protein. All stainings with live cells were performed in PBS without Mg2+ and Ca2+ with 0.5% BSA. For 5-ethynyl-2'-deoxyuridine (EdU) incorporation experiments there was a 1 hour pre-incubation of EdU in the ENR medium of the intact organoid cultures before dissociating the cells with trypLE. Cells were stained using Click-it kits for imaging and flow cytometry (Life Technologies).

For phospho-STAT3 staining on organoids, prior to fixation with PFA4% (10 min 37° C.), the cells were stimulated as mechanically disrupted crypts (as for passaging) or as single cells (trypLE), for 20 minutes with 20 ng/ml IL-22 at 37° C. In some experiments, IL-22 stimulation was performed with single cell suspensions generated from freshly isolated crypts (not organoids). After obtaining a single cell suspension of stimulated and fixed cells, the samples were filtered (40 uM) and permeabilized with ice-cold (−20° C.) methanol. Fix/permed cells were rehydrated with PBS and thoroughly washed with PBS before staining, Staining with anti-phospho-STAT3, anti-GFP, and/or cell surface markers was performed for 30 minutes at 4° C. All flow cytometry was performed on a LSR II cytometer (BD Biosciences) using FACSDiva (BD Biosciences), and the data were analyzed with FlowJo software (Treestar).

Organoid Measurement.

Organoid numbers per well were counted by light microscopy to evaluate growth efficiency on culture day seven. For size evaluation, two-dimensional brightfield microscopy photographs were taken using a MetaMorph Widefield Live imaging system microscope with 5× (0.25 NA DRY) and 10× (0.3 NA DRY) Zeiss objectives, presenting the largest horizontal cross section of each organoid. The area and perimeter of each cross section were measured with MetaMorph Software.

qPCR

For quantitative (q)PCR, segments of small intestine or isolated crypts were harvested from euthanized mice and stored at −80° C. RNA was extracted from those tissues and stored at −20° C. Alternatively, RNA was isolated from organoids after in vitro culture. Reverse transcription-PCR was preformed with a Quanti-Tec reverse transcription kit (QIAGEN). Specific primers were obtained for real time PCR from Applied Biosystems as follows: Beta-actin: Mm01205647_g1; HPRT: Mm00446968_m1; Reg3β: Mm00440616_g1; Reg3γ: Mm00441127_m1; WNT3: Mm00437336_m1 and EGF: Mm00438696_m1; Rspo3: Mm00661105_m1; Axin2: Mm00443610_m1; Beta-catenin: Mm00483039_m1. qPCR was performed on a Step-One Plus (Applied Biosystems) with TaqMan Universal PCR Master Mix (Applied Biosystems). Relative amounts of mRNA were calculated by the comparative ΔC(t) method with beta-Actin or HPRT as housekeeping genes.

Statistics and Software.

All bars and error bars represent the means+SEM for the various groups. For the comparisons of two groups, a t-test or nonparametric U test was performed. ANOVA was utilized for comparisons of more than two groups. All statistics were calculated and display graphs were generated using Graphpad Prism. All experiments were performed at least twice with at least 3-5 mice in each group.

Histopathologic Analysis of GVHD Target Organs.

GVHD mice were sacrificed, and the small intestine, large intestine, andliver were removed, formalin-preserved, paraffin-embedded, sectioned, andstained with hematoxylin and eosin (H&E). Scoring was performed as previously described (Petrovic et al., 2004).

Tissue Analyses and Flow Cytometry. Lymphoid organs from GVHD mice were processed into single-cell suspensions, and lamina propria lymphocytes were isolated after dissociation of theepithelium and digestion in DNaseI (Roche) and Collagenase D (Roche). Surface staining was performed with the corresponding cocktail of antibodies, and an eBioscience Fixation/Permeabilization kit was used per the manufac-turer's protocol for intracellular staining. FACS for IL-22R (rat-anti-mouseIL-22R a antibody 496514, R&D Systems) included both surface and intracellular staining. Intracellular cytokine staining was performed with anti-IL-22 (1H8PWSR, eBioscience), anti-IFN-g (XMG1.2, BD PharMingen), or anti-TNF-a (MP6-XT22, BD PharMingen) after 5 hr of restimulation with BD GolgiPlug (1 ul/ml) and IL-23 (40 ng/ml) for IL-22 expression or phorbol-12-myris-tate-13-acetate (50 ng/ml) and ionomycin (500 ng/ml) for IFN-g and TNFexpression. IL-22 and IL-23 ELISA were performed per the manufacturer's protocol (BioLegend) on either homogenates from small and large intestines or on supernatants from intestines that were cultured at 37° C. overnight in RPMI with FBS. Immunohistochemistry, Immunofluorescence, TUNEL, LacZ, and ISC HistologyIntestines were harvested from normal mice, formalin-fixed, and stained with rat-anti-mouse IL-22R a antibody 496514 (R&D Systems) versus isotypecontrol and/or polyclonal rabbit anti-human lysozyme 3.2.1.17 (Dako-cytoma-tion). Immunofluorescence secondary staining was performed with AF488 for IL-22R and AF568 for lysozyme. TUNEL assay was performed on formalin-fixed/paraffin-embedded tissue as described by Gavrieli et al. (1992). For Lgr5-LacZ transplants, 2.5 cm segments of ileum were obtained, and staining for presence of beta-galactosidase (LacZ) was performed as per Barker et al. (2007). In brief, small intestines were fixed in 1% formaldehyde, 0.2% glutaral-dehyde, and 0.02% NP40 in PBS and then incubated with b-galactosidases ubstrate. Tissues were then fixed again in 4% PFA in PBS and paraffin-embedded, and sections were counterstained with Nuclear Fast Red (Vector). For assessing ISCs in nonreporter mice, crypt base columnar intestinal stemcells were identified as reported by their morphology and their location at the crypt base between Paneth cells (Barker et al., 2007). Quantitative PCRReverse transcription-PCR was done with a QuantiTect reverse transcription kit (QIAGEN). For real-time PCR, specific primer and probe sets were obtained from Applied Biosystems as follows: Beta-actin: Mm01205647_g1, Reg3b: Mm00440616_g1, and Reg3g: Mm00441127_m1. PCR was done on ABI7500 (Applied Biosystems) with TaqMan Universal PCR Master Mix (AppliedBiosystems). Relative amounts of Reg3g and Reg3b mRNA were calculated by the comparative DC (t) method.

Statistics. Bars and error bars represent the means+SEM, respectively, for the various groups. Survival data were analyzed with the Mantel-Cox log-rank test. For nonsurvival pointwise analyses, unpaired t test was used for comparisons between two experimental groups, or nonparametric Mann-Whitney U test was used for non-Gaussian distributions, and ANOVA was used for comparisons with more than two groups. Survival transplants were performed with 10-38 mice per group, and all other experiments were performed at least twice with at least six mice per group.

Both MHC mismatched and minor histocompatibility antigen (miHA) mismatched transplants are performed to model both highly aggressive GVHD and clinically relevant transplant scenarios. Recipient mice are conditioned with lethal TBI as the pharmacokinetics of high dose chemotherapy are difficult to control experimentally. Recipients are then transplanted with T cell-depleted (TCD) marrow, which is supplemented with magnetic-bead-purified T cells to control for the effects of GVHD. Recipient mice are monitored post-transplant for clinical signs of GVHD (including weight, activity, posture, fur, and skin integrity) in accordance with MSKCC IACUC, and recipients are routinely sacrificed between 2-3 weeks post-transplant to evaluate T cell function and GVHD pathology. Statistical analyses will be performed with Sean Devlin, biostatistician for the MSKCC BMT service. In general, transplants will be performed with at least five mice per group, and all experiments will be repeated at least once. Comparisons between two groups will be made with nonparametric U tests. Experiments with more than two groups will be evaluated by ANOVA.

Organoid culture: Crypts were isolated from the small and LI from intestinal epithelium and cultured in semisolid medium in the presence of stem cell growth factors (R-spondin1, EGF, noggin for SI; R-spondin1, EGF, noggin, HGF, and Wnt3a for LI). As each crypt contains a functional stem cell compartment with ISCs and supportive niche cells, crypts cultured ex vivo grow into organoids with crypt buds that recapitulate the in vivo intestinal organization with crypt-villus structures and central lumens (FIG. 6). Additionally, as evidence of their ISC capacity, single Lgr5+ cells from SI and LI grown in this fashion are able to generate their own niche cells and form organoids from single cells[38,39]. Allo-BMTs were done as described and SI and LI crypts were isolated from recipients without GVHD (TCD marrow alone) and recipients with GVHD (marrow+T cells). Crypts will be harvested on days 1, 3, 5, 7, 10, and 14 post-BMT to evaluate the kinetics of damage to functional stem/progenitor cell niche. In addition, Lgr5-GFP reporter mice will be as transplant recipients so that single ISCs can be isolated by FACS post-BMT and cultured in vitro to evaluate the function of isolated ISCs in GVHD. This will provide a functional read out of the stem cell niche and specifically ISCs in GVHD.

Example II

Host-derived IL-22 is important for limiting mortality and GVHD pathology post-transplant.

Elimination of recipient IL-22 increases mortality post-transplant: Given the protective role reported for IL-22 in GI tissue damage, we began to assess the function of IL-22 post-BMT.

IL-22 knock out (KO) recipients demonstrated increased mortality following both minor (FIG. 1A) and major (FIG. 1B) antigen-mismatched BMT, as did wild-type (WT) recipients treated systemically with an anti-IL-22 neutralizing antibody (FIG. 1C). Deficiency of IL-22 in donor marrow (FIG. 1D) or T cells (FIG. 1E) had no observable impact on outcome. Reduced intensity BMT (lower T cell and radiation doses) into hematopoietic chimeras indicated that IL-22 deficiency limited to the host hematopoietic compartment increased GVHD mortality (FIG. 1F), transplantation into IL-22 KO recipients led to increased histopathologic evidence of GI GVHD (FIG. 2A).

IL-22 is expressed post-BMT and reduced during GVHD: We next identified expression of IL-22 within the GI tract (FIGS. 2B-C), thymus (FIG. 2D), and serum (FIG. 2E) after allo-BMT. However, IL-22 levels were reduced during GVHD (FIGS. 2B-E). Tissue IL-22 expression was induced after total body irradiation (TBI) without BMT (FIGS. 2D,F), and intestinal IL-23, a dendritic cell-derived[30] regulator of IL-22 expression[31-34], was also expressed post-BMT and after TBI without BMT. IL-22-producing CD45+CD3− RORγt+ ILCs were identified in the lamina propria after T cell-depleted (TCD) BMT (FIG. 2G). These ILCs were host-derived IL-7R+CCR6+NKp46− lymphoid tissue inducer-like cells, and they comprised over 50% of lamina propria ILCs even three months after BMT-TCD. Other intestinal IL-22-producers were not identified post-BMT. Despite their radioresistance and long-term persistence after BMT-TCD, IL-22-producing ILCs were rapidly eliminated during GVHD (FIG. 2G). These data indicate that a) IL-22 is expressed post-BMT but reduced during GVHD due to elimination of host ILCs and b) host-derived IL-22 reduces mortality post-BMT.

ISCs express IL-22R: Although host IL-22 deficiency increased GVHD (FIGS. 1-2A), no observable differences were found in donor lymphocyte intestinal infiltration or cytokine secretion in IL-22 KO recipients, indicating that the reduction in GVHD was not due to manipulation of alloreactive donor immunity. To identify the direct targets of IL-22, we assessed intestinal IL-22R expression by fluorescence-activated cell sorting (FACS) and observed increased IL-22R on GI epithelium post-BMT.

Immunohistochemistry (IHC) and immunofluorescence (IF) indicated IL-22R expression within intestinal crypts where the ISC niche is located (FIGS. 3A-C). ISC expression of IL-22R was confirmed by FACS of purified ISCs from Lgr5-GFP reporter mice (see FIG. 7A).

ISCs are lost in GVHD, and elimination of IL-22 leads to increased loss of ISCs during GVHD: To determine if ISCs could be targets of GVHD, we performed allo-BMT into Lgr5-LacZ reporter mice, which produce β-galactosidase downstream of Lgr5 to identify ISCs[8]. As evidence of ISC function, single Lgr5+ CBC cells are able to generate entire crypt structures in vitro and in vivo. Consistent with reported findings, we observed a dramatic reduction of ISCs during GVHD (FIG. 3D). Furthermore, assessment of the ISC niche by IHC in non-reporter WT mice confirmed the loss of CBC ISCs during GVHD (FIG. 3E). Strikingly, IL-22 KO recipients demonstrated the greatest loss of CBC ISCs (FIG. 3E) and increased apoptosis of crypt epithelial cells (FIG. 3F) during GVHD, indicating that IL-22 protects ISCs and progenitors. Finally, IL-22 KO mice with GVHD demonstrated decreased GI expression of the IL-22-regulated antimicrobial molecules Reg3γ and Reg3β and increased serum translocation of the non-absorbable carbohydrate FITC-dextran after oral challenge (FIG. 3G), indicating increased damage to the GI epithelial barrier.

Administration of IL-22 preserves ISCs in GVHD and reduces GVHD pathology: Given the reduction of IL-22 expression in GVHD and the exacerbated loss of ISCs in GVHD with IL-22 deficiency, we next examined the effect of IL-22 administration in GVHD. We found that daily administration of rmIL-22 (4 ug IP starting day +7) led to decreased GVHD pathology in recipient SI, LI, and liver three weeks post-BMT (FIG. 4A); no pathologic difference was observed in the skin (FIG. 4B). Recipients of rIL-22 had decreased intestinal crypt apoptosis (FIG. 4C) with no difference in intestinal inflammatory cytokine levels. To assess the effects of IL-22 administration on the ISC compartment, we performed LP into B6 allo-BMT using Lgr5-LacZ ISC reporter mice. Recipients treated with rIL-22 demonstrated increased numbers of Lgr5+ ISCs three weeks post-BMT during active GVHD with no immunosuppression (FIG. 4D). Furthermore, we found increased ISC proliferation after IL-22 treatment in GVHD using Lgr5-GFP reporter (see FIG. 7B).

Figure 4F:
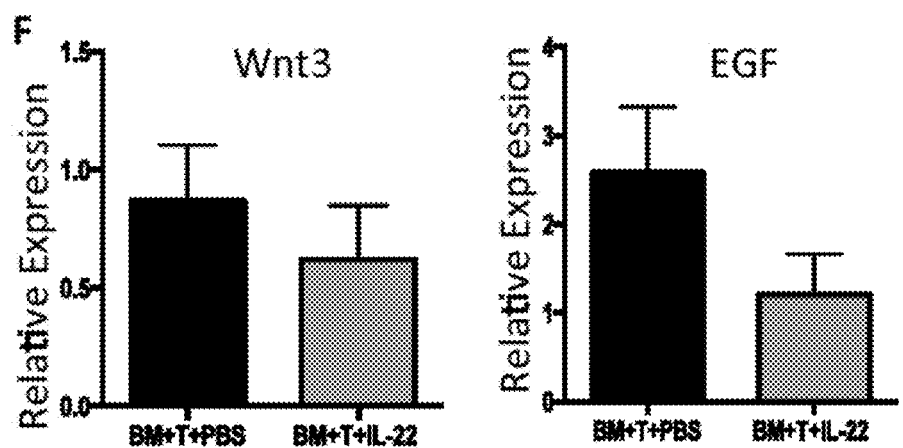
Figure 4G:
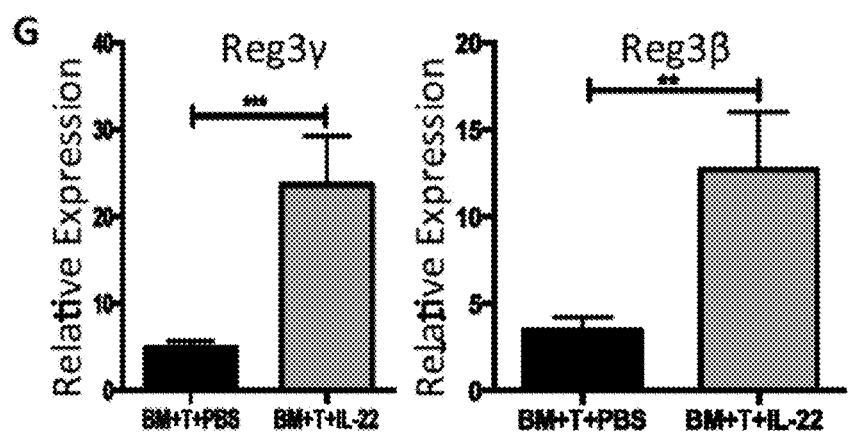

Administration of IL-22 augments ISC function without improving the ISC niche: Given the loss of ISCs we observed in GVHD, we sought to evaluate the Paneth cells that constitute the ISC niche in normal epithelial maintenance. Similar to what was reported in aggressive MHC-mismatched GVHD, we observed a reduction in Paneth cells in a minor mismatch GVHD model (FIG. 4E). However, although IL-22 administration increased the recovery of Lgr5+ ISCs in GVHD, no differences in Paneth cell numbers was observed after administration of IL-22 (FIG. 4E). Additionally, there was no difference in Wnt3 or EGF mRNA expression, arguing that the stem cell benefit after IL-22 administration was not due to improvement in ISC niche function (FIG. 4F). In contrast, IL-22 treatment led to increased Reg3γ and Reg3β expression (FIG. 4G), suggesting a potential antimicrobial benefit of IL-22 administration.

Summary: Our preliminary data reveal reciprocal networks between epithelium and the immune system, where GI tissue damage leads to induction of IL-23, which can stimulate IL-22 production by ILCs. This IL-22 protects the epithelium and the ISC compartment from inflammatory tissue damage. However, the IL-22-producing ILCs necessary for promoting ISC function are lost during GVHD. This indicates that GVHD leads to damage of the ISC compartment and its ability to mediate epithelial regeneration after tissue damage. This also suggests a potential therapeutic approach for augmenting ISC function in GVHD by replacing the lost IL-22. However, effective translation of these findings requires a detailed understanding of the normal intestinal homeostasis post-transplant, the damage inflicted upon ISCs directly and upon their Paneth cell niche, and the effect of IL-22 on ISCs and their progenitors.

Example III

Daily IP administration with rIL-22.

A clinically modeled LP into C57BL/6 (B6) minor antigen mismatched model with T cell-depleted marrow and MACS-purified T cells transplanted into lethally irradiated mice. Recipients were treated daily with PBS or 4 ug murine recombinant (r)IL-22 delivered via intraperitoneal (IP) injection starting day 7 post-HCT. This schedule was based on the results of rIL-22 pharmacokinetics tested in untransplanted mice.

Daily IP administration with rIL-22 led to decreased GVHD pathology in recipient small intestine, large intestine, and liver three weeks post-HCT (FIG. 9, p<0.001). No differences were observed in skin histopathology, consistent with our previous finding that IL-22-deficient recipients demonstrated equivalent skin GVHD. Further assessment of the intestinal pathology indicated that recipients of rIL-22 had decreased intestinal crypt apoptosis in both small and large intestine (p<0.01) with no difference in intestinal lymphocytic infiltration, suggesting that the decrease in GVHD was due to direct effects of IL-22 on the epithelium. Furthermore, no differences were observed in splenic T cell expansion or in GI cytokine expression, including a multi-plex panel of inflammatory cytokines.

Example IV

IL-22 administration effects on the intestinal stem cells (ISC) compartment.

LP into B6 allo-HCT using Lgr5-LacZ ISC reporter mice. Recipients treated with rIL-22 demonstrated increased numbers of Lgr5+ ISC three weeks post-HCT during active GVHD with no immunosuppression (FIG. 10, p<0.05). Preliminary evidence with Lgr5-GFP reporter mice suggested increased ISC Ki-67 staining and thus increased ISC proliferation following IL-22 administration. Small intestine qPCR after IL-22 treatment demonstrated increased expression of Reg3γ (p<0.001) and Reg3β (p<0.01), suggesting a potential antimicrobial benefit of IL-22 administration. However, there was no difference in Wnt3 or EGF expression, arguing that the stem cell benefit after IL-22 administration was not due to improvement in ISC niche function.

Example V

IL-22 administration to B6 into BALB/c tumor challenge recipients did not limit GVL.

IL-22R expression was not found in hematopoietic cells. Therefore, luciferase+A20 tumor cell bioluminescence was monitored to follow the GVT effect mediated by B6 T cells transplanted into BALB/c tumor challenge recipients treated with rIL-22.

Example VI

IL-22 administration improved peripheral T cell reconstitution even during active GVHD.

FVB MHC-mismatched transplant bone marrow was transplanted into BALB/c with Rag2-GFP marrow and WT T cells. IL-22 administration as described herein, increased the development of donor marrow-derived CD4 and CD8+ thymic emigrants four weeks post-HCT (FIG. 11, p<0.01).

Example VII

Uses of IL-22+ lactobacilli of the present inventions and effects of IL-22+ lactobacilli on GVHD and GI tissue damage post-HCT.

This Example shows results of endogenous loss of IL-22 production in GVHD (section A) along with an reduction of GVHD tissue damage by administration of IL-22+ lactobacilli. As shown in section B. below, *Lactobacillus* administration was shown to reduce experimental GVHD.

*Lactobacillus paracasei* is a normal constituent of human GI flora. Therefore the inventors contemplated the use of *Lactobacillus paracasei* to deliver therapeutic doses of exogenous IL-22 for providing additional therapeutic benefits.

A. Experimental Results of HCT in Mice Expressing Reduced Endogenous IL-22.

IL-22−/− KO recipients of HCT demonstrated increased mortality following both minor (FIG. 1A) and major (FIG. 1B) antigen-mismatched HCT, as did wild-type (WT) recipients treated systemically with an anti-IL-22 neutralizing antibody (FIG. 1C). Transplantation into IL-22 KO recipients led to increased histopathologic evidence of GI and hepatic GVHD (FIG. 2A). Therefore, host-derived IL-22 effected mortality and post-transplant GVHD pathology.

Expression of IL-22 was found within the GI tract (FIG. 2B) and serum (FIG. 2E) after allo-HCT. However, IL-22 levels were reduced during GVHD (FIGS. 2B, E). Intestinal IL-23, a dendritic cell-derived regulator of IL-22 expression, was also expressed post-HCT. IL-22-producing $CD45^+$ $CD3^-ROR\gamma t^+$ ILC were identified in the lamina propria after T cell-depleted (TCD) HCT (FIG. 2G). These ILC were host-derived $IL-7R^+CCR6^+NKp46^-$ lymphoid tissue inducer-like cells. Despite their radioresistance, IL-22-producing ILC were rapidly eliminated during GVHD (FIG. 2G). Therefore, host-derived IL-22 reduced GVHD mortality, but an IL-22 response to injury is blunted during GVHD due to elimination of host ILC.

Although host IL-22 deficiency increased GVHD (FIGS. 1 and 2A), no differences were observed in donor lymphocyte intestinal infiltration or cytokine secretion in IL-22 KO recipients, indicating that the reduction in GVHD was not due to manipulation of alloreactive donor immunity. Intestinal IL-22R expression was measured by fluorescence-activated cell sorting (FACS) with an observed increase of IL-22R on GI epithelium post-HCT.

Immunohistochemistry (IHC) and immunofluorescence (IF) indicated IL-22R expression within intestinal crypts where the ISC niche is located (FIGS. 3A-C). Allo-HCT were transplanted into Lgr5-LacZ reporter mice, which produced β-galactosidase downstream of Lgr5 to identify ISC. As evidence of ISC function, single $Lgr5^+$ crypt base columnar cells (CBC) were able to generate entire crypt structures in vitro and in vivo. A dramatic reduction of ISC during GVHD was observed (FIG. 3D). Furthermore, assessment of the ISC niche by IHC in non-reporter WT mice confirmed the loss of CBC/ISC during GVHD (FIG. 3E). Strikingly, IL-22 KO recipients demonstrated the greatest loss of CBC/ISC (FIG. 3E) and increased apoptosis of crypt epithelial cells (FIG. 3F) during GVHD, indicating that IL-22 protected ISC and progenitor cells. Finally, IL-22 KO mice with GVHD demonstrated decreased GI expression of the IL-22-regulated antimicrobial molecules Reg3γ and Reg3β and increased serum translocation of the non-absorbable carbohydrate FITC-dextran after oral challenge (FIG. 3G) indicating increased damage to the epithelial barrier.

Therefore, GI damage led to induction of IL-23. IL-23 in turn can stimulate IL-22 production by ILC. This endogenous IL-22 protected the epithelium and the stem/progenitor cell compartment from inflammatory tissue damage. However, IL-22-producing ILC necessary for limiting tissue damage were lost during GVHD. As shown herein, administration of rIL-22 post HCT by intraperitoneal injection (for example, 4 ug/mouse daily) reversed the effects of ILC depletion and loss of IL-22 in GVHD pathology within the intestines as well as reduce apoptosis within intestinal crypts where the ISC/progenitor compartment is located (FIGS. 12A,B). However, for clinical use systemic cytokine administration is costly and may have unanticipated systemic effects. Therefore, the inventors made two strains of *Lactobacillus paracasei* that constitutively produced IL-22 (FIGS. 12C,D). One strain produces secreted IL-22 (lacto-22s) while the other strain produced IL-22 anchored to the bacterial cell surface (lacto-22a).

B. Result of IL22+ Lactobacilli Treatment of GVHD.

As described herein, after discovering that IL-22 deficiency lead to increased GVHD (FIGS. 1 through 3), IL-22-mediated reduction of GVHD (FIG. 12), and IL-22-dependent induction of antimicrobial molecules post-HCT, IL-22 was administered post-HCT using lacto-22s and lacto-22a bacteria of the present inventions as described herein. The two strains of *lactobacillus* were administered associated with HCT (FIG. 12E). Mice underwent allo-HCT with bone marrow and T cells to cause GVHD. Starting on the day of transplant, mice were gavaged with $10^8$-$10^9$ wild type *Lactobacillus paracsei* (lacto-WT), lacto-22s, or lacto-22a resuspended in PBS, or with PBS alone until day 30 post-HCT. GVHD led to significant mortality in mice gavaged with PBS. While there was a trend toward improved survival in mice receiving lacto-WT, these mice still suffered significant mortality due to GVHD.

In contrast, mice receiving lacto-22s or lacto-22a did not have significantly different mortality compared to mice transplanted without T cells. Furthermore, recipients of lacto-22s had significantly reduced clinical scores of GVHD, an assessment encompassing weight, fur quality, skin integrity, posture, and activity. While the change in weights of mice post-HCT can serve as a surrogate measure for GI GVHD, the systemic nature of these findings suggest that GI protection may be central to preventing systemic disease from GVHD.

T cell depleted MHC matched allo-HCT was done as described above and mice were gavaged daily with lacto-WT, lacto-22s, and lacto-22a.

Example VIII

Using clinically modeled LP→C57BL/6 (B6) minor antigen-mismatched HSCT ($H-2^b$→$H-2^b$), we found that daily treatment with recombinant murine (rm) IL-22 (4 ug, intraperitoneal injection) starting day seven after transplant led to reduced intestinal pathology from GVHD without altering alloreactive immunity. Both overall GVHD pathology and epithelial apoptosis scores were significantly lower three weeks post-BMT in rmIL-22-treated mice with GVHD compared to PBS-treated controls ($p<0.001$). We observed that mice treated with rmIL-22 (and no pharmacologic immunosuppression) had increased numbers of Lgr5+ISCs and significantly greater ISC proliferation ($p<0.01$). This was not due to IL-22-dependent changes in the ISC niche, as Paneth cell numbers, Paneth cell-derived growth factors (EGF, Wnt3), and stroma-derived growth factors (Rspo3) were all unchanged after IL-22 administration. However, the antimicrobial proteins Reg3β and Reg3γ were both upregulated by qPCR in small intestine (SI) of rmIL-22-treated mice ($p<0.01$ and $p<0.001$ respectively), although this did not result in consistent changes in the gut microbial flora.

To evaluate direct effects on epithelial regeneration, we performed intestinal organoid culture assays in the presence of IL-22. Organoids generated from SI and large intestine (LI) crypts of wild-type B6 mice demonstrated substantially increased size after seven days of culture with IL-22 ($p<0.001$, SI, FIG. 1A; $p<0.05$, LI). Coculturing crypts with innate lymphoid cells (ILC), potent producers of IL-22 in vivo, led to increased organoid size as well. Furthermore, culture with IL-22 significantly increased organoid budding (new crypt formation), resulting in increased organoid expansion with serial passaging in the presence of IL-22 (1 ng/ml) suggesting that IL-22 could directly increase ISC expansion. Indeed, IL-22 culture led to increased organoid EDU incorporation and expansion of Lgr5+ISCs after culture of SI crypts from Lgr5-GFP reporter mice (p<0.001, FIG. 1). Demonstrating a direct effect on ISCs, IL-22 led to STAT3 phosphorylation specifically in Lgr5+ cells and resulted in increased budding of organoids cultured from isolated single SI ISCs after only four days in culture (p<0.01).

To investigate the translational potential for use in humans, we tested a human IL-22 dimer molecule (F-652, Evive Biotechnology (Shanghai) Ltd.) on mouse intestinal crypts and found that F-652 significantly increased the size of SI and LI organoids. Using the LP→B6 allo-HSCT model described above, we found that every other day subcutaneous (SQ) treatment with 100 ug/kg F-652 starting day seven post-BMT led to significant improvement in both clinical GVHD score (P<0.0001) and survival (p<0.05, FIG. 1C).

IL-22 and innate lymphoid cells can bridge immune function and tissue regeneration by acting directly on epithelial stem cells. IL-22 and F-652 therapy may represent a novel approach to promote intestinal recovery in patients with GVHD without increasing post-transplant immunodeficiency.

In summary, IL-22 administration was discovered to reduce intestinal pathology, improve ISC recovery, and promote donor marrow-derived T cell development during GVHD. Surprisingly, IL-22 administration did not impair GVL. These results suggest that post-transplant IL-22 administration represents a novel strategy to protect intestinal epithelium and improve immune reconstitution after allo-HCT.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention should not be unduly limited to such specific embodiments. Indeed, various modifications of the described modes for carrying out the invention which are obvious to those skilled in medicine, diagnostics, immunology, cell biology, molecular biology or related fields are intended to be within the scope of the present invention and the following Claims.

The following references are herein incorporated by reference in their entirety:

1. Jenq, R. R. & van den Brink, M. R. Allogeneic haematopoietic stem cell transplantation: individualized stem cell and immune therapy of cancer. *Nat Rev Cancer* 10, 213-221.
2. CIBMTR Newsletter. 13 (2007).
3. Hill, G. R. & Ferrara, J. L. The primacy of the gastrointestinal tract as a target organ of acute graft-versus-host disease: rationale for the use of cytokine shields in allogeneic bone marrow transplantation. *Blood* 95, 2754-2759 (2000).
4. Wingard, J. R. et al. Long-term survival and late deaths after allogeneic hematopoietic cell transplantation. *J Clin Oncol* 29, 2230-2239.
5. Shlomchik, W. D. Graft-versus-host disease. *Nat Rev Immunol* 7, 340-352 (2007).
6. Takashima, S. et al. The Wnt agonist R-spondin regulates systemic graft-versus-host disease by protecting intestinal stem cells. *J Exp Med* 208, 285-294 (2011).
7. Sale, G. E. Does graft-versus-host disease attack epithelial stem cells? *Mol Med Today* 2, 114-119 (1996).
8. Barker, N. et al. Identification of stem cells in small intestine and colon by marker gene Lgr5. *Nature* 449, 1003-1007 (2007).
9. Sato, T. et al. Paneth cells constitute the niche for Lgr5 stem cells in intestinal crypts. *Nature* 469, 415-418 (2010).
10. Carmon, K. S., Lin, Q., Gong, X., Thomas, A. & Liu, Q. LGR5 interacts and cointernalizes with Wnt receptors to modulate Wnt/beta-catenin signaling. *Mol Cell Biol* 32, 2054-2064 (2012).
11. Glinka, A. et al. LGR4 and LGR5 are R-spondin receptors mediating Wnt/beta-catenin and Wnt/PCP signalling. *EMBO Rep* 12, 1055-1061 (2011).
12. de Lau, W. et al. Lgr5 homologues associate with Wnt receptors and mediate R-spondin signalling. *Nature* 476, 293-297 (2011).
13. Simons, B. D. & Clevers, H. Stem cell self-renewal in intestinal crypt. *Exp Cell Res* (2011).
14. Barker, N., van Oudenaarden, A. & Clevers, H. Identifying the stem cell of the intestinal crypt: strategies and pitfalls. *Cell Stem Cell* 11, 452-460 (2012).
15. Eriguchi, Y. et al. Graft-versus-host disease disrupts intestinal microbial ecology by inhibiting Paneth cell production of alpha-defensins. *Blood* 120, 223-231 (2012).
16. Levine, J. E. et al. Low Paneth cell numbers at onset of gastrointestinal graft-versus-host disease identify patients at high risk for nonrelapse mortality. *Blood* 122, 1505-1509 (2013).
17. Hanash, A. M. et al. Interleukin-22 Protects Intestinal Stem Cells from Immune-Mediated Tissue Damage and Regulates Sensitivity to Graft versus Host Disease. *Immunity* 37, 339-350 (2012).
18. Clayburgh, D. R., Shen, L. & Turner, J. R. A porous defense: the leaky epithelial barrier in intestinal disease. *Lab Invest* 84, 282-291 (2004).
19. Kappel, L. W. et al. IL-17 contributes to CD4-mediated graft-versus-host disease. *Blood* 113, 945-952 (2009).
20. Nagalakshmi, M. L., Rascle, A., Zurawski, S., Menon, S. & de Waal Malefyt, R. Interleukin-22 activates STAT3 and induces IL-10 by colon epithelial cells. *International Immunopharmacology* 4, 679-691 (2004).
21. Pickert, G. et al. STAT3 links IL-22 signaling in intestinal epithelial cells to mucosal wound healing. *J. Exp. Med.* 206, 1465-1472 (2009).
22. Zenewicz, L. A. et al. Innate and Adaptive Interleukin-22 Protects Mice from Inflammatory Bowel Disease. 29, 947-957 (2008).
23. Zenewicz, L. A. et al. Interleukin-22 but Not Interleukin-17 Provides Protection to Hepatocytes during Acute Liver Inflammation. 27, 647-659 (2007).
24. Witte, E., Witte, K., Warszawska, K., Sabat, R. & Wolk, K. Interleukin-22: A cytokine produced by T, NK and NKT cell subsets, with importance in the innate immune defense and tissue protection. *Cytokine Growth Factor Rev* (2010).
25. Sonnenberg, G. F., Fouser, L. A. & Artis, D. Border patrol: regulation of immunity, inflammation and tissue homeostasis at barrier surfaces by IL-22. *Nat Immunol* 12, 383-390.
26. Wolk, K. et al. IL-22 regulates the expression of genes responsible for antimicrobial defense, cellular differentiation, and mobility in keratinocytes: a potential role in psoriasis. *Eur J Immunol* 36, 1309-1323 (2006).

27. Sekikawa, A. et al. Involvement of the IL-22/REG Ialpha axis in ulcerative colitis. *Lab Invest* 90, 496-505.
28. Zheng, Y. et al. Interleukin-22 mediates early host defense against attaching and effacing bacterial pathogens. *Nat Med* 14, 282-289 (2008).
29. Aujla, S. J. et al. IL-22 mediates mucosal host defense against Gram-negative bacterial pneumonia. *NatMed* 14, 275-281 (2008).
30. Das, R., Chen, X., Komorowski, R., Hessner, M. J. & Drobyski, W. R. Interleukin-23 secretion by donor antigen-presenting cells is critical for organ-specific pathology in graft-versus-host disease. *Blood* 113, 2352-2362 (2009).
31. Cella, M. et al. A human natural killer cell subset provides an innate source of IL-22 for mucosal immunity. *Nature* 457, 722-725 (2009).
32. Kreymborg, K. et al. IL-22 Is Expressed by Th17 Cells in an IL-23-Dependent Fashion, but Not Required for the Development of Autoimmune Encephalomyelitis. *J Immunol* 179, 8098-8104 (2007).
33. Sonnenberg, G. F., Monticelli, L. A., Elloso, M. M., Fouser, L. A. & Artis, D. CD4(+) lymphoid tissue-inducer cells promote innate immunity in the gut. *Immunity* 34, 122-134 (2011).
34. Zheng, Y. et al. Interleukin-22, a TH17 cytokine, mediates IL-23-induced dermal inflammation and acanthosis. *Nature* 445, 648-651 (2007).
35. Medema, J. P. & Vermeulen, L. Microenvironmental regulation of stem cells in intestinal homeostasis and cancer. *Nature* 474, 318-326.
36. Hua, G. et al. Crypt base columnar stem cells in small intestines of mice are radioresistant. *Gastroenterology* 143, 1266-1276 (2012).
37. Wang, F. et al. Isolation and characterization of intestinal stem cells based on surface marker combinations and colony-formation assay. *Gastroenterology* 145, 383-395 e381-321 (2013).
38. Yui, S. et al. Functional engraftment of colon epithelium expanded in vitro from a single adult Lgr5(+) stem cell. *Nat Med* 18, 618-623 (2012).
39. Sato, T. et al. Single Lgr5 stem cells build crypt-villus structures in vitro without a mesenchymal niche. *Nature* 459, 262-265 (2009).
40. Gerbitz A, Schultz M, Wilke A, et al. Probiotic effects on experimental graft-versus-host disease: let them eat yogurt [Research Support, Non-U.S. Gov't]. Blood. 2004; 103(11):4365-4367.
41. Jenq R R, Ubeda C, Taur Y, et al. Regulation of intestinal inflammation by microbiota following allogeneic bone marrow transplantation. The Journal of experimental medicine. 2012; 209(5):903-911.
42. Dimartino J F, Cleary M L. Mll rearrangements in haematological malignancies: lessons from clinical and biological studies. Br J Haematol. 1999; 106(3):614-626.
43. Stubbs M C, Kim Y M, Krivtsov A V, et al. MLL-AF9 and FLT3 cooperation in acute myelogenous leukemia: development of a model for rapid therapeutic assessment [Research Support, N.I.H., Extramural Research Support, Non-U.S. Gov't]. Leukemia: official journal of the Leukemia Society of America, Leukemia Research Fund, UK. 2008; 22(1):66-77.
44. Krivtsov A V, Twomey D, Feng Z, et al. Transformation from committed progenitor to leukaemia stem cell initiated by MLL-AF9 [Research Support, Non-U.S. Gov't]. Nature. 2006; 442(7104):818-822.
45. Sanos, S. L. & Diefenbach, A. Innate lymphoid cells: from border protection to the initiation of inflammatory diseases. *Immunol Cell Biol* 91, 215-224 (2013).
46. Peery, A. F. et al. Burden of gastrointestinal disease in the United States: 2012 update. *Gastroenterology* 143, 1179-1187 (2012).
47. Metcalfe, C., Kljavin, N. M., Ybarra, R. & de Sauvage, F. J. Lgr5+ stem cells are indispensable for radiation-induced intestinal regeneration. *Cell Stem Cell* 14, 149-159 (2014).
48. Ritsma, L. et al. Intestinal crypt homeostasis revealed at single-stem-cell level by in vivo live imaging. *Nature* 507, 362-365 (2014).
49. Morris, S. A. et al. Dissecting Engineered Cell Types and Enhancing Cell Fate Conversion via CellNet. *Cell* 158, 889-902 (2014).
50. Sabat, R., Ouyang, W. & Wolk, K. Therapeutic opportunities of the IL-22-IL-22R1 system. *Nat Rev Drug Discov* 13, 21-38 (2014).
51. Sawa, S. et al. RORgammat+innate lymphoid cells regulate intestinal homeostasis by integrating negative signals from the symbiotic microbiota. *Nat Immunol* 12, 320-326 (2011).
52. Longman, R. S. et al. CX3CR1+ mononuclear phagocytes support colitis-associated innate lymphoid cell production of IL-22. *J Exp Med* 211, 1571-1583 (2014).
53. Spits, H. et al. Innate lymphoid cells—a proposal for uniform nomenclature. *Nat Rev Immunol* 13, 145-149 (2013).
54. Munneke, J. M. et al. Activated innate lymphoid cells are associated with a reduced susceptibility to graft-versus-host disease. *Blood* 124, 812-821 (2014).
55. Pearson, C., Uhlig, H. H. & Powrie, F. Lymphoid microenvironments and innate lymphoid cells in the gut. *Trends Immunol* 33, 289-296 (2012).
56. Zhou, W. J., Geng, Z. H., Spence, J. R. & Geng, J. G. Induction of intestinal stem cells by R-spondin 1 and Slit2 augments chemoradioprotection. *Nature* 501, 107-111 (2013).
57. Choi, S.-M. et al. Innate Stat3-mediated induction of the antimicrobial protein Reg3γ is required for host defense against MRSA pneumonia. *J Exp Med* 210, 551-561 (2013).
58. Matthews, J. R., Sansom, O. J. & Clarke, A. R. Absolute requirement for STAT3 function in small-intestine crypt stem cell survival. *Cell Death Differ* 18, 1934-1943 (2011).
59. Ferrara, J. L., Levine, J. E., Reddy, P. & Holler, E. Graft-versus-host disease. *Lancet* 373, 1550-1561 (2009).
60. Blazar, B. R., Murphy, W. J. & Abedi, M. Advances in graft-versus-host disease biology and therapy. *Nat Rev Immunol* 12, 443-458 (2012).
61. Schroeder, M. A. & DiPersio, J. F. Mouse models of graft-versus-host disease: advances and limitations. *Dis Model Mech* 4, 318-333 (2011).
62. Kolls, J. K., McCray, P. B., Jr. & Chan, Y. R. Cytokine-mediated regulation of antimicrobial proteins. *Nat Rev Immunol* 8, 829-835 (2008).
63. Walker, C. R. et al. Intestinal intraepithelial lymphocyte-enterocyte crosstalk regulates production of bactericidal angiogenin 4 by Paneth cells upon microbial challenge. *PLoS One* 8, e84553 (2013).
64. Kabiri, Z. et al. Stroma provides an intestinal stem cell niche in the absence of epithelial Wnts. *Development* 141, 2206-2215 (2014).

65. Zhao, K. et al. Interleukin-22 Aggravates Murine Acute Graft-Versus-Host Disease by Expanding Effector T Cell and Reducing Regulatory T Cell. *J Interferon Cytokine Res* 34, 707-715 (2014).

We claim:

1. A method for treating gastrointestinal graft versus host disease (GVHD) in a subject, the method comprising injecting the subject with a therapeutically effective amount of an interleukin-22 (IL-22), wherein the subject is an allo-hematopoietic stem cell transplant recipient.

2. The method of claim 1, wherein said IL-22 is recombinant IL-22.

3. The method of claim 2, wherein said recombinant IL-22 is human IL-22.

4. The method of claim 1, wherein said IL-22 is in the form of an IL-22 dimer.

5. The method of claim 1, wherein the IL-22 is in the form of a fusion protein.

6. The method of claim 1, wherein said therapeutically effective amount of IL-22 is administered to the subject before transplant.

7. The method of claim 1, wherein said therapeutically effective amount of IL-22 is administered to the subject once onset of symptoms associated with injury to the gastrointestinal tract is observed.

8. The method of claim 1, wherein said therapeutically effective amount of IL-22 is administered to the subject from 1 day to 6 months following transplant.

9. The method of claim 1, wherein said therapeutically effective amount of IL-22 is administered to the subject beginning from 1 week to 4 months following transplant.

10. The method of claim 1, wherein said IL-22 is administered daily.

11. The method of claim 1, wherein said IL-22 comprises an IL-22-carrier fusion protein and the carrier comprises an Fc fragment selected from human IgG1, human IgG2, human IgG3, human IgG4, and human albumin.

12. The method of claim 11, wherein said IL-22 comprises an IL-22-human IgG2 Fc fragment fusion protein.

13. The method of claim 12, wherein said IL-22 is in the form of an IL-22 dimer.

14. The method of claim 1, further comprising co-administering an immunosuppressive agent to the subject.

15. The method of claim 1, further comprising co-administering prednisone to the subject.

* * * * *